(12) United States Patent
Kipps et al.

(10) Patent No.: US 8,212,009 B2
(45) Date of Patent: Jul. 3, 2012

(54) METHODS AND COMPOUNDS FOR LYMPHOMA CELL DETECTION AND ISOLATION

(75) Inventors: Thomas J. Kipps, San Diego, CA (US); Tetsuya Fukuda, Yokohama (JP); Tomoyuki Endo, San Diego, CA (US); Suping Zhang, San Diego, CA (US); Liguang Chen, San Diego, CA (US); H. Elizabeth Broome, Lakeside, CA (US)

(73) Assignee: The Regents of the University of California, Oakland, CA (US)

( * ) Notice: Subject to any disclaimer, the term of this patent is extended or adjusted under 35 U.S.C. 154(b) by 19 days.

(21) Appl. No.: 12/545,731

(22) Filed: Aug. 21, 2009

(65) Prior Publication Data

US 2010/0062005 A1    Mar. 11, 2010

Related U.S. Application Data

(63) Continuation-in-part of application No. PCT/US2008/054613, filed on Feb. 21, 2008, now abandoned, and a continuation-in-part of application No. PCT/US2006/042689, filed on Oct. 30, 2006, now abandoned.

(60) Provisional application No. 60/971,818, filed on Sep. 12, 2007, provisional application No. 60/731,210, filed on Oct. 28, 2005, provisional application No. 61/099,149, filed on Sep. 22, 2008.

(51) Int. Cl.
    *C07K 16/00*  (2006.01)
    *C07K 16/18*  (2006.01)

(52) U.S. Cl. .................................. 530/387.9; 530/388.1

(58) Field of Classification Search ........................ None
    See application file for complete search history.

(56) References Cited

U.S. PATENT DOCUMENTS

| | | | |
|---|---|---|---|
| 4,489,710 A | 12/1984 | Spitler | |
| 4,569,789 A | 2/1986 | Blattler et al. | |
| 4,625,014 A | 11/1986 | Senter et al. | |
| 4,638,045 A | 1/1987 | Kohn et al. | |
| 4,671,958 A | 6/1987 | Rodwell et al. | |
| 6,287,569 B1 | 9/2001 | Kipps et al. | |
| 2003/0124141 A1 | 7/2003 | Haas et al. | |
| 2004/0116330 A1 | 6/2004 | Naito et al. | |
| 2004/0253240 A1 | 12/2004 | Fruchart et al. | |
| 2005/0246794 A1 | 11/2005 | Khvorova et al. | |

FOREIGN PATENT DOCUMENTS

| | | |
|---|---|---|
| WO | WO 90/07861 A1 | 7/1990 |
| WO | WO 91/17271 A1 | 11/1991 |
| WO | WO 92/01047 A1 | 1/1992 |
| WO | WO 2005/100605 A1 | 10/2005 |

OTHER PUBLICATIONS

Paul, Fundamental Immunology, 3rd Edition, 1993, pp. 292-295, under the heading "Fv Structure and Diversity in Three Dimensions".*
Rudikoff et al (Proc. Natl. Acad. Sci. USA, 79(6):1979-1983, Mar. 1982).*
Bendig M. M. (Methods: A Companion to Methods in Enzymology, 1995; 8:83-93).*
MacCallum et al (J. Mol. Biol., 262, 732-745, 1996).*
Casset et al (Biochemical and Biophysical Research Communications, 307:198-205, 2003).*
Allzadeh et al., "Distinct Types of Diffuse Large B-Cell Lymphoma Identified by Gene Expression Profiling," *Nature* (2000), 403:503-511, Macmillan Magazines Ltd.
Baskar et al., "Unique Cell Surface Expression of Receptor Tyrosine Kinase ROR1 in Human B-Cell Chronic Lymphocytic Leukemia," *Clinical Cancer Research* (2008), 14(2):396-404.
Fukuda et al., "Antisera Induced by Infusions of Autologous Ad-CD154-Leukemia B Cells Idnetify ROR1 as an Oncofetal Antigen and Receptor for Wnt5a," *Proceedings of the National Academy of Sciences*, USA (2008), 105(8):3047-3052.
Katoh, M., "WNT/PCP Signaling Pathway and Human Cancer (Review)," *Oncology Reports* (2005), 14(6):1583-1588.
Masiakowski and Carroll, "A Novel Family of Cell Surface Receptors with Tyrosine Kinase-Like Domain," *The Journal of Biological Chemistry* (1992) 267(36):26181-26190, The American Society for Biochemistry and Molecular Biology, Inc.
Paganoni and Ferreira, "Expression and Subcellular Localization of Ror Tyrosine Kinase Receptors Are Developmentally Regulated in Cultured Hippocampal Neurons," *Journal of Neuroscience Research* (2003), 73:429-440, Wiley-Liss, Inc.
Paganoni et al., "Differential Subcellular Localization of Ror Tyrosine Kinase Receptor in Cultured Astrocytes," *GLIA* (2004), 46:456-466, Wiley-Liss, Inc.
Reddy et al., "Human Neural Tissues Express a Truncated Ror1 Receptor Tyrosine Kinase, Lacking Both Extracellular and Transmembrane Domains," *Oncogene* (1996), 13:1559-1559, Stockton Press.
Robetorye et al., "Microarray Analysis of B-Cell Lymphoma Cell Lines with the t(14;18)," *Journal of Molecular Diagnostics* (2002), 4(3):123-136, American Society for Investigative Pathology and the Association for Molecular Pathology. Allzadeh et al., "Distinct types of diffuse large B-cell lymphoma identified by gene expression profiling", *Nature*, 403:503-511 (2000).

(Continued)

*Primary Examiner* — Laura B Goddard
(74) *Attorney, Agent, or Firm* — DLA Piper LLP (US)

(57) ABSTRACT

Compositions comprising a purified and/or isolated antibody, humanized antibodies, precipitates and anti-sera that specifically bind to or are otherwise directed against ROR1 protein. The compositions may be used for detecting ROR1 in a sample from a subject that is suspected or known to contain cancer cells. The ROR1 antibodies are especially useful in identifying and treating lymphomas and ademocarcinomas. Vaccines and related methods for protecting a subject against diseases that involve expression of ROR1 are also provided, as are human anti-sera effective in abrogating interactions between Wnt5a protein and ROR1 that contribute to the survival of certain cancer cells, such as CLL cells.

9 Claims, 68 Drawing Sheets

OTHER PUBLICATIONS

Al-Shawi et al., "Expression of the Ror1 and Ror2 Receptor Tyrosine Kinase Genes during Mouse Development," *Dev. Genes Evol.*, 211:161-171 (2001).
Ausubel F.M. et al., Editors, Current Protocols in Molecular Biology, John Wiley & Sons, Inc. (1999).
Baskar et al., "Unique Cell Surface Expression of Receptor Tyrosine Kinase ROR1 in Human B-Cell Chronic Lymphocytic Leukemia", *Clinical Cancer Research*, 14(2):396-404 (2008).
Cantwell et al., "Adenovirus Vector Infection of Chronic Lymphocytic Leukemia B Cells", *Blood*, 88:4676-4683 (1996).
Carson et al., "Restricted expression of the orphan tyrosine kinase receptor ROR1 in chronic lymphocytic leukemia", *Blood*, American Society of Hematology, U.S., 104(11 Part 1):221A (2004).
Clackson et al., "Making Antibody Fragments Using Phage Display Libraries", *Nature*, 352:624-628 (1991).
Cwirla et al., "Peptides on Phage: A Vast Library of Peptides for Identifying Ligands", *Proc. Natl. Acad. Sci. USA*, 87:6378-6382 (1990).
Delaloye et al., "Tumor Imaging with Monoclonal Antibodies", *Seminars in Nuclear Medicine*, 25:144-164 (1995).
Eckelman et al., "Three Approaches to Radiolabeling Antibodies with 99mTC", *Nucl. Med. Biol.*, 16:171-176 (1989).
Elbashir et al., "Duplexes of 21-Nucleotide RNAs Mediate RNA Interference in Cultured Mammalian Cells", *Nature*, 411:494-498 (2001).
Fukuda et al., "Antisera induced by infusions of autologous Ad-CD154-leukemia B cells identify ROR1 as an oncofetal antigen and receptor for Wnt5a", *PNAS*, 105(8):3047-3052 (2008).
Fukuda et al., "Restricted Expression of the Orphan Tyrosine Kinase Receptor ROR1 in Chronic Lymphocytic Leukemia", *ASH Annual Meeting Abstracts*, p. 221a, Abstract 772 (2004).
Galfrè and Milstein, "Preparation of Monoclonal Antibodies: Strategies and Procedures", *Methods in Enzymology*, 73:3-46 (1981).
Goldenberg et al., "Cancer Imaging with a New 99m-TC-Antibody Method", *Eur. J. Nucl. Med.*, 15:426 (1989).
Handbook of Experimental Immunology in Four Volumes, vol. 1: Immunochemistry, Weir, D.M., Editor, 4th Edition, Blackwell Scientific Publications, Oxford (1986).
Harlow & Lane, Antibodies, A Laboratory Manual, Cold Spring Harbor Laboratory Press, N.Y. (1988).
Holliger et al., ""Diabodies": Small Bivalent and Bispecific Antibody Fragments", *Proc. Natl. Acad. Sci. USA*, 90:6444-6448 (1993).
Hoogenboom et al., "Multi-Subunit Proteins on the Surface of Filamentous Phage: Methodologies for Displaying Antibody (Fab) Heavy and Light Chains", *Nucleic Acids Research*, 19:4133-4137 (1991).
Katoh M., "WNT/PCP signaling pathway and human cancer (review)", *Oncology Reports*, 14(6):1583-1588 (2005).
Klein et al., "Gene Expression Profiling of B Cell Chronic Lymphocytic Leukemia Reveals a Homogeneous Phenotype Related to Memory B Cells", *J. Exp. Med.*, 194:1625-1638 (2001).
Koren et al., "Characterization of a Monoclonal Antibody that Binds Equally to all Apolipoprotein and Lipoprotein Forms of Human Plasma Apolipoprotein B.I. Specifity and Binding Studies", *Biochimica et Biophysica Acta*, 876:91-100 (1986).
Lechner et al., "Anticarcinoembryonic Antigen Immunoscintigraphy with a 99mTC-Fab' Fragment (Immu 4™) in Primary and Recurrent Colorectal Cancer", *Dis. Colon Rectum*, 36:930-935 (1993).
Lowman et al., "Selecting High-Affinity Binding Proteins by Monovalent Phage Display", *Biochemistry*, 30:10832-10838 (1991).
MacKeigan et al., "Sensitized RNAi screen of human kinases and phosphatases identifies new regulators of apoptosis and chemoresistance", *Nature Cell Biology*, 7(6):591-600 (2005). (Supplemental information, Nature Publishing Group, pp. 1-4).
Masiakowski & Carroll, "A Novel Family of Cell Surface Receptors with Tyrosine Kinase-like Domain", *The Journal of Biological Chemistry*, 267(36):26181-26190 (1992).
Matsuda et al., "Expression of the Receptor Tyrosine Kinase Genes, Ror1 and Ror2, during Mouse Development", *Mechanisms of Development*, 105:153-156 (2001).
Moffat et al., "Clinical Utility of External Immunoscintigraphy with the IMMU-4 Technetium-99m Fab' Antibody Fragment in Patients Undergoing Surgery for Carcinoma of the Colon and Rectum: Results of a Pivotal, Phase III Trial", *Journal of Clinical Oncology*, 14:2295-2305 (1996).
Paganoni & Ferreira, "Expression and Subcellular Localization of Ror Tyrosine Kinase Receptors Are Developmentally Regulated in Cultured Hippocampal Neurons", *Journal of Neuroscience Research*, 73:429-440 (2003).
Paganoni et al., "Differential Subcellular Localization of Ror Tyrosine Kinase Receptors in Cultured Astrocytes", *GLIA*, 46:456-466 (2004).
Parmley and Smith, "Filamentous Fusion Phage Cloning Vectors for the Study of Epitopes and Design of Vaccines", *Adv. Exp. Med. Biol.*, 251:215-218 (1989).
Queen et al., "A Humanized Antibody that Binds to the Interleukin 2 Receptor", *Proc. Natl. Acad. Sci. USA*, 86:10029-10033 (1989).
Reddy et al., "Human neural tissues express a truncated Ror1 receptor tyrosine kinase, lacking both extracellular and transmembrane domains", *Oncogene*, 13:1555-1559 (1996).
Robetorye et al., "Microarray Analysis of B-Cell Lymphoma Cell Lines with the t(14; 18)", *Journal of Molecular Diagnostics*, 4(3):123-136 (2002).
Rosenwald et al., "Relation of Gene Expression Phenotype to Immunoglobulin Mutation Genotype in B Cell Chronic Lymphocytic Leukemia", *J. Exp. Med.*, 194:1639-1647 (2001).
Sambrook et al., Molecular Cloning: A Laboratory Manual, Cold Spring Harbor Laboratory Press, 2nd ed., N.Y. (1989).
Scopes, R.K., Protein Purification, Principles and Practice, Springer-Verlag, N.Y. (1982).
Vernon et al., "Herpesvirus Vaccine Development: Studies of Virus Morphological Components", *New Trends and Developments in Vaccines*, Chapter 13: pp. 179-210 (1978).
Wierda et al., "CD40-Ligand (CD154) Gene Therapy for Chronic Lymphocytic Leukemia", *Blood*, 96:2917-2924 (2000).
Winnacker, Ernst-L., From Genes to Clones, Introduction to Gene Technology, translated by Horst Ilelgautfs, VCH Publishers, N.Y. (1987).
Yoda et al., "Expression and Function of the Ror-Family Receptor Tyrosine Kinases During Development: Lessons from Genetic Analyses of Nematodes, Mice, and Humans", *Journal of Receptors and Signal Transduction*, 23:1-15 (2003).

* cited by examiner

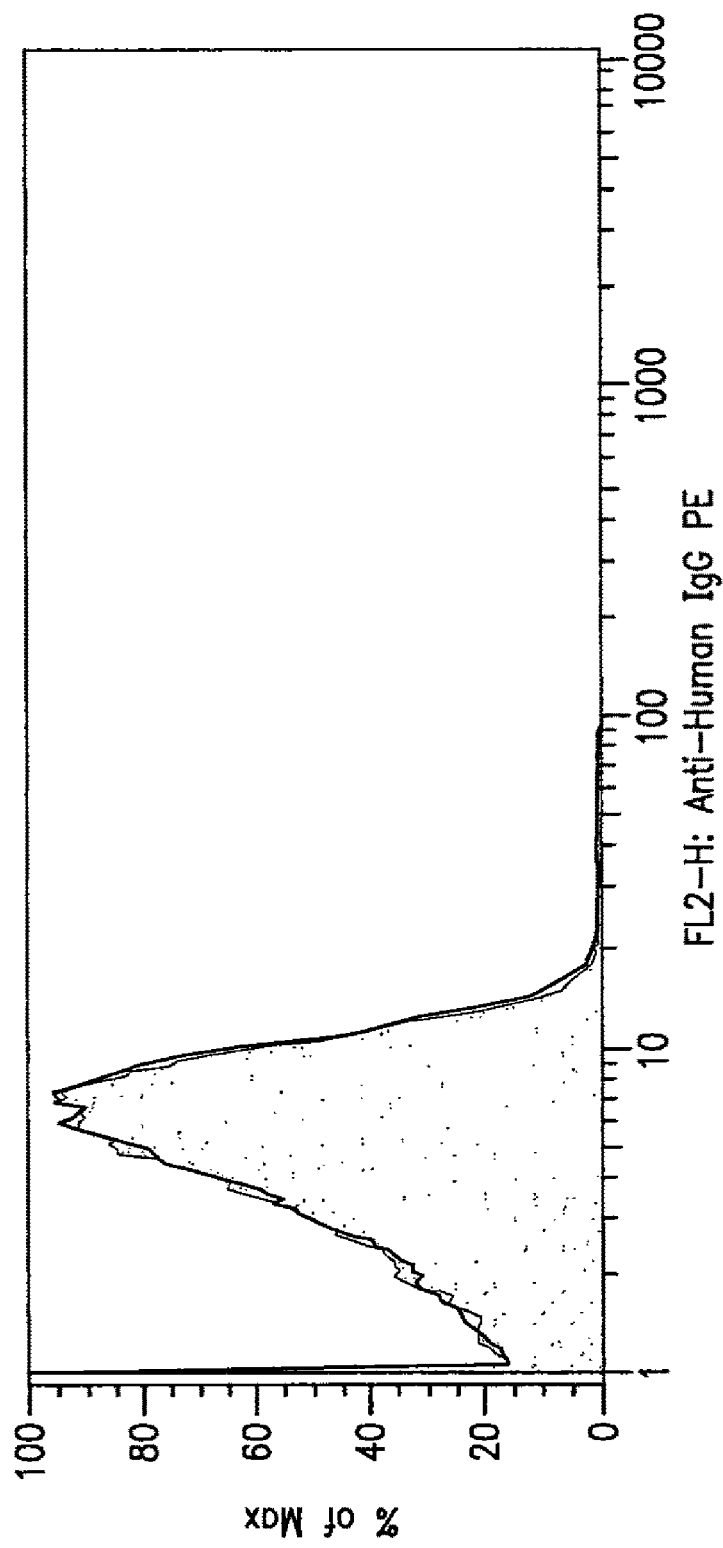

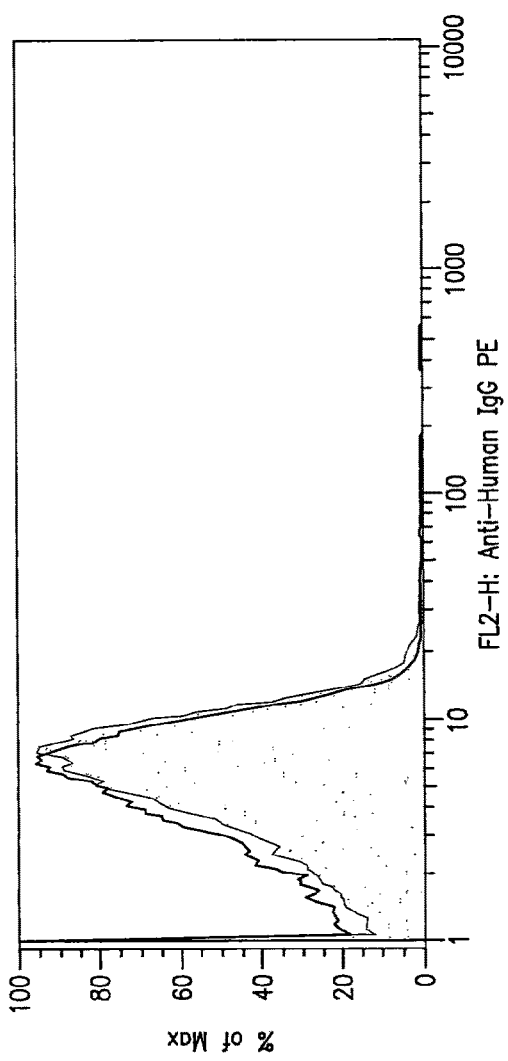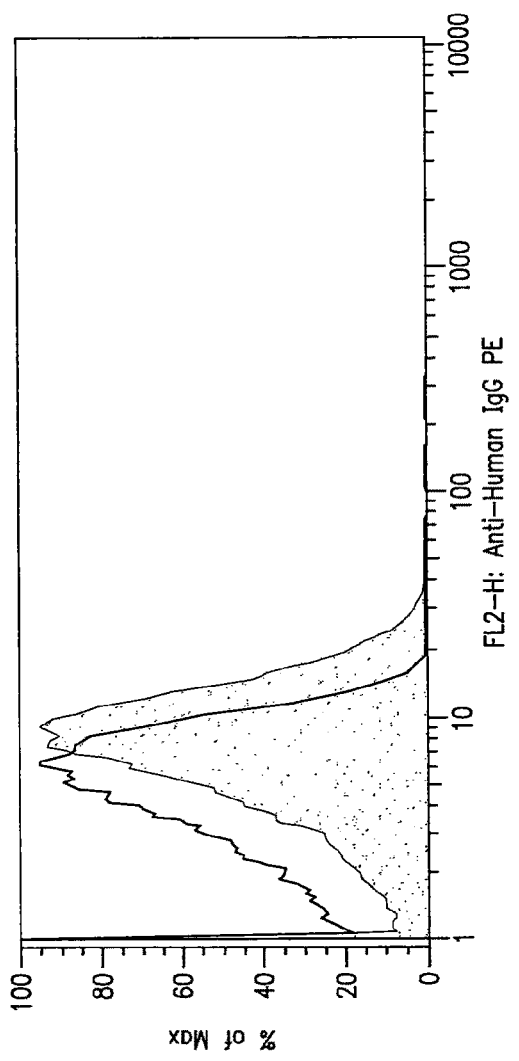
FIG. 2a (cont.)

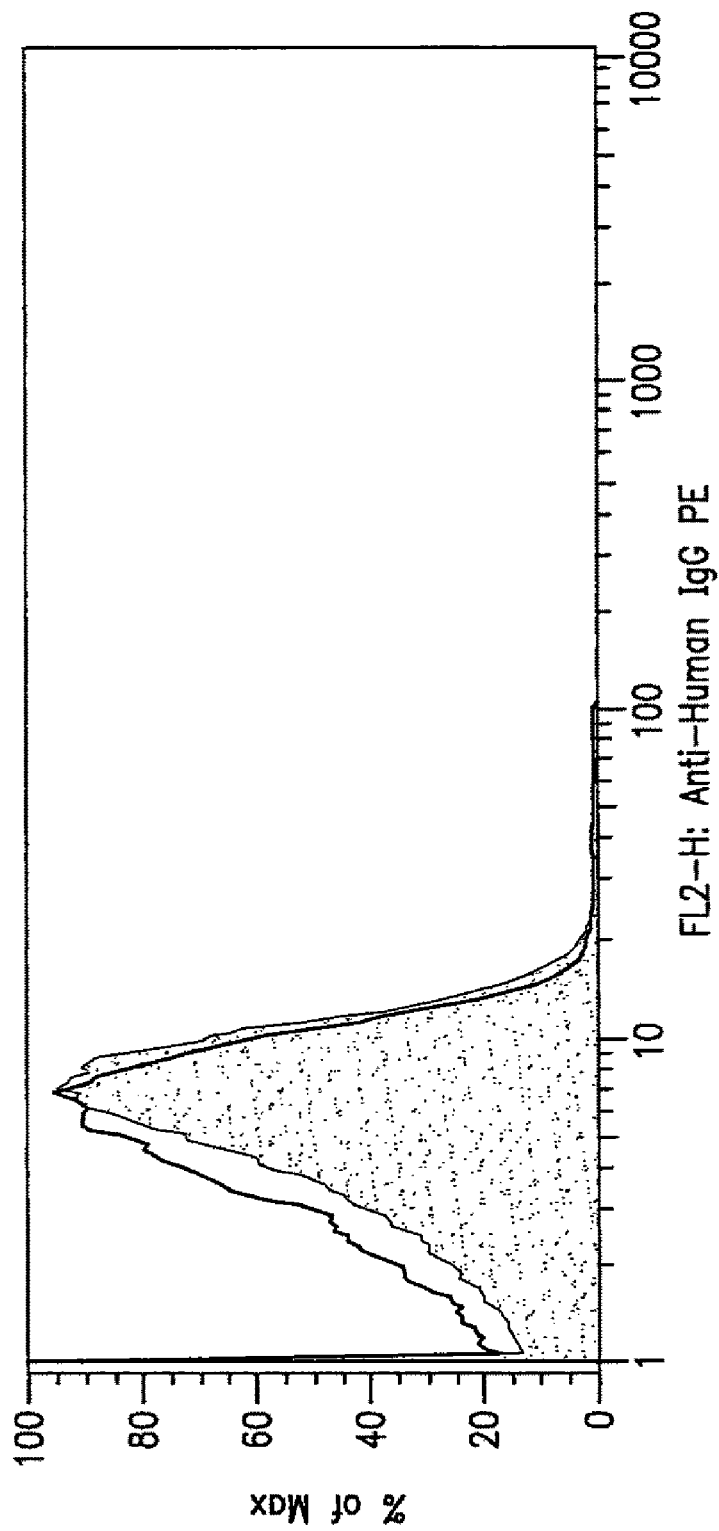

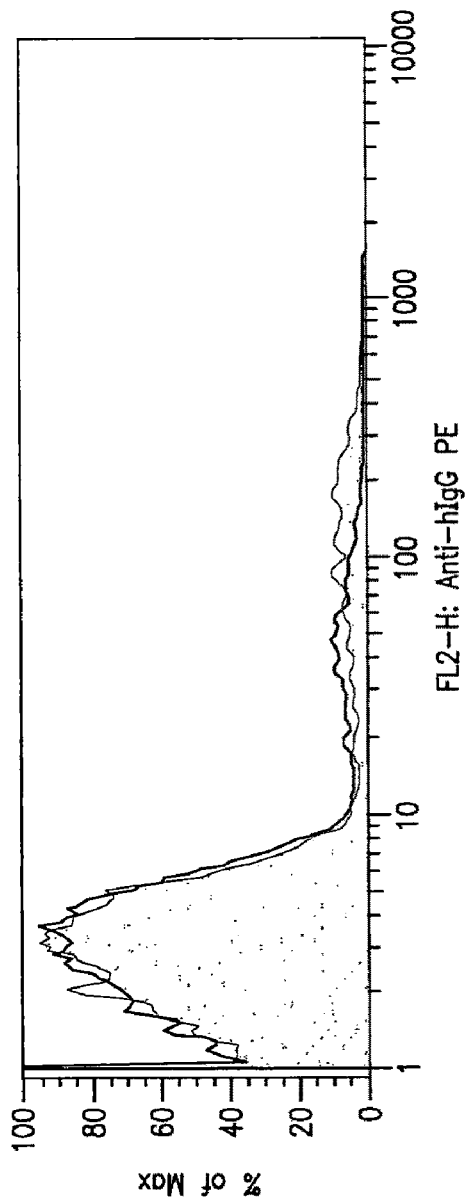
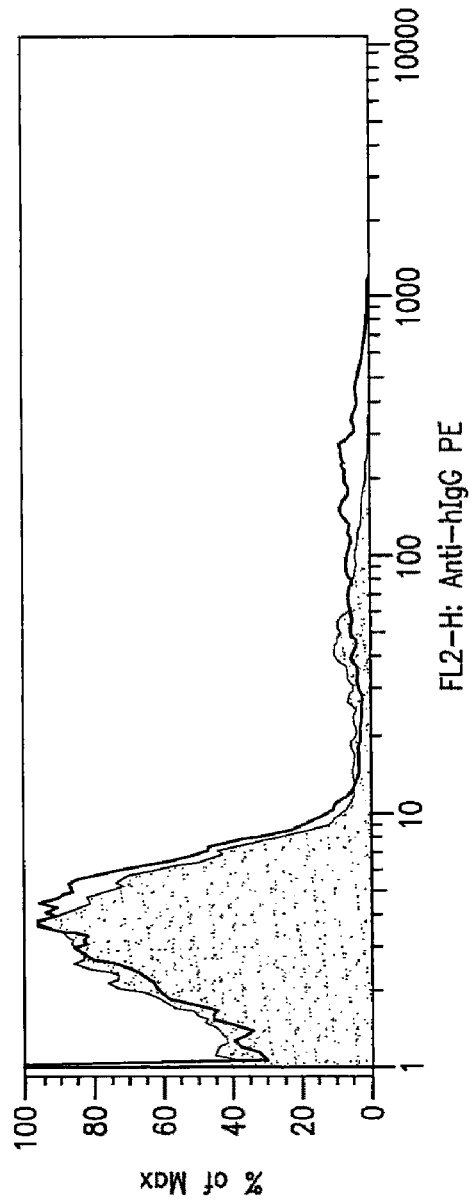
FIG. 2b

1: 300 μg of CHO cell lysate
2: 300 μg of CHO-ROR1 cell lysate
3: 300 μg of CLL cell lysate
4: 600 μg of CLL cell lysate

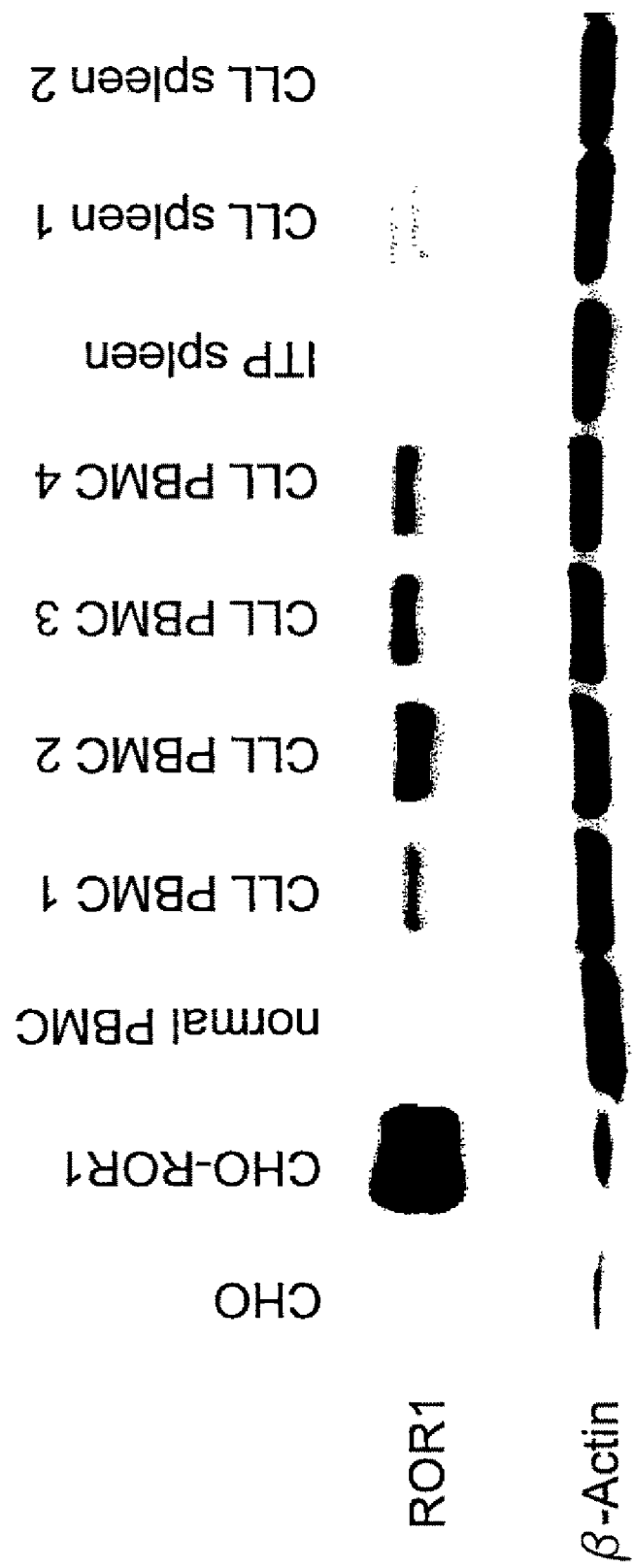

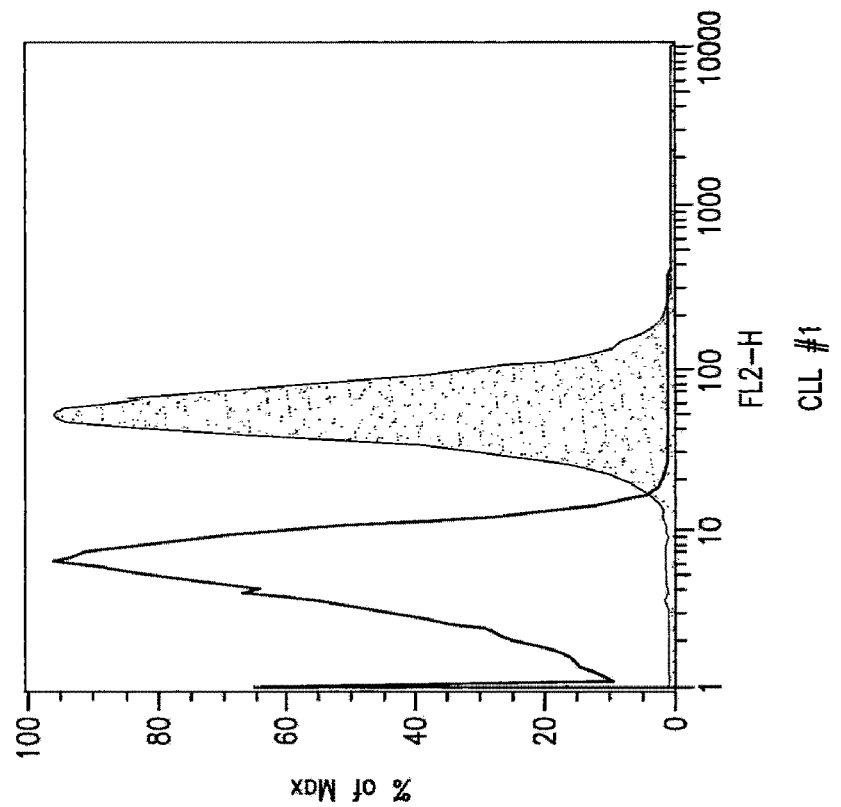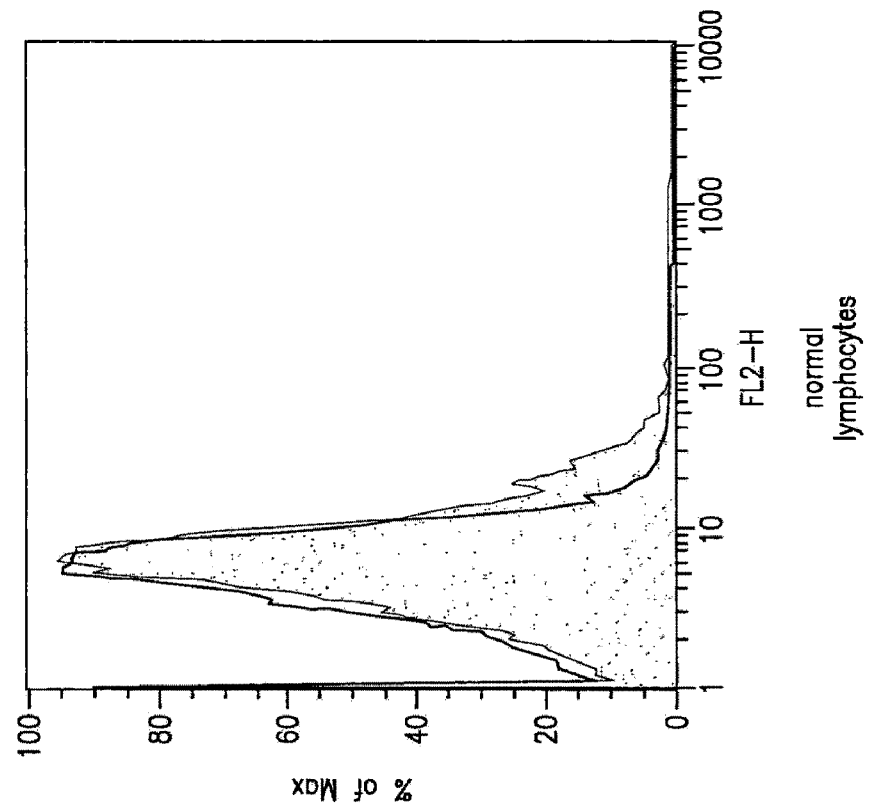
FIG. 4d

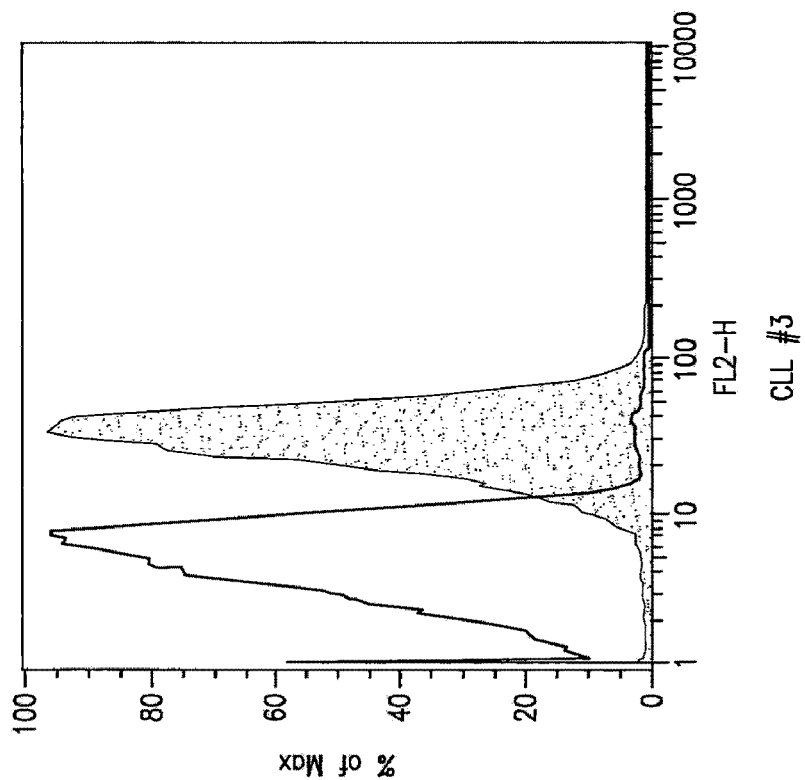
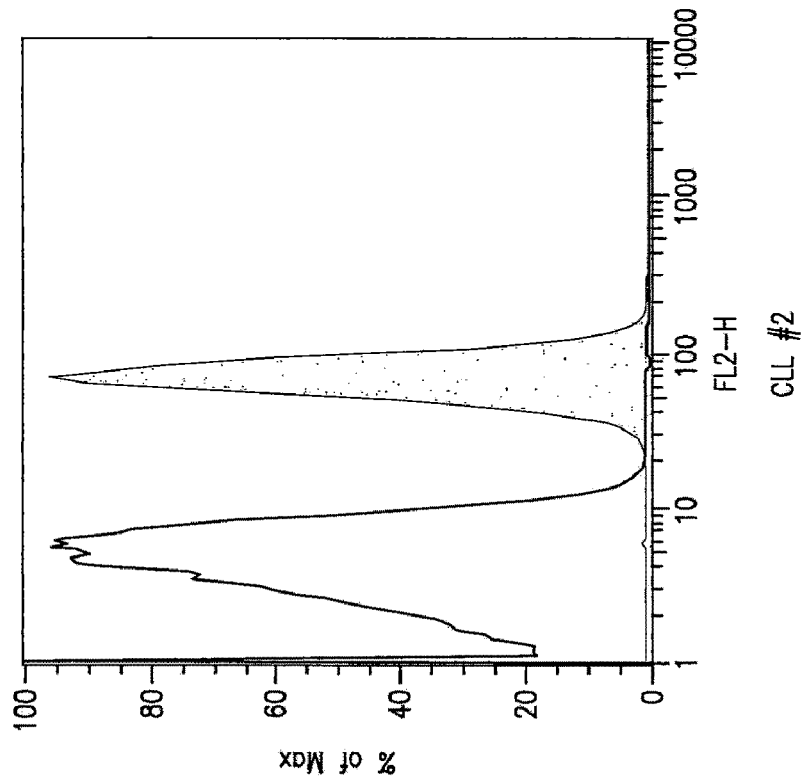
FIG. 4d (cont.)

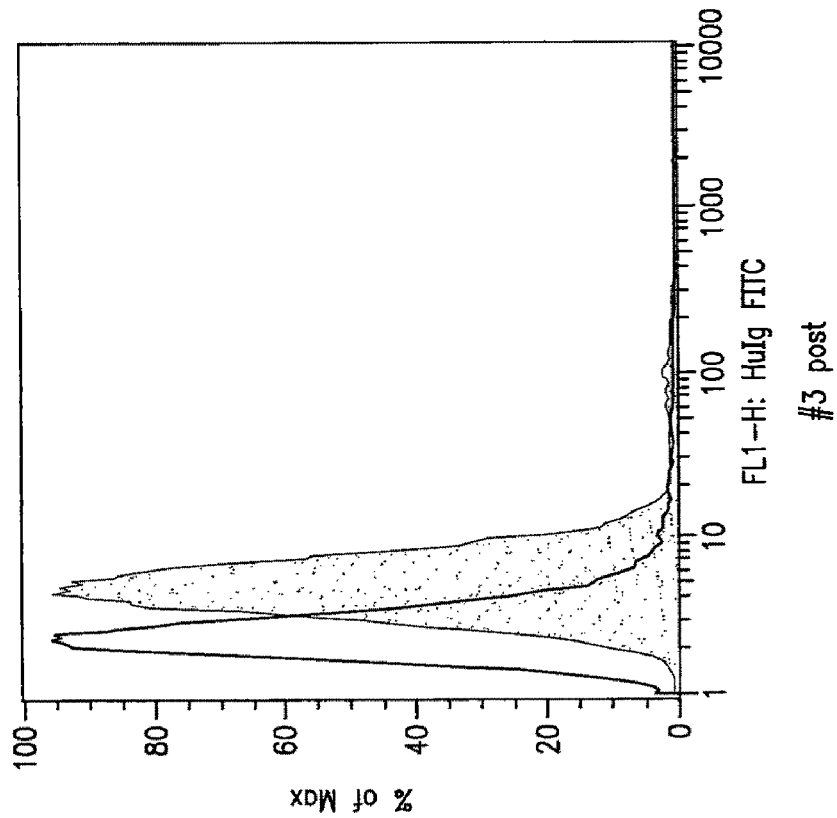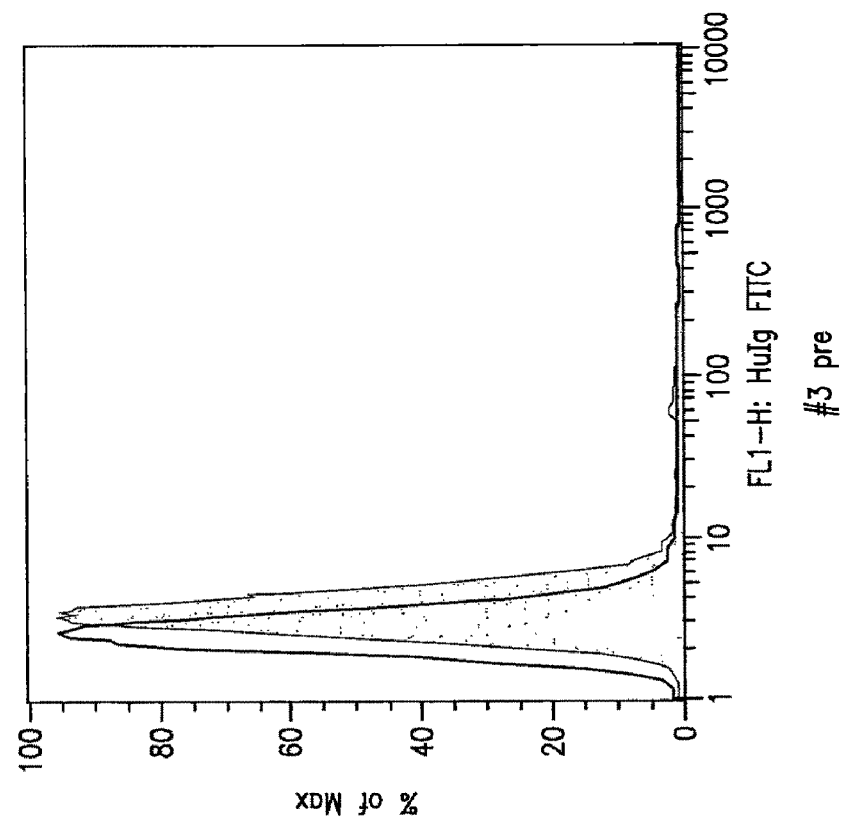
FIG. 5a (cont.)

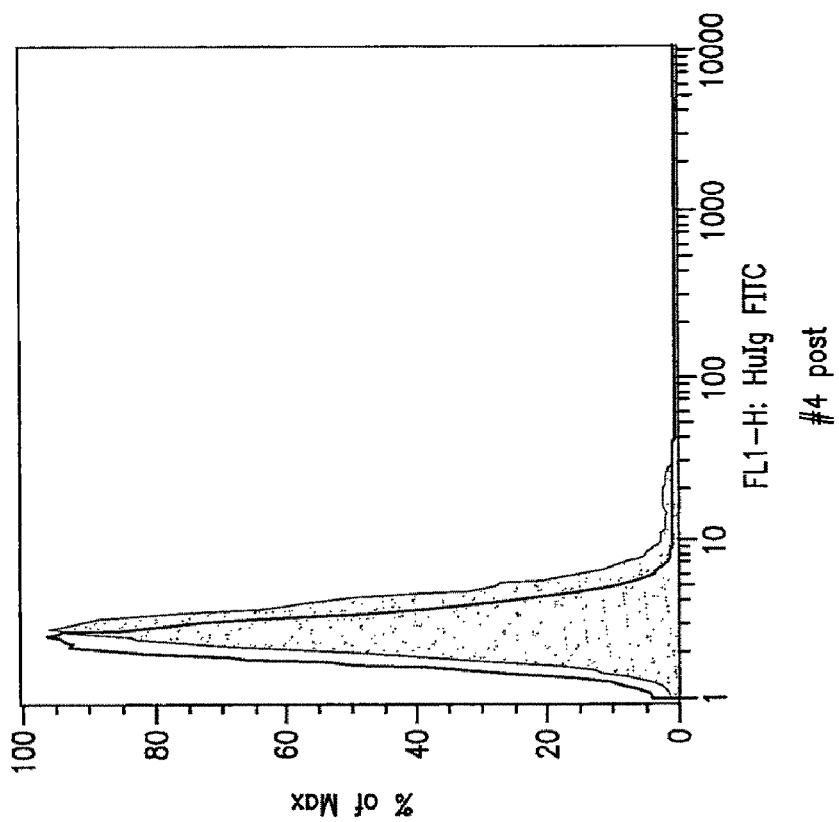
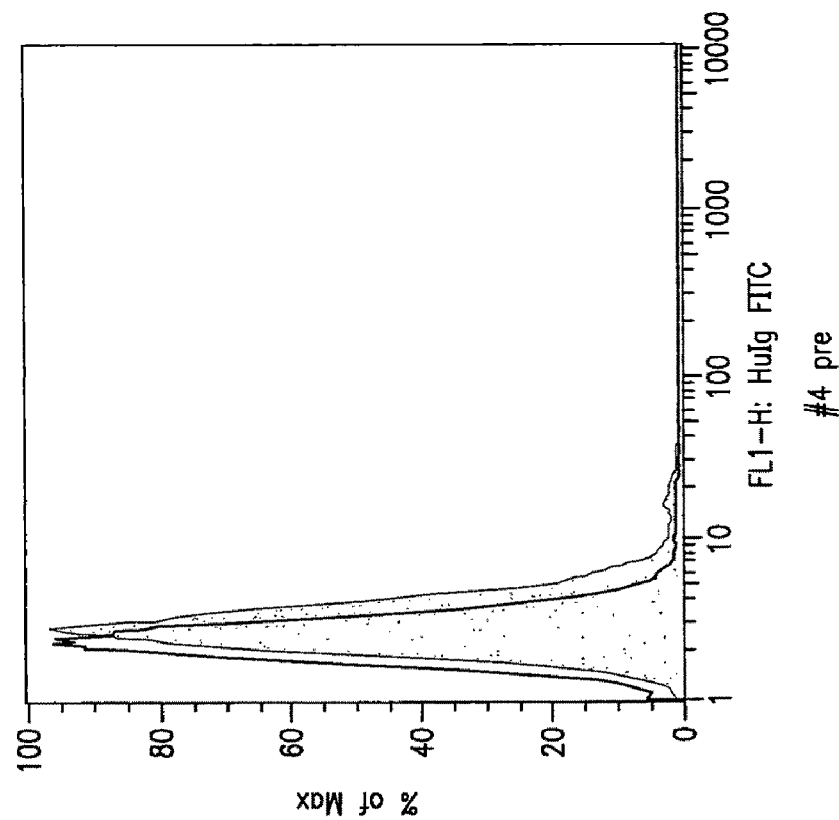
FIG. 5a (cont.)

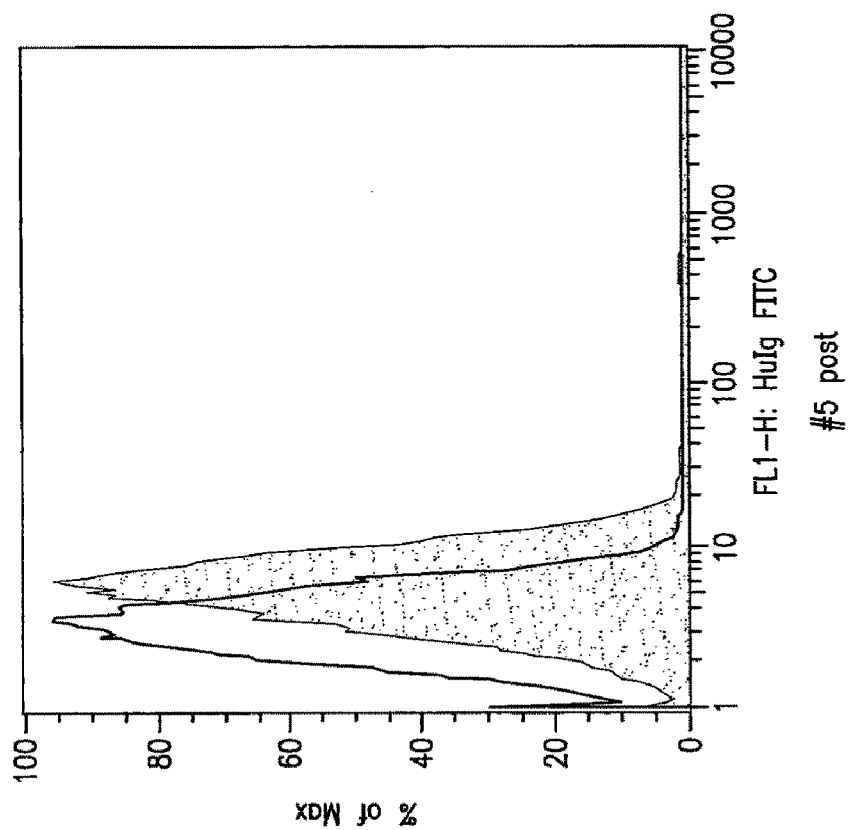
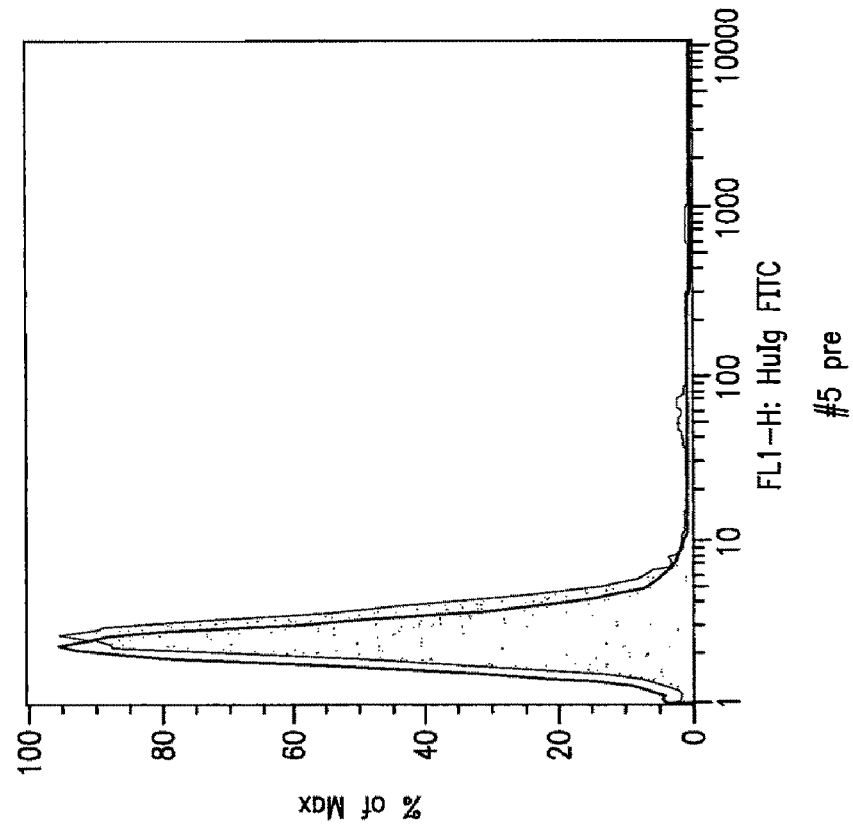
FIG. 5a (cont.)

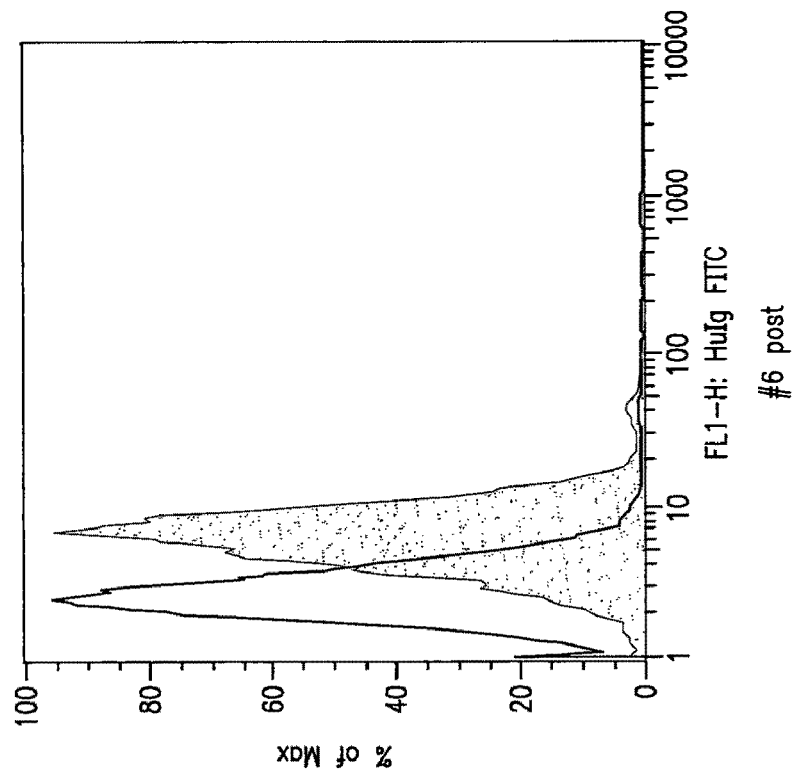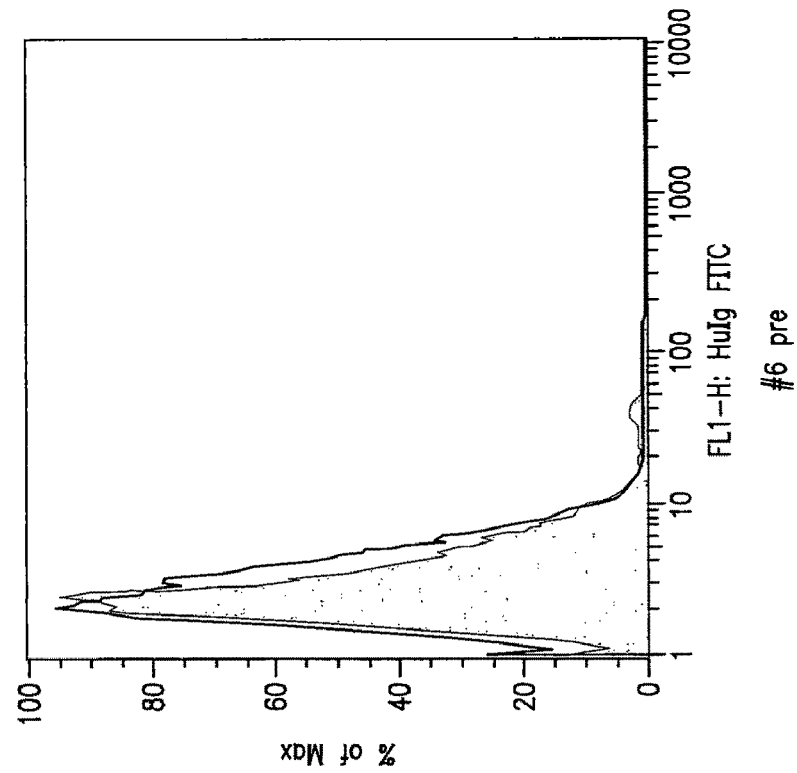
FIG. 5a (cont.)

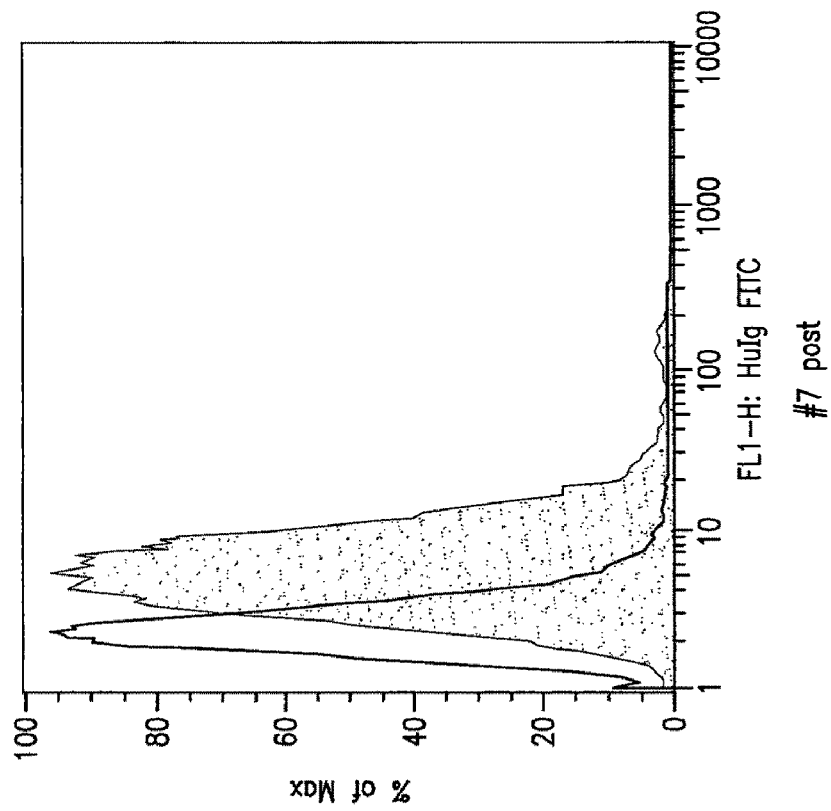
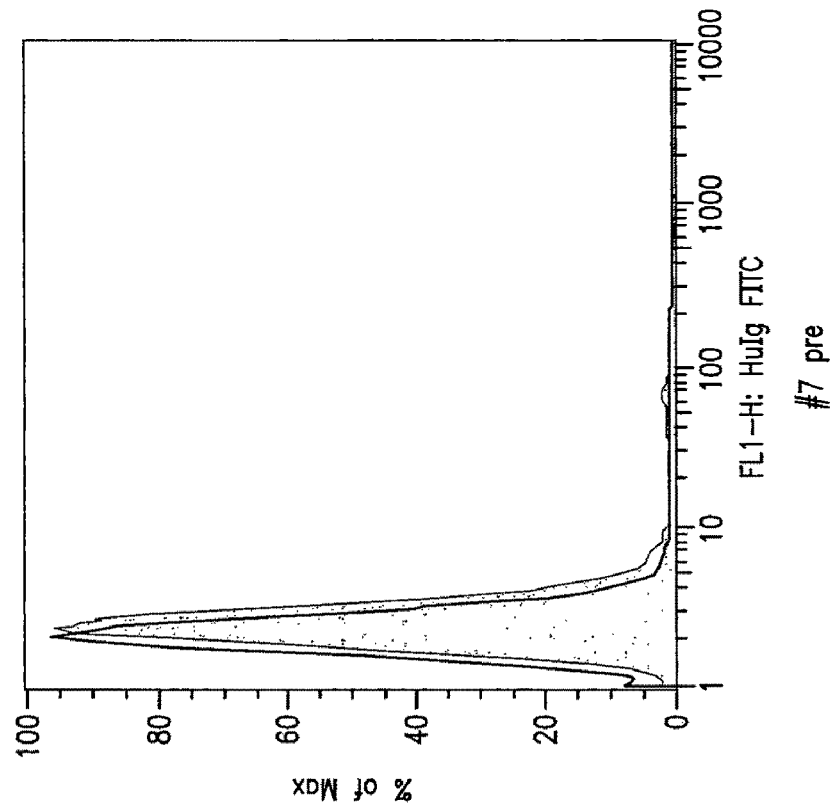
FIG. 5a (cont.)

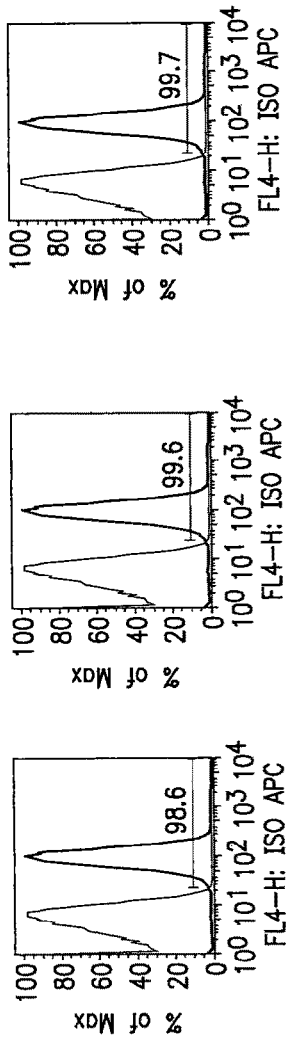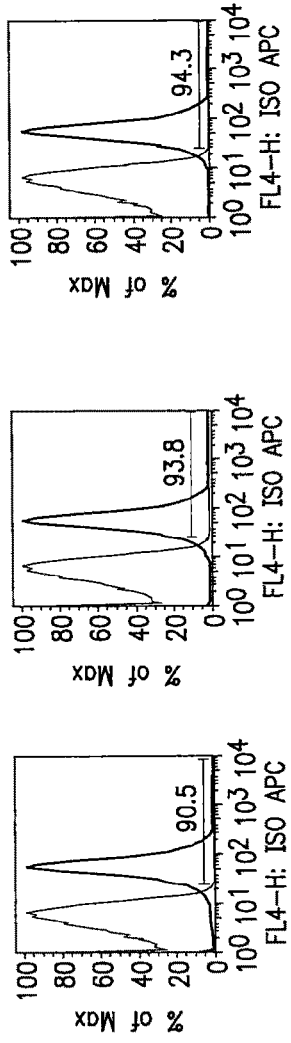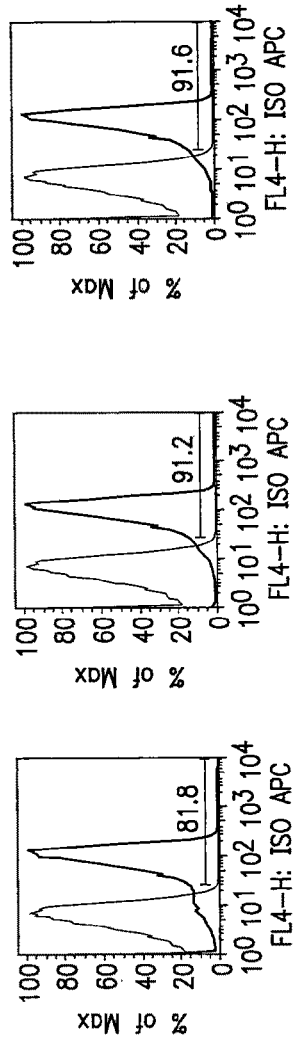
FIG. 8

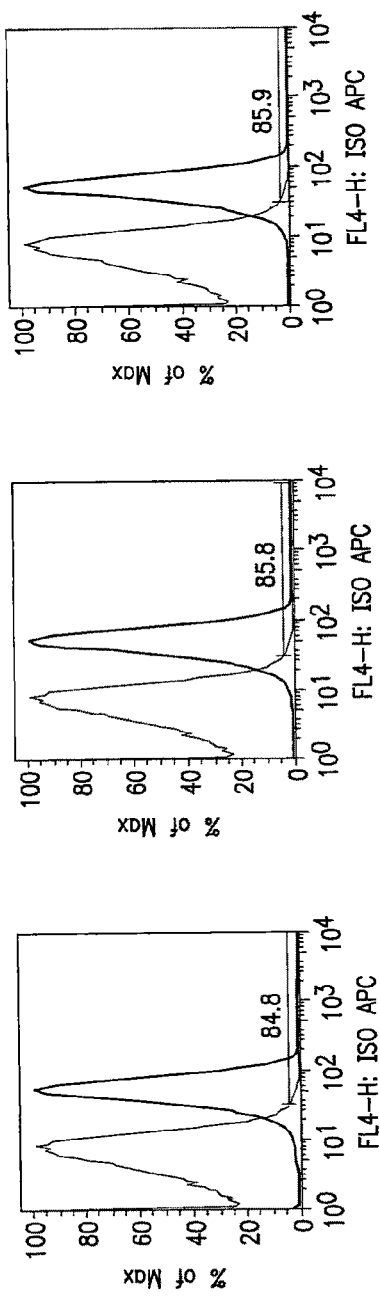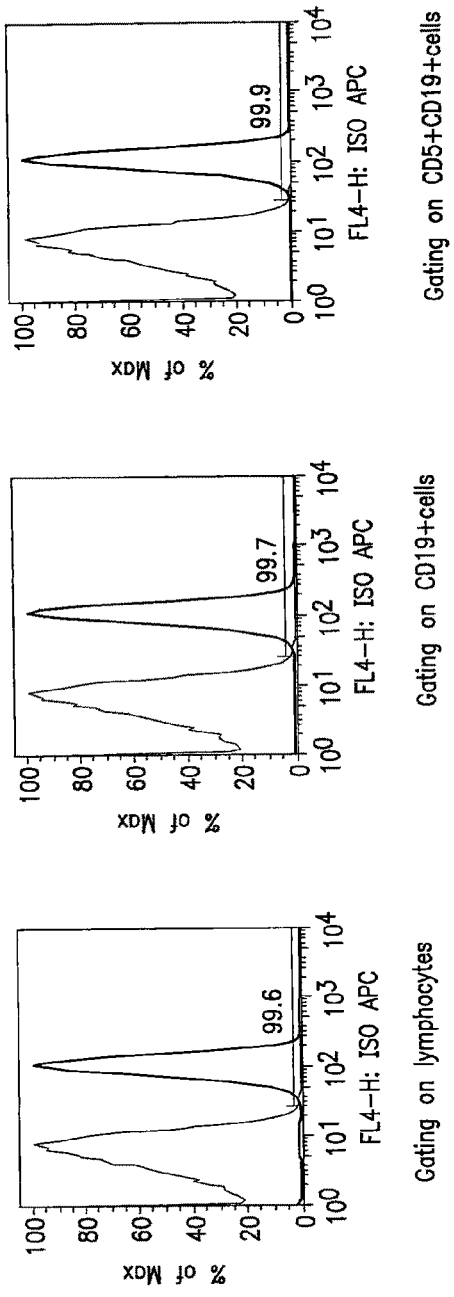
FIG. 11

```
   1 gttgagcgag agagggagcg tggagagctg gagcagccgc caccgccgcc gccgagggag
  61 ccccgggacg gcagccctg ggcgcagggt gcgctgttct cggagtccga cccagggcga
 121 ctcacgccca ctggtgcgac ccggacagcc tgggactgac ccgccgccc aggcgaggct
 181 gcagccagag ggctgggaag ggatcgcgct cgccgcatcc agaggcggcc aggcggaggc
 241 gagggagcag gttagaggga caaagagctt tgcagacgtc cccggcgtcc tgcgagcgcc
 301 agcggccggg acgaggcggc cggagcccg ggaagagccc gtggatgttc tgcgcgcggc
 361 ctgggagccg ccgccgccgc cgcctcagcg agaggaggaa tgcaccggcc gcgccgccgc
 421 gggacgcgc cgccgctcct ggcgctgctg ccgccgctgc tgctggccgc acgcggggct
 481 gctgcccaag aaacagagct gtcagtcagt gctgaattag tgcctacctc atcatggaac
 541 atctcaagtg aactcaacaa agattcttac ctgaccctcg atgaaccaat gaataacatc
 601 accacgtctc tgggccagac agcagaactg cactgcaaag tctctggaa tccacctccc
 661 accatccgct ggttcaaaaa tgatgtcct gtggtccagg agcccccgag gctctctttt
 721 cggtccacca tctatggctc tcggctgcgg attagaaacc tcgacaccac agacacaggc
 781 tactctccagt gcgtggcaac aaacggcaag gaggtggttt cttccactgg agtcttgttt
 841 gtcaagtttg gcccccctcc cactgcaagt ccaggatact cagatgagta tgaagaagat
 901 ggattcgtc agccatacag agggattgca tgtgcaagat ttattggcaa ccgcaccgtc
 961 tatatggagt ctttgcacat gcaaggggaa ataaaaatc agatcacagc tgccttcact
1021 atgattggca cttccagtca cttatctgat aagtgttctc agttcgccat tccttccctg
1081 tgccactatg ccttcccgta ctgcgatgaa acttcatccg tcccaaagcc ccgtgacttg
1141 tgtcgcgatg aatgtgaaat cctgtgtgtc aaacagagta cattttgca
1201 agatcaaatc ccatgattct gatgaggctg aaactgccaa actgtgaaga tctcccccag
1261 ccagagagcc cagaagctgc gaactgtatc cggattggaa ttcccatggc agatcctata
1321 aataaaaatc acaagtgtta taacagcaca ggtgtggact acggggac cgtcagtgtg
1381 accaaatcag ggcgccagtg ccagccatgg aattcccagt atccccacac acacactttc
1441 accgccctc gtttcccaga gctgaatgga ggccattcct actgccgcaa cccagggaat
```

```
1501 caaaaggaag ctccctggtg cttcaccttg gatgaaaact ttaagtctga tctgtgtgac
1561 atcccagcgt gcgattcaaa ggattccaag gagaagaata aaatggaaat cctgtacata
1621 ctagtgccaa gtgtggccat tcccctggcc attgctttac tcttcttctt catttgcgtc
1681 tgtcggaata accagaagtc atcgtcggca ccagtccaga ggcaaccaaa acacgtcaga
1741 ggtcaaaatg tagagatgtc aatgctgaat gcatataaac ccaagagcaa ggctaaagag
1801 ctacctcttt ctgctgtacg ctttatggaa gaattgggtg agtgtgcctt tggaaaaatc
1861 tataaaggcc atctctatct cccaggcatg gaccatgctc agctggttgc tatcccctaatg
1921 ttgaaagact ataacaaccc ccagcaatgg acggaatttc aacaagaagc ctccctaatg
1981 gcagaactgc accacccaa tattgtctgc cttctaggtg ccgtcactca ggaacaacct
2041 gtgtcatgc tttttgagta tattaatcag gggatctcc atgagttcct catcatgaga
2101 tccccacact ctgatgttgg ctgcagcagt gatgaagatg ggactgtgaa atccagcctg
2161 gaccacggag attttctgca cattgcaatt cagattgcag ctggcatgga ataccttgtct
2221 agtcacttct ttgtccacaa ggaccttgca gctcgcaata tttttaatcgg agagcaactt
2281 catgtaaaga tttcagactt ggggctttcc agagaaattt actccgctga ttactacagg
2341 gtccagagta agtcctgct gccattcgc tggatgcccc ctgaagccat catgtatggc
2401 aaattctctt ctgattcaga tatctgtc tttggggttg tcttgtggga gattttcagt
2461 tttgactcc agccatatta tggattcagt aaccaggaag tgattgagat ggtgagaaaa
2521 cggcagctct taccatgctc tgaagactgc ccaccagaa tgtacagcct catgacagag
2581 tgctggaatg agattcctc taggagacca agatttaaag atattcacgt ccggcttcgg
2641 tcctgggagg gactctcaag tcacacaagc tctactactc cttcaggggg aaatgccacc
2701 acacagacaa cctccctcag tgccagccca gtgagtaatc tcagtaaccc cagatatcct
2761 aattacatgt tcccgagcca gggtattaca ccacagggcc agattgctgg tttcattggc
2821 ccgccaatac ctcagaacca gcgattcatt cccatcaatg gataccccat acctcctgga
2881 tatgcagcgt ttccagctgc ccactaccag ccaacaggtc ctcccagagt gattcagcac
2941 tgcccacctc ccaagagtcg gtccccaagc agtgccagtg ggtcgactag cactggccat
3001 gtgactagct tgccctcatc aggatccaat caggaagcaa atattcctt actaccacac
```

```
3061  atgtcaattc  caaatcatcc  tggtggaatg  ggtatcaccg  tttttggcaa  caaatctcaa
3121  aaaccctaca  aaattgactc  aaagcaagca  tctttactag  gagacgccaa  tattcatgga
3181  cacaccgaat  ctatgatttc  tgcagaactg  taaaatgcac  aactttgta   aatgtggtat
3241  acaggacaaa  ctagacggcc  gtagaaaaga  tttatattca  aatgttttta  ttaaagtaag
3301  gttctcattt  agcagacatc  gcaacaagta  ccttctgtga  agtttcactg  tgtcttacca
3361  agcaggacag  acactcggcc  ag
```

FIG. 19 (cont.)

```
  1 mhrprrrgtr ppllaliaal llaargaaaq etelsvsael vptsswniss elnkdsyltl
 61 depmnnitts lgqtaelhck vsgnppptir wfkndapvvq eprrlsfrst iygsrlrirn
121 ldttdtgyfq cvatngkevv sstgvlfvkf gppptaspgy sdeyeedgfc qpyrgiacar
181 fignrtvyme slhmqgeien qitaaftmig tsshlsdkcs qfaipslchy afpycdetss
241 vpkprdlcrd eceilenvlc qteyifarsn pmilmrlklp ncedlpqpes peaancirig
301 ipmadpinkn hkcynstgvd yrgtvsvtks grqcqpwnsq yphthtftal rfpelngghs
361 ycrnpgnqke apwcftlden fksdlcdipa cdskdskekn kmeilyilvp svaiplaial
421 lffficvcrn nqksssapvq rqpkhvrgqn vemsmlnayk pkskakelpl savrfmeelg
481 ecafgkiykg hlylpgmdha qlvaiktlkd ynnpqqwtef qqeaslmael hhpnivcllg
541 avtqeqpvcm lfeyinqgdl heflimrsph sdvgcssded gtvkssldhg dflhiaiqia
601 agmeylsshf fvhkdlaarn iligeqlhvk isdlglsrei ysadyyrvqs ksllpirwmp
661 peaimygkfs sdsdiwsfgv vlweifsfgl qpyygfsnqe viemvrkrql lpcsedcppr
721 myslmtecwn eipsrrprfk dihvrlrswe glsshtsstt psggnattqt tslsaspvsn
781 lsnprypnym fpsqgitpqg qiagflgppi pqnqrfipin gypipppgyaa fpaahyqptg
841 pprviqhcpp pksrspssas gststghvts lpssgsnqea nipllphmsi pnhpggmgit
901 vfgnksqkpy kidskqasll gdanihghte smisael
```

FIG. 20

| Tissue type | Tissue status | Histological type | ROR1 status | Total cases | Positive cases |
|---|---|---|---|---|---|
| Breast | Normal | | - | 4 | 0 |
| | Tumor | Ductal Carcinoma In Situ (DCIS) | + | 22 | 19 |
| | | Invasive (or Infiltrating) Ductal Carcinoma | + | 41 | 28 |
| | | Invasive (or Infiltrating) Lobular Carcinoma | + | 8 | 6 |
| | | invasive and in situ lobular ca | + | 2 | 2 |
| | | In Situ & Invas Ductal Carcinoma | + | 8 | 6 |
| | | Mammory cancer | + | 2 | 0 |
| | | High Grade Mammary Cancer | + | 1 | 1 |
| | | in situ papillary carcinoma | + | 2 | 2 |
| | | high gr pap adenocarcinoma | + | 2 | 1 |
| | | phyllodes tumor | + | 3 | 1 |
| | | Ductal & Lobular carcinoma | + | 2 | 2 |

FIG. 27

| Tissue type | Tissue status | Histological type | | ROR1 status | Total cases | Positive cases |
|---|---|---|---|---|---|---|
| Ovarian | normal | | | - | 8 | 0 |
| | Tumor | ovarian epithelial carcinoma (most) | Serous tumour/papillary | + | 18 | 16 |
| | | | Endometrioid tumor | + | 3 | 3 |
| | | | Mixed epithelial tumors | + | 3 | 3 |
| | | | Clear cell tumors | + | 4 | 4 |
| | | | Invas pap carcinoma | + | 9 | 9 |
| | | | Serous Cystadenoca | + | 3 | 2 |
| | | Sex cord-stromal tumor (8%) | Granulosa cell tumor | + | 4 | 4 |
| | | | Sertoli=leydig cell tumor/ arrhenoblastoma | + | 1 | 1 |

FIG. 28

| Tissue type | Tissue status | Histological type | ROR1 status | Total cases | Positive cases |
|---|---|---|---|---|---|
| Lung | Normal | | - | 9 | 0 |
| | Tumor | Squamous cell carcinoma | + | 29 | 18 |
| | | Adenocarcinoma | + | 30 | 28 |
| | | Large cell carcinoma | + | 2 | 2 |
| | | Combined | + | 11 | 9 |
| Skin | Normal | | - | 5 | 0 |
| | Tumor | Melenoma | + | 42 | 37 |
| | | Merkel Cell Carcinoma | + | 5 | 5 |
| | | Basal Cell Carcinoma | + | 4 | 3 |
| | | Squamous Cell Carcinoma | + | 7 | 7 |

FIG. 29

| Tissue type | Histological type | ROR1 status | Total cases | Positive cases |
|---|---|---|---|---|
| Bladder | Normal | | 4 | 0 |
| | transitional cell carcinoma | | 15 | 7 |
| | Invasice Transitional Cell Carcinoma | | 2 | 2 |
| | Squamous cell carcinoma | | 4 | 0 |
| | High grade papillary transitional cell carcinoma | | 2 | 0 |
| | Urothelial carcinoma | | 6 | 5 |
| | pap. urothelial carcinoma | | 2 | 0 |
| | small cell carcinoma | | 2 | 2 |
| | Invasive urethral carcinoma | | 3 | 1 |
| | Adenocarcinoma | | 2 | 0 |

FIG. 30

| Tissue type | Histological type | ROR1 status | Total cases | ROR1 +cases |
|---|---|---|---|---|
| Testicular | Normal | | 3 | 0 |
| | Seminoma | | 14 | 14 |
| | Teratoma | | 2 | 0 |
| | tertoma and embryonal carcinoma | | 2 | 0 |
| | Embryonal carcinoma | | 4 | 4 |
| | mixed germ cell | | 6 | 4 |

FIG. 31

| Tissue type | Histological type | Total cases | ROR1 + |
|---|---|---|---|
| Uterine | Normal | 1 | 0 |
| | Adenocarcinoma | 5 | 5 |
| | endometroid carcinoma | 7 | 7 |
| | carc sarcoma | 3 | 3 |
| | tumor | 5 | 5 |
| | carcinoma | 6 | 5 |

FIG. 32

| Tissue type | Histological type | ROR1 status | Total cases | Tissue type |
|---|---|---|---|---|
| Adrenal | Normal | | 2 | 0 |
| | Adrenocortical Carcinoma | | 2 | 0 |
| | Pheochromocytema | | 2 | 2 |
| | Fallicular Carcinoma With Minimal Capsular Invasion | | 2 | 2 |
| | Adrenal Cortial Neoplasm | | 2 | 2 |
| | Hurthle Cell Tumor, Borderline | | 2 | 2 |

FIG. 33

Table. ROR1 is present in additional tumors and absent in additional normal tissues

| Tissue type | Tissue status | ROR1 status | Total cases | Positive cases |
|---|---|---|---|---|
| Lymphoma | Tumor | + | 58 | 51 |
| Pancreas | Tumor | + | 50 | 44 |
| Penis | Tumor | + | 3 | 2 |
| Larynx | Tumor | + | 8 | 6 |
| Liver | Tumor | + | 17 | 16 |
| Parotid | Tumor | + | 6 | 4 |
| Sarcoma | Tumor | + | 22 | 16 |
| Thymus | Tumor | - | 2 | 0 |
| Gallbladder | Normal | - | 2 | 0 |
| Nevus | Normal | - | 1 | 0 |
| Dermat | Normal | - | 1 | 0 |
| Periph Nerve | Normal | - | 1 | 0 |
| Nevi | Normal | - | 1 | 0 |
| Vasculacture | Normal | - | 2 | 0 |
| Fallopian tube | Normal | - | 1 | 0 |
| Placenta | Normal | - | 2 | 0 |
| Spleen | Normal | - | 1 | 0 |
| Lymph node | Normal | - | 2 | 0 |

FIG. 34

| Tissue type | Tissue status | Histological type | ROR1 status | Total cases | Positive cases |
|---|---|---|---|---|---|
| Lymphoma | | Follicular lymphoma | | 10 | 10 |
| | | Diffuse large B cell | | 2 | 2 |
| | | Non Hodgkin lymphoma | | 6 | 6 |
| | | | | | |
| | | large B cell lymphoma | | 6 | 6 |
| | | Mantle cell lymphoma | | 2 | 2 |
| | | B cell | | 6 | 5 |
| | | Hodgkin lymphoma | | 8 | 7 |
| | | malignant lymphoma large CCH | | 2 | 2 |
| | | multiple confluent granulomas | | 2 | 2 |
| | | Small Cell Lymphoma | | 2 | 1 |

FIG. 35

SEQUENCE LISTING

<160> NUMBER OF SEQ ID NOS: 18

<210> SEQ ID NO 1
<211> LENGTH: 3382
<212> TYPE: DNA
<213> ORGANISM: Homo sapiens

<400> SEQUENCE: 1

```
gttgagcgag agagggagcg tggagagctg gagcagccgc caccgccgcc gccgagggag        60
ccccgggacg gcagcccctg ggcgcagggt gcgctgttct cggagtccga cccagggcga       120
ctcacgccca ctggtgcgac ccggacagcc tgggactgac ccgccggccc aggcgaggct       180
gcagccagag ggctgggaag ggatcgcgct cgcggcatcc agaggcggcc aggcggaggc       240
gagggagcag gttagaggga caaagagctt tgcagacgtc cccggcgtcc tgcgagcgcc       300
agcggccggg acgaggcggc cgggagcccg ggaagagccc gtggatgttc tgcgcgcggc       360
ctgggagccg ccgccgccgc cgcctcagcg agaggaggaa tgcaccggcc gcgccgccgc       420
gggacgcgcc cgccgctcct ggcgctgctg gccgcgctgc tgctggccgc acgcggggct       480
gctgcccaag aaacagagct gtcagtcagt gctgaattag tgcctacctc atcatggaac       540
atctcaagtg aactcaacaa agattcttac ctgaccctcg atgaaccaat gaataacatc       600
accacgtctc tgggccagac agcagaactg cactgcaaag tctctgggaa tccacctccc       660
accatccgct ggttcaaaaa tgatgctcct gtggtccagg agcccggag gctctccttt       720 cggtccacca tctatggctc tcggctgcgg attagaaacc tcgacaccac agacacaggc       780
tacttccagt gcgtggcaac aaacggcaag gaggtggttt cttccactgg agtcttgttt       840
gtcaagtttg gccccctcc cactgcaagt ccaggatact cagatgagta tgaagaagat       900
ggattctgtc agccatacag agggattgca tgtgcaagat ttattggcaa ccgcaccgtc       960
tatatggagt ctttgcacat gcaagggaa atagaaaatc agatcacagc tgccttcact      1020
atgattggca cttccagtca cttatctgat aagtgttctc agttcgccat tccttccctg      1080
```

```
tgccactatg ccttcccgta ctgcgatgaa acttcatccg tcccaaagcc ccgtgacttg   1140
tgtcgcgatg aatgtgaaat cctggagaat gtcctgtgtc aaacagagta cattttttgca  1200 agatcaaatc ccatgattct gatgaggctg aaactgccaa actgtgaaga tctcccccag   1260
ccagagagcc cagaagctgc gaactgtatc cggattggaa ttcccatggc agatcctata   1320
aataaaaatc acaagtgtta taacagcaca ggtgtggact accgggggac cgtcagtgtg   1380
accaaatcag ggcgccagtg ccagccatgg aattcccagt atccccacac acacactttc   1440 accgccttc gtttcccaga gctgaatgga ggccattcct actgccgcaa cccagggaat    1500
caaaaggaag ctccctggtg cttcaccttg gatgaaaact ttaagtctga tctgtgtgac   1560
atcccagcgt gcgattcaaa ggattccaag gagaagaata aaatgaaaat cctgtacata   1620
ctagtgccaa gtgtggccat tccctggcc attgctttac tcttcttctt catttgcgtc    1680
tgtcggaata accagaagtc atcgtcggca ccagtccaga ggcaaccaaa acacgtcaga   1740
ggtcaaaatg tagagatgtc aatgctgaat gcatataaac ccaagagcaa ggctaaagag   1800
ctacctcttt ctgctgtacg ctttatggaa gaattgggtg agtgtgcctt tggaaaaatc   1860
tataaaggcc atctctatct cccaggcatg gaccatgctc agctggttgc tatcaagacc   1920
ttgaaagact ataacaaccc ccagcaatgg acggaatttc aacaagaagc ctccctaatg   1980
gcagaactgc accaccccaa tattgtctgc cttctaggtg ccgtcactca ggaacaacct   2040
gtgtgcatgc tttttgagta tattaatcag ggggatctcc atgagttcct catcatgaga   2100
tccccacact ctgatgttgg ctgcagcagt gatgaagatg ggactgtgaa atccagcctg   2160
gaccacggag attttctgca cattgcaatt cagattgcag ctggcatgga atacctgtct   2220
agtcacttct ttgtccacaa ggaccttgca gctcgcaata ttttaatcgg agagcaactt   2280
catgtaaaga tttcagactt ggggctttcc agagaaattt actccgctga ttactacagg   2340
gtccagagta agtccttgct gcccattcgc tggatgcccc ctgaagccat catgtatggc   2400
aaattctctt ctgattcaga tatctggtcc tttggggttg tcttgtggga ttttcagt     2460 tttggactcc agccatatta tggattcagt aaccaggaag tgattgagat ggtgagaaaa   2520
cggcagctct accatgctc tgaagactgc ccacccagaa tgtacagcct catgacagag    2580
tgctggaatg agattccttc taggagacca agatttaaag atattcacgt ccggcttcgg   2640
tcctgggagg gactctcaag tcacacaagc tctactactc cttcagggg aaatgccacc    2700 acacagacaa cctccctcag tgccagccca gtgagtaatc tcagtaaccc cagatatcct   2760
aattacatgt tcccgagcca gggtattaca ccacagggcc agattgctgg tttcattggc   2820
ccgccaatac ctcagaacca gcgattcatt cccatcaatg gatacccaat acctcctgga   2880
tatgcagcgt ttcagctgc ccactaccag ccaacaggtc ctcccagagt gattcagcac    2940 tgccccacctc ccaagagtcg gtccccaagc agtgccagtg ggtcgactag cactggccat  3000
gtgactagct tgccctcatc aggatccaat caggaagcaa atattccttt actaccacac   3060
atgtcaattc caaatcatcc tggtggaatg ggtatcaccg tttttggcaa caaatctcaa   3120
aaaccctaca aaattgactc aaagcaagca tctttactag gagacgccaa tattcatgga   3180
cacaccgaat ctatgatttc tgcagaactg taaaatgcac aacttttgta aatgtggtat   3240
acaggacaaa ctagacggcc gtagaaaaga tttatattca aatgttttta ttaaagtaag   3300
gttctcattt agcagacatc gcaacaagta ccttctgtga agtttcactg tgtcttacca   3360
agcaggacag acactcggcc ag                                            3382
```

```
<210> SEQ ID NO 2
<211> LENGTH: 937
<212> TYPE: PRT
<213> ORGANISM: Homo sapiens

<400> SEQUENCE: 2

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
```

```
            385                 390                 395                 400
Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
    530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
    610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
    690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
    770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815
```

```
Ile Pro Ile Asn Gly Tyr Pro Ile Pro Pro Gly Tyr Ala Ala Phe Pro
             820                 825                 830

Ala Ala His Tyr Gln Pro Thr Gly Pro Pro Arg Val Ile Gln His Cys
         835                 840                 845

Pro Pro Pro Lys Ser Arg Ser Pro Ser Ser Ala Ser Gly Ser Thr Ser
 850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                 885                 890                 895

Met Gly Ile Thr Val Phe Gly Asn Lys Ser Gln Lys Pro Tyr Lys Ile
             900                 905                 910

Asp Ser Lys Gln Ala Ser Leu Leu Gly Asp Ala Asn Ile His Gly His
         915                 920                 925

Thr Glu Ser Met Ile Ser Ala Glu Leu
     930                 935

<210> SEQ ID NO 3
<211> LENGTH: 292
<212> TYPE: DNA
<213> ORGANISM: Human
<220> FEATURE:
<221> NAME/KEY: misc_feature
<222> LOCATION: (169)..(169)
<223> OTHER INFORMATION: n is a, c, g, or t

<400> SEQUENCE: 3
gaagtgaaac tggtggagtc tgggggaggc ttagtgaagc ctggagggtc cctgaaactc      60
tcctgtgcag cctctggatt cactttcagt agctatgcca tgtcttgggt tcgccagatt     120
ccagagaaga ggctggagtg ggtcgcatcc attagtcgtg gtggtaccna cctactatcc     180
agacagtgtg aagggccgat tcaccatctc cagagataat gtcaggaaca tcctgtacct     240
gcaaatgagc agtctgaggt ctgaggacac ggccatgtat tactgtggaa ga             292

<210> SEQ ID NO 4
<211> LENGTH: 15
<212> TYPE: DNA
<213> ORGANISM: Human

<400> SEQUENCE: 4
tatgattacg acggg                                                       15

<210> SEQ ID NO 5
<211> LENGTH: 51
<212> TYPE: DNA
<213> ORGANISM: Human

<400> SEQUENCE: 5
tactatgcaa tggactactg gggtcaagga acctcagtca ccgtctcctc a               51

<210> SEQ ID NO 6
<211> LENGTH: 284
<212> TYPE: DNA
<213> ORGANISM: Human

<400> SEQUENCE: 6
gacatcaaga tgacccagtc tccatcttcc atgtatgcat ctctaggaga gagagtcact      60
atcacttgca aggcgagtcc ggacattaat agctatttaa gctggttcca gcagaaacca     120
gggaaatctc ctaagaccct gatctatcgt gcaaacagat tggttgatgg ggtcccatca     180
```

```
aggttcagtg gcggtggatc tgggcaagat tattctctca ccatcaacag cctggagtat        240
gaagatatgg gaatttatta ttgtctacag tatgatgaat ttcc                         284
```

<210> SEQ ID NO 7
<211> LENGTH: 38
<212> TYPE: DNA
<213> ORGANISM: Human

<400> SEQUENCE: 7

```
gtacacgttc ggaggggga ccaagctgga atgaaac                                   38
```

<210> SEQ ID NO 8
<211> LENGTH: 221
<212> TYPE: DNA
<213> ORGANISM: Human
<220> FEATURE:
<221> NAME/KEY: misc_feature
<222> LOCATION: (2)..(2)
<223> OTHER INFORMATION: n is a, c, g, or t

<400> SEQUENCE: 8

```
antttcgtca gactttgacc ggtaaaacca taacattgga agttgaatct tccgatacca         60
tcgacaacgt taagtcgaaa attcaagaca aggaaggtat ccctccagat caacaaagat        120
tgatctttgc cggtaagcag ctagaagacg gtagaacgct gtctgattac aacattcaga        180
aggagtccac cttacatctt gtgctaaggc taagaggtgg t                            221
```

<210> SEQ ID NO 9
<211> LENGTH: 141
<212> TYPE: DNA
<213> ORGANISM: Human

<400> SEQUENCE: 9

```
cacggatccg gagcttggct gttgcccgtc tcactggtga aaagaaaaac caccctggcg         60
cccaatacgc aaaccgcctc tccccgcgcg ttggccgatt cattaatgca gctggcacga        120
caggtttccc gaagcggccg c                                                  141
```

<210> SEQ ID NO 10
<211> LENGTH: 2814
<212> TYPE: DNA
<213> ORGANISM: Human

<400> SEQUENCE: 10

```
atgcaccggc cgcgccgccg cgggacgcgc ccgccgctcc tggcgctgct ggccgcgctg         60
ctgctggccg cacgcggggc tgctgcccaa gaaacagagc tgtcagtcag tgctgaatta        120
gtgcctacct catcatggaa catctcaagt gaactcaaca agattcttac ctgaccctt         180 gatgaaccaa tgaataacat caccacgtct ctgggccaga cagcagaact gcactgcaaa        240
gtctctggga tccacctcc caccatccgc tggttcaaaa atgatgctcc tgtggtccag        300
gagccccgga ggctctcctt tcggtccacc atctatggct ctcggctgcg gattagaaac        360
ctcgacacca cagacacagg ctacttccag tgcgtggcaa caacggcaa ggaggtggtt        420 tcttccactg gagtcttgtt tgtcaagttt ggccccccctc ccactgcaag tccaggatac        480
tcagatgagt atgaagaaga tggattctgt cagccataca gagggattgc atgtgcaaga        540
tttattggca accgcaccgt ctatatggag tctttgcaca tgcaagggga aatagaaaat        600
cagatcacag ctgccttcac tatgattggc acttccagtc acttatctga taagtgttct        660
cagttcgcca ttccttccct gtgccactat gccttcccgt actgcgatga aacttcatcc        720
```

```
gtcccaaagc cccgtgactt gtgtcgcgat gaatgtgaaa tcctggagaa tgtcctgtgt    780
caaacagagt acattttttgc aagatcaaat cccatgattc tgatgaggct gaaactgcca    840
```

```
gtcccaaagc cccgtgactt gtgtcgcgat gaatgtgaaa tcctggagaa tgtcctgtgt    780
caaacagagt acattttgc  aagatcaaat cccatgattc tgatgaggct gaaactgcca    840
aactgtgaag atctccccca gccagagagc ccagaagctg cgaactgtat ccggattgga    900
attcccatgg cagatcctat aaataaaaat cacaagtgtt ataacagcac aggtgtggac    960
taccggggga ccgtcagtgt gaccaaatca gggcgccagt gccagccatg gaattcccag   1020
tatccccaca cacacacttt caccgcccct cgtttcccag agctgaatgg aggccattcc   1080
tactgccgca acccagggaa tcaaaaggaa gctccctggt gcttcacctt ggatgaaaac   1140
tttaagtctg atctgtgtga catcccagct tgcgattcaa aggattccaa ggagaagaat   1200
aaaatggaaa tcctgtacat actagtgcca agtgtggcca ttcccctggc cattgcttta   1260
ctcttcttct tcatttgcgt ctgtcggaat aaccagaagt catcgtcggc accagtccag   1320
aggcaaccaa aacacgtcag aggtcaaaat gtggagatgt caatgctgaa tgcatataaa   1380
cccaagagca aggctaaaga gctacctctt tctgctgtac gctttatgga agaattgggt   1440
gagtgtgcct ttggaaaaat ctataaaggc catctctatc tcccaggcat ggaccatgct   1500
cagctggttg ctatcaagac cttgaaagac tataacaacc cccagcaatg gatgaatttt   1560
caacaagaag cctccctaat ggcagaactg caccaccccca atattgtctg ccttctaggt   1620
gccgtcactc aggaacaacc tgtgtgcatg cttttttgagt atattaatca ggggatctc    1680
catgagttcc tcatcatgag atccccacac tctgatgttg gctgcagcag tgatgaagat   1740
gggactgtga atccagcct ggaccacgga gattttctgc acattgcaat tcagattgca   1800
gctggcatgg aatacctgtc tagtcacttc tttgtccaca aggaccttgc agctcgcaat   1860
attttaatcg gagagcaact tcatgtaaag atttcagact tggggctttc cagagaaatt   1920
tactccgctg attactacag ggtccagagt aagtccttgc tgcccattcg ctggatgccc   1980
cctgaagcca tcatgtatgg caaattctct tctgattcag atatctggtc ctttggggtt   2040
gtcttgtggg agattttcag ttttggactc cagcccatatt atggattcag taaccaggaa   2100
gtgattgaga tggtgagaaa acggcagctc ttaccatgct ctgaagactg cccacccaga   2160
atgtacagcc tcatgacaga gtgctggaat gagattcctt ctaggagacc aagatttaaa   2220
gatattcacg tccggcttcg gtcctgggag ggactctcaa gtcacacaag ctctactact   2280
ccttcagggg gaaatgccac cacacagaca acctccctca gtgccagccc agtgagtaat   2340
ctcagtaacc ccagatatcc taattacatg ttcccgagcc agggtattac accacagggc   2400
cagattgctg gtttcattgg cccgccaata cctcagaacc agcgattcat tcccatcaat   2460
ggatacccaa tacctcctgg atatgcagcg tttccagctg cccactacca gccaacaggt   2520
cctcccagag tgattcagca ctgcccacct cccaagagtc ggtccccaag cagtgccagt   2580
gggtcgacta gcactggcca tgtgactagc ttgccctcat caggatccaa tcaggaagca   2640
aatattcctt tactaccaca catgtcaatt ccaaatcatc ctggtggaat gggtatcacc   2700
gttttttggca acaaatctca aaaccctac  aaaattgact caaagcaagc atctttacta   2760
ggagacgcca atattcatgg acacaccgaa tctatgattt ctgcagaact gtaa          2814
```

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
cgagaggagg aatgcac                                                          17

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ataccacatt tacaaaagtt gtg                                                   23

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
attaagccca ggagttgc                                                         18

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
gaaagtcctg ccagttgg                                                         18

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
gaaggtgaag gtcggagtc                                                        19

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gaagatggtg atgggatttc                                                       20

<210> SEQ ID NO 17
<211> LENGTH: 21
<212> TYPE: DNA
<213> ORGANISM: Homo sapiens

<400> SEQUENCE: 17
atccggattg gaattcccat g                                                     21

<210> SEQ ID NO 18
<211> LENGTH: 19
<212> TYPE: DNA
<213> ORGANISM: Artificial Sequence
<220> FEATURE:
<223> OTHER INFORMATION: Synthetic construct -continued

```
<400> SEQUENCE: 18
agcggactaa gtccattgc                                              19
```

METHODS AND COMPOUNDS FOR LYMPHOMA CELL DETECTION AND ISOLATION

CROSS REFERENCE TO RELATED APPLICATIONS

This application is a Continuation-in-Part Application of International Application No. PCT/US2008/054613 filed Feb. 21, 2008, now abandoned; which claims the benefit under 35 USC §119(e) to U.S. application Ser. No. 60/971,818 filed Sep. 12, 2007, now abandoned and the benefit under 35 USC §120 to U.S. application Ser. No. 11/709,917, filed Feb. 21, 2007, now abandoned; which is a Continuation-in-Part Application of International Application No. PCT/US2006/042689 filed Oct. 30, 2006, now abandoned; which claims the benefit under 35 USC §119(e) to U.S. application Ser. No. 60/731,210 filed Oct. 28, 2005, now abandoned; and this application claims the benefit under 35 USC §119(e) to U.S. application Ser. No. 61/099,149 filed Sep. 22, 2008; abandoned.

GRANT INFORMATION

This invention was made with government support under Grant No. 5P01 CA81534 awarded by the National Institutes of Health. The government has certain rights in the invention.

BACKGROUND OF THE INVENTION

1. Field of the Invention

The present invention generally relates to chronic lymphocytic leukemia (CLL) detection, prevention and therapy and more specifically to antibodies directed against antigens specific for CLL, gene therapy for CLL, and inhibition of ROR1 expression and activity.

2. Background Information

Patients with cancer can develop immune responses against tumor-associated antigens (TAAs) and potentially reject autologous tumor. Many such TAAs represent developmental or differentiation antigens that have restricted expression. Conceivably, chronic lymphocytic leukemia (CLL) also might have such leukemia-associated antigens (LAA). Microarray analyses revealed that there are genes expressed by CLL cells that are not expressed in other lymphoid tissues. Coupled with the observation that CLL cells also express a highly restricted immunoglobulin repertoire, cells likely express distinctive antigens that also could be targeted for immunotherapy. However, CLL patients typically develop hypogammmaglobulinemia and worsening immune deficiency, which impairs their immune response to vaccines. Implicated in the abnormal immune function are immune-suppressive factors and an acquired functional deficiency of CD154. Furthermore, CLL cells are particularly poor at antigen presentation, which appears in part secondary to inadequate leukemia-cell expression of immune co-stimulatory/adhesion molecules.

Activation of CLL cells via CD40-ligation can reverse its immune-suppressive phenotype. Furthermore, CLL cells transduced with an adenovirus encoding the ligand for CD40 (Ad-CD154) can function as more effective antigen-presenting cells (APCs). In addition, they can effect ligation of CD40 on bystander leukemia B cells and stimulate autologous leukemia-reactive T cells both in vitro and in vivo.

Tyrosine kinases are important mediators of the signaling cascade, determining key roles in diverse biological processes like growth, differentiation, metabolism and apoptosis in response to external and internal stimuli. Studies have implicated the role of tyrosine kinases in the pathophysiology of cancer. Schlessinger J. (2000) Cell, 103:211-225; and Robinson et al. (2000) Oncogene, 19:5548-5557. MacKeigan and colleagues used a large-scale RNAi approach to identify kinases that might regulate survival and apoptosis of a human tumor cell line (HeLa), RNAi to ROR1 was found as one of the most potent in inducing apoptosis among the set of RNAi targeting each of 73 different kinase-encoding genes. MacKeigan et al. (2005) Nat Cell Biol., 7:591-600. However, these investigators did not examine the expression or function of ROR1 protein in these cells.

ROR1 is a membrane-receptor with an intracellular kinase-like domain and extracellular Frizzled-like cysteine-rich domain, which is common to receptors of members of the Wnt-family. ROR1 is member of the ROR family that is evolutionarily conserved among Caenorhavditis elegans, Drosophila, mice and humans. Wilson C, Goberdhan D C, Steller H. Dror, a potential neurotrophic receptor gene, encodes a Drosophila homolog of the vertebrate Ror family of Trk-related receptor tyrosine kinases. Proc Natl Acad Sci USA. 1993; 90:7109-7113; Oishi et al. (1997) J Biol. Chem., 272:11916-11923; Masiakowski et al. (1992) J Biol. Chem., 267:26181-26190; Forrester et al. (2002) Cell Mol Life Sci., 59:83-96; and Oishi et al. (1999) Genes Cells, 4:41-56. In rodents, ROR1 is expressed primarily in developing cephalic neural crest in the dorsal part of the diencephalons and mid-hind brain boundary during embryogenesis. In most species examined, expression of ROR1 apparently attenuates during embryonic development, becoming negligible at term. ROR1 mRNA was reported to express in infant brain, renal cancer and colon cancer. In a recent study, it was found that ROR1, at both mRNA and protein level, was highly expressed in CLL B cells but not normal B cells. Moreover, it was found that ROR1 is a receptor for Wnt5a, which could induce activation of NF-κB when co-expressed with ROR1 in HEK293 cells and enhance survival of CLL cells in vitro. This indicates that ROR1 is a CLL survival-signaling receptor for Wnt5a, however direct evidence of ROR1 effect on CLL progression is required. Another study found that ROR1 was expressed in acute lymphocytic leukemia (ALL) as well. Shabani et al. (2007) Tumour Biol., 28:318-326; and Baskar et al. (2008) Clin Cancer Res., 14:396-404. However, ROR1 expression on development and progression of other cancers has not yet been extensively explored, and therapeutic control of ROR1 expression is necessary.

As discussed above, ROR1 is an embryonic protein that is expressed uniquely on certain cancer cells, including in CLL, small lymphocytic lymphoma, marginal cell B-Cell lymphoma, Burkett's Lymphoma, and other cancers (e.g., breast cancers), but not on normal adult tissues and cells. Anti-ROR1 antibodies raised against ROR1 peptide are commercially available, but monoclonal anti-ROR1 antibodies that react with the native ROR1 protein have not been made or isolated. In addition, no anti-ROR1 antibodies capable of detecting cell-surface expression of ROR1 for flow cytometric analysis have been made or isolated. The antibody that can react with native ROR1 protein are also necessary.

SUMMARY OF THE INVENTION

Among the various aspects of the present invention is the provision of an antibody directed to a surface receptor tyrosine kinase protein expressed on cells found in samples of subjects with a cancer, including lymphomas, CLL, small lymphocytic lymphoma, marginal cell B-Cell lymphoma, Burkett's Lymphoma, renal cell carcinoma, colon cancer, colorectal cancer, and breast cancer, but not in blood or splenic lymphocytes of nonleukemic patients or normal adults.

Briefly, therefore, the present invention is directed to an antibody useful for differentiation between ROR1 expressing cancer cells ("ROR1 cancer") and normal cells as well as immunotherapy against ROR1 cancers and determination of response to cancer therapy.

The present invention includes compositions that include a purified, isolated antibody that binds specifically to ROR1 receptor protein.

The present invention includes methods for an immunoassay that detects ROR1 in a sample from a subject by contacting the sample with a ROR1-specific antibody and detecting immunoreactivity between the antibody and ROR1 in the sample.

In accordance with a further aspect of the invention, a ROR1 cancer is diagnosed in a subject by detecting the presence or quantity of ROR1 protein in a sample derived from the subject.

In accordance with yet another aspect of the invention, a ROR1 cancer is treated in a subject by administering to the subject in need of such therapy a therapeutically effective amount of a ROR1 receptor antagonist.

In accordance with yet another aspect, the appearance, status, course, or treatment of a ROR1 cancer in a subject is evaluated by contacting a biological sample obtained from the subject with an anti-ROR1 antibody and detecting immunoreactivity between the antibody and ROR1 to determine presence or quantity of ROR1 in the sample.

In accordance with yet another aspect, also provided is a vaccine composition comprising a polynucleotide encoding ROR1 protein or a fragment or variant thereof, and a pharmaceutically acceptable carrier or diluent.

In accordance with yet another aspect, also provided is a vaccine composition comprising ROR1 protein or a fragment or variant thereof, and a pharmaceutically acceptable carrier or diluent.

In accordance with yet another aspect, also provided is a method for protecting against the occurrence of diseases involving expression of ROR1 in a subject, the method comprising administering to the subject in need thereof a polynucleotide encoding ROR1 protein or a fragment or variant thereof in an amount effective to induce a protective or therapeutic immune response against ROR1, and a pharmaceutically acceptable carrier or diluent.

In accordance with yet another aspect, also provided is a method for protecting against the occurrence of diseases involving expression of ROR1 in a subject, the method comprising administering to the subject in need thereof ROR1 protein or a fragment or variant thereof in an amount effective to induce a protective or therapeutic immune response against ROR1 in the subject, and a pharmaceutically acceptable carrier or diluent.

In accordance with yet another aspect, a humanized ROR1 antibody is provided. In another aspect, a precipitate comprising a ROR1 antibody bound with a ROR1 protein, fragment or variant is provided. The ROR1 antibody can be conjugated to a magnetic bead.

The present invention is also directed toward a method for treating cancer in a subject by administering to the subject a therapeutically effective amount of a cell that expresses ROR1 protein, or a fragment thereof. In one aspect, the cancer is a lymphoma or adenocarcinoma. In another aspect, the lymphoma is selected from the group consisting of CLL, small lymphocytic lymphoma, marginal cell B-Cell lymphoma, and Burkett's Lymphoma, colon adenocarcinoma, and breast adenocarcinoma.

In another aspect, the cell transfected with the nucleic acid sequence of SEQ ID NO: 1 is administered by injection, inhalation, orally, liposome, or retroviral vector. In yet another aspect, the invention is directed toward a composition comprising a cell transfected with the nucleic acid sequence of SEQ ID NO: 1.

The invention also provides a vaccine for the treatment or prevention of cancer in a subject which consists of a cell transfected with the nucleic acid sequence of SEQ ID NO: 1. In one aspect, the cancer is a lymphoma or adenocarcinoma. In another aspect, the lymphoma is selected from the group consisting of CLL, small lymphocytic lymphoma, marginal cell B-Cell lymphoma, and Burkett's Lymphoma, colon adenocarcinoma, and breast adenocarcinoma.

The present invention also provides for a method for treating cancer in a subject by administering to the subject a therapeutically effective amount of a cell transfected with the nucleic acid sequence of SEQ ID NO: 1, or a fragment thereof. In one aspect, the cancer is a lymphoma or adenocarcinoma. In another aspect, the lymphoma is selected from the group consisting of CLL, small lymphocytic lymphoma, marginal cell B-Cell lymphoma, and Burkett's Lymphoma, colon adenocarcinoma, and breast adenocarcinoma. In one aspect, the cell transfected with the nucleic acid sequence of SEQ ID NO: 1 is administered in an amount of (i) about 0.05 mg to about 2.5 mg; (ii) about 0.1 mg to about 1 mg; or (iii) about 0.3 mg to about 0.5 mg. In another aspect, the cell transfected with the nucleic acid sequence of SEQ ID NO: 1 is administered by injection, inhalation, orally, liposome, or retroviral vector.

The present invention also provides a method of treating or preventing cancer in a subject by administering to the subject a nucleic acid comprising the nucleotide sequence of SEQ ID NO:1. In one aspect, the nucleotide sequence is at least 12 nucleotides in length. In another aspect, the nucleotide sequence has at least 80% identity to SEQ ID NO: 1. In yet another aspect, the nucleotide sequence has at least 90% identity to SEQ ID NO: 1. In another aspect, the nucleotide sequence has at least 95% identity to SEQ ID NO: 1. In yet another aspect, the nucleotide sequence encodes an open reading frame. In another aspect, the open reading frame consisting of SEQ ID NO: 2.

Also provided in the present invention is an isolated antibody that specifically binds to a protein encoded by a nucleotide sequence of SEQ ID NO: 1. In one aspect, the antibody is a polyclonal antibody. In another aspect, the antibody is a monoclonal antibody.

The present invention also contemplates purified serum containing anti-sera that specifically bind to a protein encoded by a nucleotide sequence of SEQ ID NO: 1.

A method for treating or preventing cancer in a subject by administering to the subject in need thereof a therapeutically effective amount of an antagonist to Wnt5a binding of ROR1 protein, or a fragment thereof is also contemplated in the invention. In one aspect, the cancer is a lymphoma or adenocarcinoma. In another aspect, the lymphoma is selected from the group consisting of CLL, small lymphocytic lymphoma, marginal cell B-Cell lymphoma, and Burkett's Lymphoma, colon adenocarcinoma, and breast adenocarcinoma. In yet a further aspect, the lymphoma is CLL in which ROR1 interaction with or binding of Wnt5a confers a survival advantage that is at least partially, if not wholly, negated by administration of a ROR1 antagonist according to the invention; in particular, isolated ROR1 antibodies, or purified serum containing anti-sera that prevent Wnt5a binding by a protein encoded by a nucleotide sequence of SEQ ID NO: 1.

The present invention further contemplates a method for treating a ROR1 related cancer in a subject. The method includes administering to the subject in need thereof an agent that depletes, inhibits or reduces ROR1 expression or activity. In various embodiments the ROR1 related cancer is breast cancer, lung cancer, colon cancer, ovarian cancer, prostate cancer, skin cancer, bladder cancer, testicular cancer, pancreatic cancer, uterine cancer, adrenal cancer, penis cancer, larynx cancer, liver cancer, parotid cancer, sarcoma, and lymphoma. Examples of breast cancer that may be treated include ductal carcinoma or lobular carcinoma. Examples of lung cancer that may be treated include squamous cell cancer, non-small cell lung cancer, large cell lung cancer, or adenocarcinoma. Examples of bladder cancer that may be treated include bladder urothelial carcinoma, small cell carcinoma or transitional cell carcinoma. In one aspect, the agent is administered in an amount of (i) about 10 µg/day to about 3 mg/day; (ii) about 30 µg/day to about 300 µg/day; or (iii) about 100 µg/day. In a related aspect, the agent may be administered by injection, inhalation, orally, liposome, or retroviral vector. In an exemplary aspect, the agent is an oligonucleotide, such as an antisense nucleic acid or siRNA.

The invention further contemplates a method of monitoring a therapeutic regimen for treating a subject having or at risk of having an ROR1 cancer. The method includes determining a change in activity or expression of ROR1 protein as a result of the treatment or prevention of the cancer, thereby monitoring the therapeutic regimen in the subject.

The invention further contemplates a method for detecting minimal residual disease following treatment of a ROR1 cancer. The method includes comparing the expression or activity of ROR1 protein in a sample from the subject being treated for cancer with the expression or activity of ROR1 protein in a control sample, wherein greater expression of ROR1 protein in the subject's sample as compared to the control sample indicates that the subject has minimal residual disease.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A is a series of scatter and line plots showing total levels of IgG, IgA, and IgM. IgG, IgA, IgM blood concentrations, measured just prior to initiating Ad-CD154 therapy (PRE) and 2-4 week following the final treatment time point (POST). The dashed bar in each line graph indicates the minimum normal Ig concentration. The concentration range of normal Ig levels is shown to the left of the legend. FIG. 1B is a series of scatter and line plots showing antibody response to recombinant Ad-CD154. Anti-adenovirus antibodies were analyzed by an ELISA assay. Serial dilutions of patient serum before (dotted line) and after (filled line) treatment were incubated in 96 well plates coated with Ad-CD154. Bound adenovirus-specific antibody was then detected using AP-conjugated antibody specific for human Ig. FIG. 1C is a series of bar graphs showing change of antibody response against Adenovirus in serial samples. Anti-adenovirus antibodies were analyzed by an ELISA using anti-isotype specific secondary antibodies conjugated AP. The bar graphs represent the mean increase in adenovirus-specific antibody over the baseline pre-treatment antibody levels. FIG. 1D is a series of scatter and line plots showing anti-tetanus-toxin antibody response before and after Ad-CD154 treatment. ELISA assay was performed with purified tetanus toxin and sera from patients. Bound tetanus-specific antibody was detected using AP conjugated goat anti-human Ig antibody.

FIG. 2A is a series of histograms showing diluted serum from patient before (open histograms) or after (shaded histograms) treatment was incubated with PBMC from a CLL patient. FIG. 2B is a series of histograms showing diluted serum from patient before (open histograms) or after (shaded histograms) treatment incubated with PBMC from a healthy donor.

FIGS. 4A through 4D are a series of images depicting gels that show expression of ROR1 in CLL B cells. FIG. 4A are gel images of an immunoblot analysis of ROR1 protein. Total cell lysates of PBMC from CLL patients or healthy donor and those of splenocytes from CLL patients or idiopathic thrombocytopenia purpura patient were analyzed by immunoblot using rabbit anti-ROR1 antibody. FIG. 4B are gel images showing ROR1 expression in B cell lines. Immunoblot analysis of total cell lysates of B cell lines was performed. FIG. 4C shows production of mouse anti-ROR1 sera. CHO cells stained with PKH26 and were mixed with CHO transfected ROR1 cDNA (CHO-ROR1). Sera collected from mice before and after immunization with ROR1 cDNA were incubated with mixed CHO cells. Bound antibodies were detected by flow cytometry. FIG. 4D is a series of histograms showing flow cytometric analysis of expression of ROR1 on cell surface of CLL. PBMC from CLL patients and healthy donor were incubated antisera before (open histograms) and after (shaded histograms) DNA immunization.

FIGS. 5B and 5C are a series of histograms showing production of anti-ROR1 antibody detected by flow cytometric analysis. FIG. 5B shows results where CHO stained with PKH26 were mixed and incubated with serum from patient. APC conjugated anti-human Ig antibody was used for detection.

FIG. 6A is a series of gel images showing production of recombinant ROR1 protein. ROR1 extracellular region was fused with rabbit IgG Fc region in frame (ROR1rIg). Fused cDNA were transfected into CHO cells and secreted recombinant protein was immunoabsorbed using protein A sepharose. Absorbed protein was immunoblotted with goat anti-ROR1 antibody (R&D) or goat anti-rabbit Ig antibody. KSHV K8.1 protein fused with rabbit Fc region was also used for control. The purified recombinant ROR1 was visualized with GelCode blue stain reagent (Pierce) staining after SDS-PAGE. FIG. 6B is a series of line and scatter plots showing antibody reaction to ROR1 detected by ELISA. Diluted sera were reacted with coated ROR1rIg and bound antibody was detected by goat anti-human Ig antibody conjugated with HRP. FIG. 6C is a series of line and scatter plots showing antibody reaction to rabbit IgG detected by ELISA. Diluted sera were reacted with coated rabbit IgG and bound antibody was detected by goat anti-human Ig antibody conjugated with HRP.

FIG. 7A is a series of bar graphs showing the effect of ROR1 on LEF/TCF1, NF-AT, and AP-1 activity. HEK293 cells were transfected with indicated reporter construct and β-galactosidase vector along with expression vector of ROR1 and Wnt5a. FIG. 7B is a series of bar graphs showing the effect of ROR1 on NF-κB activity. HEK293 cells were transfected with NF-κB reporter construct and β-galactosidase vector along with expression vector of ROR, Wnt5a, Wnt3, Wnt5b and Wnt16. FIG. 7C is a series of gel images showing in vitro binding of ROR1 and Wnt5a. Conditioned medium of transfectant with Wnt5a tagged with HA was incubated with ROR1rIg or rabbit IgG. Immunoprecipitation and immunoblotting were done with indicated materials.

FIG. 8 is a series of histograms showing gated CLL patients and CD19+ and CD19+CD5+ cells.

FIG. 11 is a series of histograms showing gated CLL patients and CD19+ and CD19+CD5+ cells.

FIG. 19 depicts the nucleotide sequence of human ROR1 (SEQ ID NO: 1).

FIG. 20 depicts the protein sequence of human ROR1 (SEQ ID NO: 2).

FIG. 21A shows representative images of immunostaining with hematoxylin and 4A5 against ROR1 or IgG2b isotype for fresh frozen human breast normal and invasive ductal carcinoma tissues. ROR1 immunostaining is shown in red and the nuclear staining is in blue (hematoxylin). FIG. 21B shows immunoblotting analysis of human breast normal and cancer tissues for ROR1 expression. CHO-ROR1 serves as negative and positive control. β-actin served as loading control. FIG. 21C shows representative images of immunostaining with hematoxylin and 4A5 for paraffin-embedded breast, ovarian and lung normal and tumor tissues according to a multitest survey of tumor by tissue microarray analysis. ROR1 immunostaining is shown in red and the nuclear staining is in blue (hematoxylin). Scale bar, 35 μm. FIG. 21D shows a graph depicting the frequency of ROR1 positive cases in different tumor tissues (n=examined cases number for different tumors).

FIG. 22A shows histograms depicting the fluorescence of different cancer cell lines stained with 4A5 (open histograms) or an IgG2b isotype control antibody of irrelevant specificity (shaded histograms) by flow cytometry analysis. CHO and CHO-ROR1 serve as negative and positive controls. FIG. 22B shows immunohischemical analysis of ROR1 expression in MCF-7 and MDA-MB-231 cell lines with 4A5 or IgG2b isotype. $1 \times 10^8$ cells were fixed in formalin, embedded in paraffin and cut for slides. FIG. 22C shows immunoprecipitation of ROR1 from different cancer cell lines using 4A5. Different cell lysates were incubated with 4A5 mAb and *Staph* protein A. Immunoprecipitated complexes were loaded onto polyacrylamide gel and probed with anti-ROR1 antibody. CHO and CHO-ROR1 serve as negative and positive controls.

FIG. 23 illustrates ROR1 is involved in NF-κB signaling responsive to Wnt5a. FIG. 23A shows Wnt5a expression in several cancer cell lines by RT-PCR (upper panel) and immunoblot (lower panel). Glyceraldehyde 3-phosphate dehydrogenase (GAPDH) serves as an internal control for RT-PCR and β-actin serves as an internal control for immunoblot. FIG. 23B shows graphs depicting the increase of NF-κB signaling by ROR1 responsive to Wnt5a. MDA-MB-231 cells with low Wnt5a expression were transfected with NF-κB-luciferase and different amount of Wnt5a plasmids (left panel) or with NF-κB-luciferase and ROR1 and treated with L or L-Wnt5a conditional medium (right panel). FIG. 23C depicts ROR1 knockdown efficiency detected by immunoblot and cytometry. MDA-MB-231 cells were infected with lentivirus containing ROR1-shRNA or Ct-shRNA. After 48 hours, cells were harvested for detection of ROR1 protein. ROR1 protein expression was quantitated and normalized to β-Actin and relative value was expressed (upper panel). Histograms depict the fluorescence of cells expressed ROR1-shRNA and Ct-shRNA stained with 4A5 mAb or IgG2b isotype (lower panel). FIG. 23D shows graphs depicting knockdown of ROR1 protein decreased NF-κB signaling. 786-0 cells with high Wnt5a expression was transfected with NF-κB-luciferase and Ct-shRNA or ROR1-shRNA (left panel). MDA-MB-231 cells with low Wnt5a expression were transfected NF-κB-luciferase, Wnt5a and Ct-shRNA or ROR-shRNA (right panel). Cells were harvested after 48 hours transfection for luciferase assay. The reporter assay was performed in triplicate, and the data represent the means and standard deviations of three independent experiments after normalization to β-galactosidase activity.

FIG. 24A shows graphs depicting ROR1 expression in MDA-MB-231 cells after infection with ROR1-shRNA or Ct-shRNA lentivirus for 2 days. The upper cells were gated as indicated in the contour plot (left panel) and represent positive cells (RFP+) infected with ROR1-shRNA lentivirus. The lower cells are RFP negative cells (RFP−) representing cells without infection of lentivirus. ROR1 protein expression was analyzed by flow cytometry with 4A5 mAb. The histograms depict the fluorescence of RFP+ (right) and RFP− (middle) subpopulation of cells infected with ROR1-shRNA (shaded histogram) or Ct-shRNA (open histogram). FIG. 24B shows graphs depicting cell analysis after 2 days of infection with ROR1-shRNA and Ct-shRNA lentivirus, RFP-(left panel) and RFP+ (middle panel) MDA-MB-231 cells, for apoptosis. The histograms depict apoptotic cells from cells infected with ROR1-shRNA (open histograms) and Ct-shRNA (shaded histograms) lentivirus. Right panel provided statistical analysis for the percentage of apoptosis cells (*p<0.01, n=4). FIG. 24C depicts MDA-MB-231 cells infected with ROR1-shRNA and Ct-shRNA selected to make stable MDA-MB-231 cell lines with (shaded histogram) or without ROR1 expression (open histogram), ROR1 protein levels were analyzed by cytometry (left panel). Equal amount of MDA-MB-231 cells with or without ROR1 expression were seeded to 96 well plates and cell numbers were counted from three wells with CCK assay from day 1 to day 6 (middle panel). The data represent the mean±s.d. of three independent experiments. *p<0.05. The right panel shows a representative phase contrast micrographs of cell growth after 4 days in culture.

FIG. 25A shows a graph depicting tumor growth curves of MDA-MB-231 cell with Ct-shRNA or ROR1-shRNA transfectants in $Rag^{-/-}\gamma^{-/-}$ mice. Same number of MDA-MB-231 cells with Ct-shRNA or ROR1-shRNA transfectants were s.c. injected into $Rag^{-/-}\gamma^{-/-}$ mice at one flank, tumor was measured by caliper and tumor volumes were estimated using the formula: length×width$^2$×0.4. Each data point indicates mean value (±s.e.m) of tumor volumes. **p=0.004, *p<0.03, n=5-7. FIG. 25B shows a graph depicting tumor weights from $Rag^{-/-}\gamma^{-/-}$ mice injected with MDA-MB-231 cell with Ct-shRNA or ROR1-shRNA transfectants at day 48 after injection. *p<0.04, n=5-7. FIG. 25C shows expression of ROR1 protein in representative tumor tissues from mice by immunohistochemistry (scale bar, 35 μm). FIG. 25D shows a graph depicting tumor growth curves of MDA-MB-231 cell labeled with luciferase in $Rag^{-/-}\gamma^{-/-}$ mice. MDA-MB-231 cells with or without ROR1 expression were labeled with luciferase and s.c. injected into $Rag^{-/-}$ gamma$^{-/-}$ mice. Tumor volumes were estimated as above. FIG. 25E shows a comparison of tumor engraftment sizes at 3 and 6 weeks after mice injected with luciferase labeled MDA-MB-231 cells with or without ROR1 expression. Upper panel showed representative image of tumor engraftment. Lower panel showed the quantitation of luciferase signaling. *p<0.03 n=4.

FIG. 27 shows a table depicting ROR1 overexpression in various tumor tissues.

FIG. 28 shows a table depicting ROR1 overexpression in various tumor tissues.

FIG. 29 shows a table depicting ROR1 overexpression in various tumor tissues.

FIG. 30 shows a table depicting ROR1 overexpression in various tumor tissues.

FIG. 31 shows a table depicting ROR1 overexpression in various tumor tissues.

FIG. 32 shows a table depicting ROR1 overexpression in various tumor tissues.

FIG. 33 shows a table depicting ROR1 overexpression in various tumor tissues.

FIG. 34 shows a table depicting ROR1 overexpression in various tumor tissues.

FIG. 35 shows a table depicting ROR1 overexpression in various tumor tissues.

DETAILED DESCRIPTION OF THE INVENTION

Figure 1A:
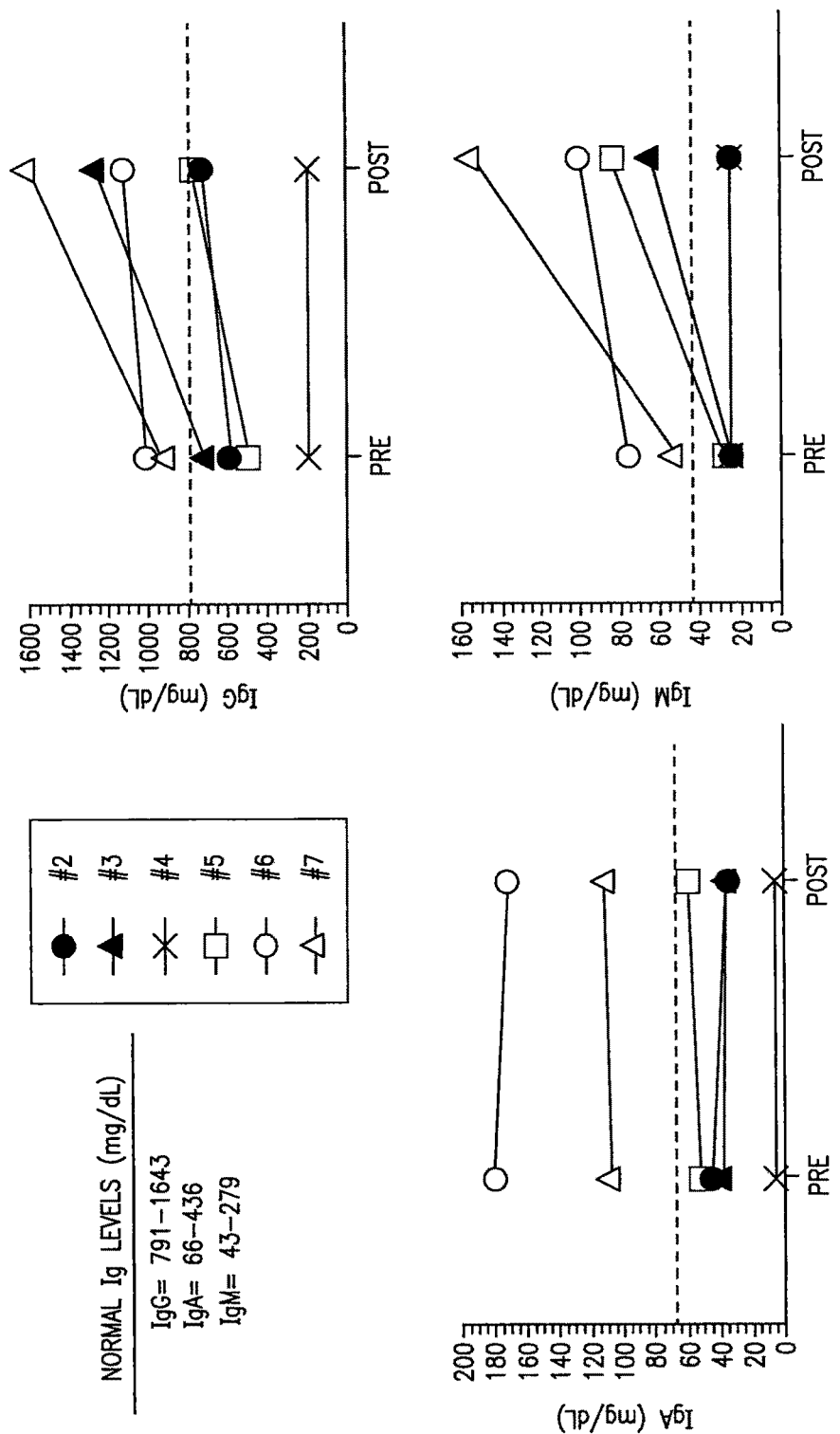
FIGS. 1A through 1D show change of serum antibody after Ad-CD154 therapy.

As noted above, the instant invention provides new and useful antibodies directed against ROR1 protein. Full length ROR1, a surface receptor tyrosine kinase, is found in samples of subjects with CLL, but not in blood or splenic lymphocytes of nonleukemic patients or normal adults. The invention also provides diagnostic and therapeutic antibodies, including monoclonal antibodies, and related compositions and methods for use in the diagnosis, management and treatment of disease. The ROR1 antibody described herein is more sensitive and more specific to ROR1 expressing cancer cells than using a combination of several cell surface markers that cannot exclude a small fraction of normal cells.

Additionally, the invention provides a vaccine for the treatment or prevention of cancer in a subject which consists of a cell transfected with the nucleic acid sequence of SEQ ID NO: 1. The invention also provides for a method for treating cancer in a subject by administering to the subject a therapeutically effective amount of a cell transfected with the nucleic acid sequence of SEQ ID NO: 1, or a fragment thereof. The present invention also provides a method of treating or preventing cancer in a subject by administering to the subject a nucleic acid comprising the nucleotide sequence of SEQ ID NO: 1. Also provided in the present invention is an isolated antibody that specifically binds to a protein encoded by a nucleotide sequence of SEQ ID NO: 1.

The present invention also provides purified serum with anti-sera that specifically bind to a protein encoded by a nucleotide sequence of SEQ ID NO: 1. Such human anti-sera were deposited on Sep. 14, 2007 pursuant to the Budapest Treaty on the International Deposit of Microorganisms for the Purposes of Patent Procedure with the Patent Culture Depository of the American Type Culture Collection, Manassas, Va., as Accession No. PTA-8634.

Applicants have discovered expression of full-length ROR1 in numerous cancer cell lines and samples, but not other tissues, including blood or splenic lymphocytes of non-leukemic patients or normal adult donors, and also generated mouse anti-sera against full-length human ROR1. Fukuda et al., Blood: ASH Annual Meeting Abstracts 2004 104, Abstract 772 (2004) (incorporated herein by reference in its entirety). The polypeptide and coding sequences for ROR1 have been reported elsewhere and are also incorporated herein by this reference (see, e.g., Accession Nos. NP_005003.2 and NM_005012). Surprisingly, it has also been discovered that cancer cells which express the Wnt5a protein, such as CLL cells, not only bind ROR1 but have a survival advantage conferred as a consequence. The invention therefore provides means to utilize the specificity of ROR1 expression in cancer cells, as well as knowledge of the interaction between Wnt5a and ROR1, to treat or prevent cancer.

In the latter respect, patients with CLL typically develop disease-related hypogammaglobulinemia and respond poorly to vaccines. The progressive acquired immune deficiency associated with CLL accounts for much of the morbidity related to this disease. However, as shown in the Examples, following treatment with autologous Ad-CD154-transduced CLL cells, most patients had increased serum IgM and IgG and developed a specific antibody response against adenovirus and some developed anti-CLL autoantibodies. Although virus infections occasionally can induce autoantibodies, autoantibodies were not detected against other blood cells or human CD154. Likewise, there were no increases in the titer of antibodies to a recall antigen, tentanus toxoid, except in one patient (#5) who was immunized with tetanus toxoid following the second infusion of autologous Ad-CD154-CLL cells. Conceivably, CLL patients could respond well against other vaccines administered during the course of such treatment, potentially allowing for generation of protective immunity against infectious agents that commonly afflict patients with this disease.

As shown in the examples, that some patients developed IgG anti-CLL autoantibodies, which reacted with ROR1. These post-treatment antisera reacted with a protein of ~125 kD found in lysates of CLL cells or CHO-ROR1 cells, but not in lysates prepared from human blood lymphocytes of normal donors or non-transfected CHO cells. That these antisera reacted with ROR1 was corroborated via ELISA using a recombinant ROR1 fusion-protein. Because these antisera appeared specific for CLL cells, the expression of ROR1 on other adult tissues was studied. These studies revealed that expression of the ROR1 protein was restricted to CLL B-cells and was not found on the non-leukemic blood or marrow mononuclear cells of patients with CLL, potentially allowing for detection of CLL cells in the blood or marrow of patients with early-stage disease or minimal residual disease after therapy. Furthermore, ROR1 was not found on normal adult tissues or lymphoid cells, including CD5-positive B cells. As such, ROR1 appears to represent a specific leukemia-associated antigen. The selective expression of ROR1 in CLL suggests that ROR1 factors in the pathogenesis of this disease.

ROR1 encodes a type I membrane receptor tyrosine kinase that initially was identified using oligonucleotide primers targeting sequences encoding amino acid sequences common to tyrosine kinase domains of different proteins. This protein appears highly conserved throughout evolution. ROR1 is evolutionary conserved among *Caenorhabditis elegans* (*C. elegans*), Aplysia, *Drosophila melanogaster, Xenopus,* mice, and humans. In rodents, ROR1 is expressed primarily in developing cephalic neural crest in the dorsal part of the diencephalons and mid-hind brain boundary during embryogenesis. Work in *Caenorhabditis elegans* (*C. elegans*) indicated that the RORI-type kinases might be involved in the regulation of cell motility and in asymmetric cell division during embryogenesis.

Furthermore, the ROR protein in *C. elegans,* apparently has both kinase-dependent and kinase independent ROR-family receptor tyrosine kinases are characterized by the intracellular tyrosine kinase domains, highly related to those of the Trk-family receptor tyrosine kinases, and by the extracellular Frizzled-like cysteine-rich domains and kringle domains, which are common to receptors of the Wnt-family members. An ortholog to ROR1, namely ROR2, has been found interact physically with Wnt5a to activate non-canonical Wnt-signaling.

Figure 6B:
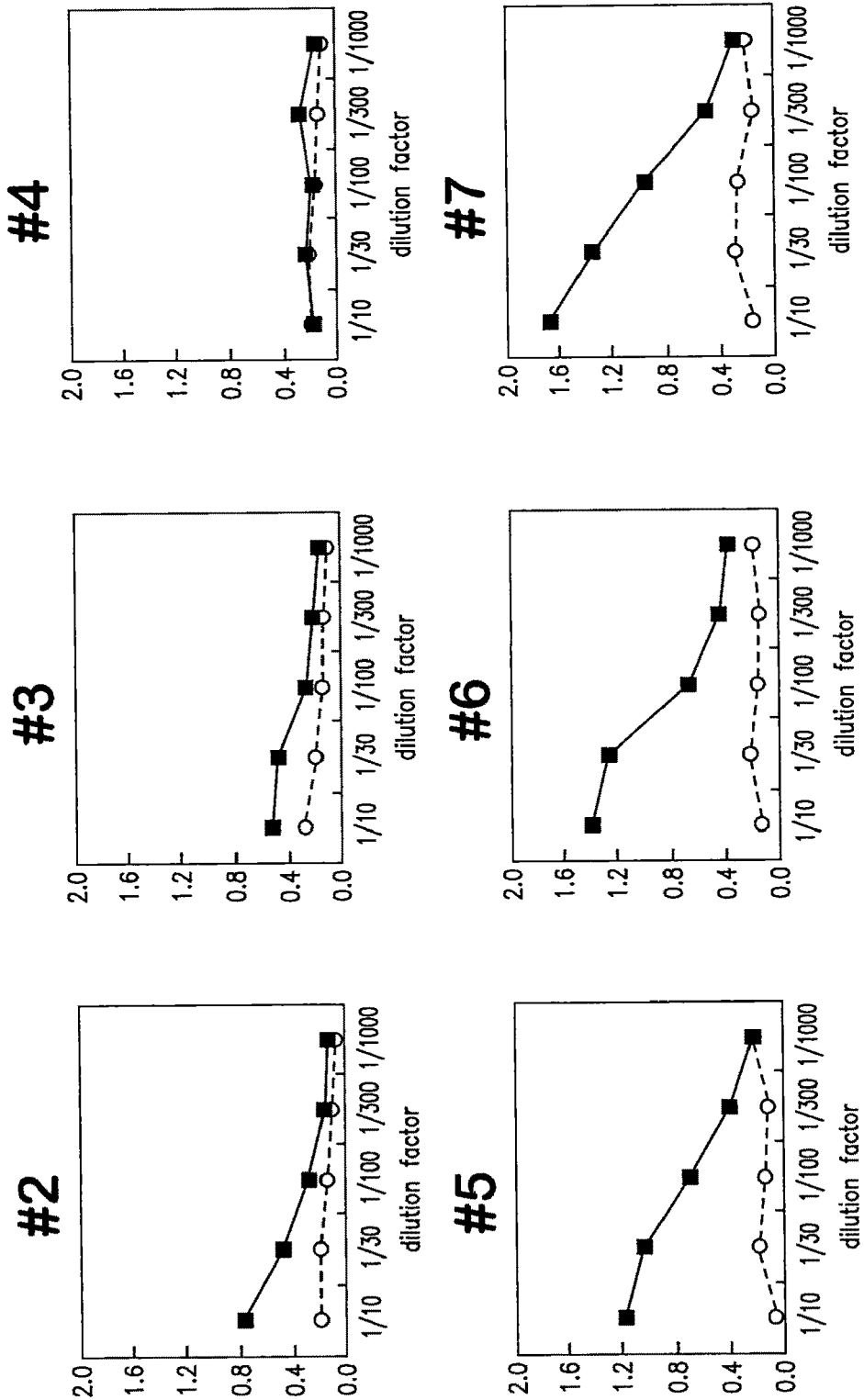
Figure 7A:
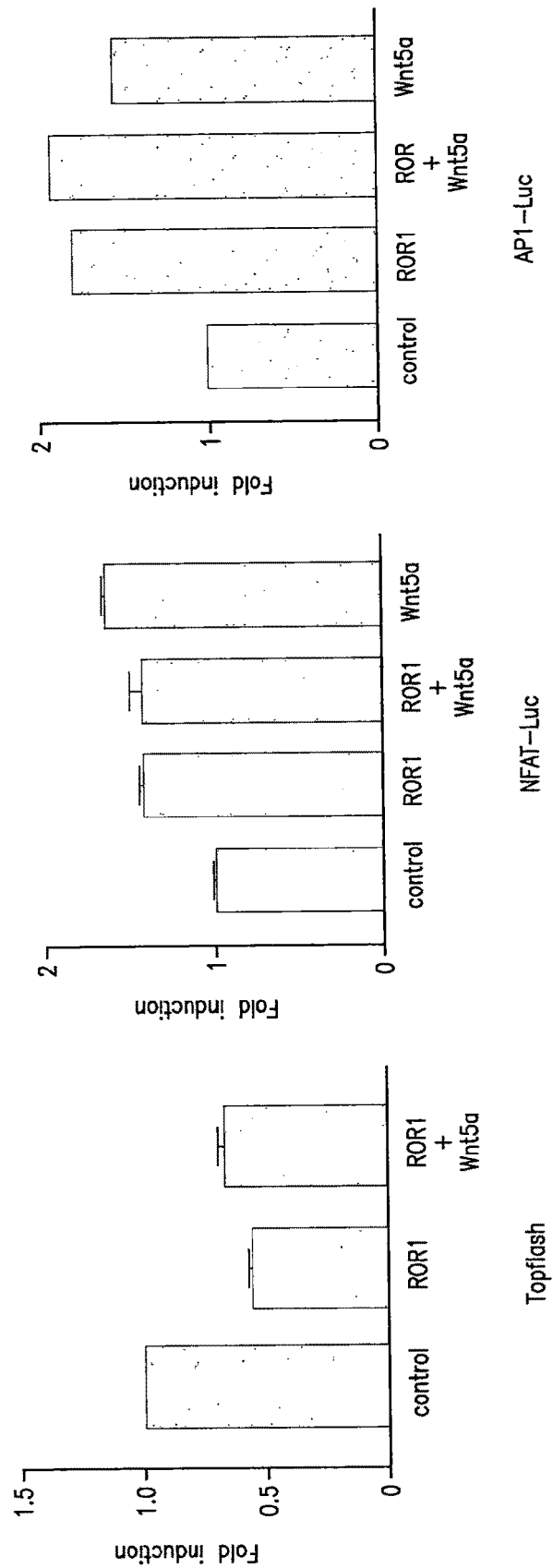
FIGS. 7A through 7C show ROR1 and Wnt5a activated NF-κB reporter expression.
Figure 7B:
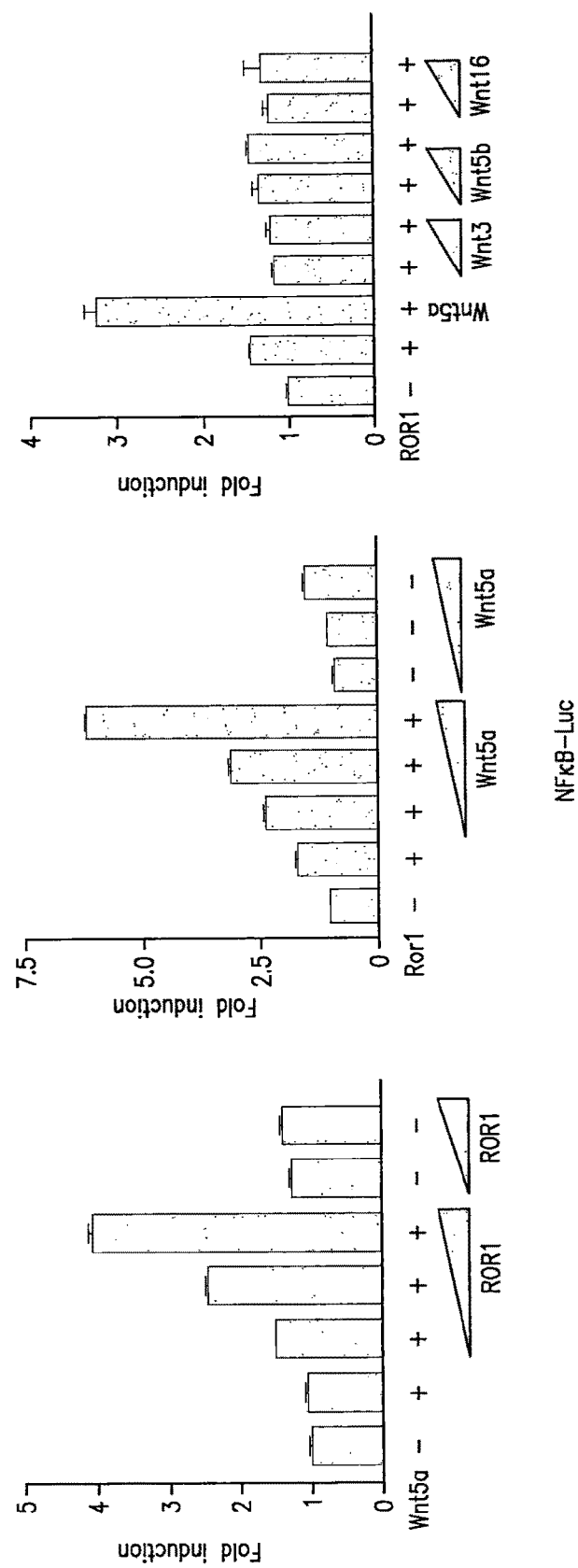

As described in the Examples, ROR1 interacts physically with Wnt5a. The interaction of ROR1 with Wnt5a was implicated in studies demonstrating that co-transfection of expression vectors encoding NF-κB reporter constructs, ROR1, and Wnt5a, but not other Wnt factors, could induce activation of NF-κB in a mutually dose-dependent fashion (FIG. 7B). This activity was independent of expression of LPR5/6, which ordinarily serves as a co-receptor for Wnt receptors. Physical interaction of ROR1 with Wnt5a was observed using recombinant proteins, demonstrating that ROR1 has binding activity for Wnt5a independent of LPR5/6 (FIG. 6B). Nonetheless, Wnt5a apparently could not activate the canonical Wnt-signaling pathway when co-expressed with ROR1 in 293 cells (FIG. 7A).

Prior studies suggested that there is crosstalk between the Wnt-signaling pathway and the NF-κB-signaling pathway. β-catenin apparently can physically complex with NF-κB, resulting in reduction of NF-κB DNA binding, transactivation activity, and target gene expression. Whereas NB kinase-alpha (IκKa), involved in the phosphorylation of NF-κB2/p100, can phosphorylate and stabilize β-catenin, the kinase involved in activation of the canonical p50/p65 NF-κB pathway, namely IκKB, can enhance β-catenin degradation. Conceivably, the inability of ROR1 to activate the LEF/TCF-signaling may be secondary in part to its capacity to activate IκKP, leading to reduced stability of p-catenin and enhanced activity of NF-κB, which in itself could potentially play a role in cancer development. Furthermore, expression of ROR1 in CLL could contribute to the growth and/or survival of neoplastic cells induced by interaction with tissue stromal cells that might elaborate Wnt5a and other factors that activate NF-κB. Even though found circulating in the blood, CLL cells derive a survival benefit from interactions with marrow stromal cells, nurse-like cells, or dendritic cells, which are found in the leukemia-infiltrated marrow or lymphoid tissues of patients with this disease. It is noteworthy in this regard that dendritic cells have been found to express high-levels of Wnt5a.

To investigate whether Wnt5a could enhance the survival of CLL cells, artificial stromal cells, namely CHO cells, were engineered to express human Wnt5a, as described in the examples. The studies revealed that co-culture of CLL cells with CHO-Wnt5a cells maintained significantly higher viability over time in vitro than the same CLL cells co-cultured with CHO cells, which serves to control for other factors that might influence CLL-cell survival. These studies provide the first evidence that the survival of CLL cells can be enhanced in vitro by such Wnt factors, which presumably also might function to enhance the survival of CLL cells in lymphoid-tissue microenvironments containing cells that express Wnt5a.

Figure 18A:
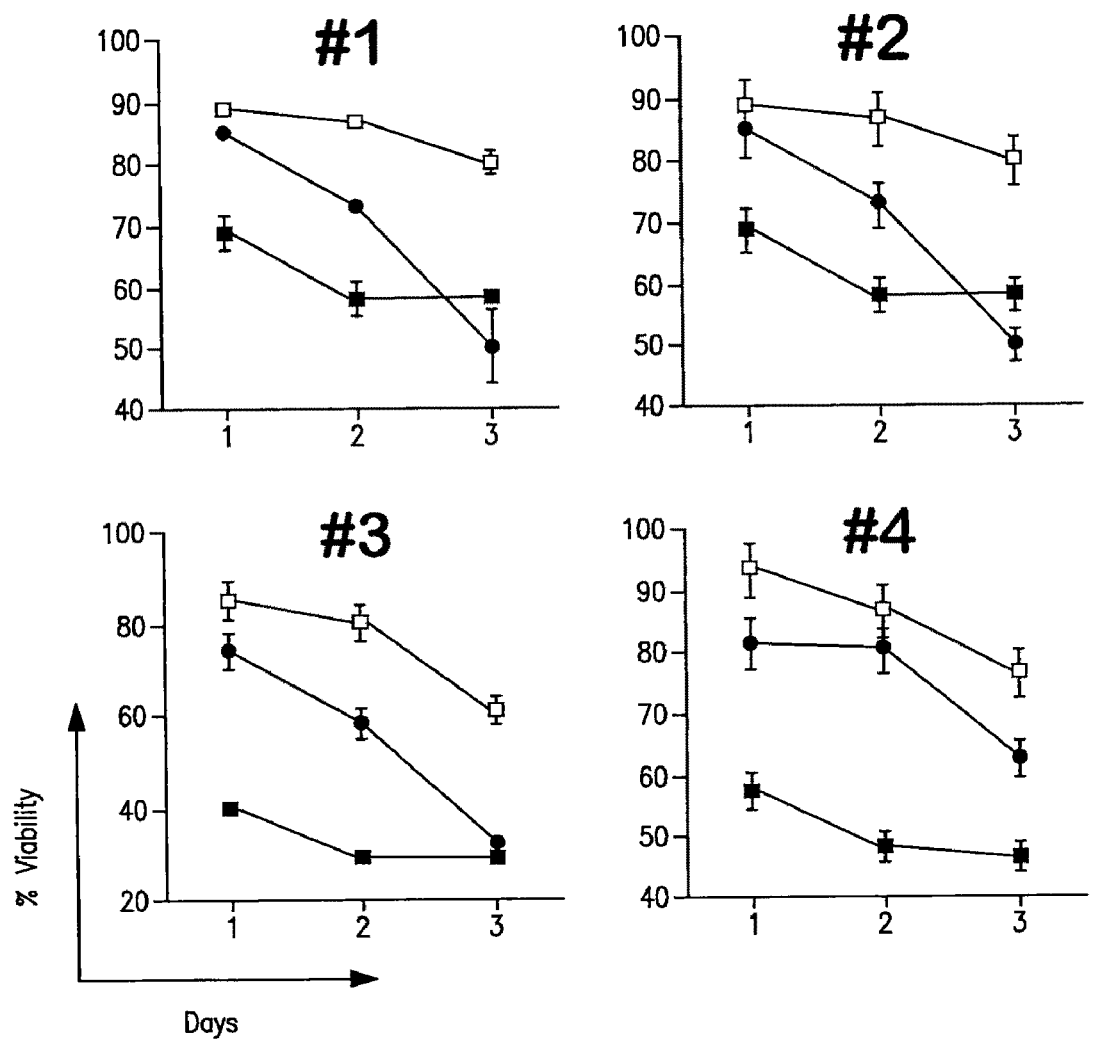
FIG. 18A depicts a graph showing the effect of Wnt5a on the viability of CLL cells cultured in vitro. CLL cells from each of 4 unrelated patients were cultured alone (solid squares), or together with CHO cells (solid diamonds), or CHO-Wnt5a cells. The percent viability of the CD19+ CLL cells, indicated on the ordinate, was assessed via flow cytometry on days 1, 2, and 3 of culture, as indicated on the abscissa. Each data point represents the mean value of quadruplicate samples cultured in parallel. The error bars represent the standard error about the mean.
Figure 18B:
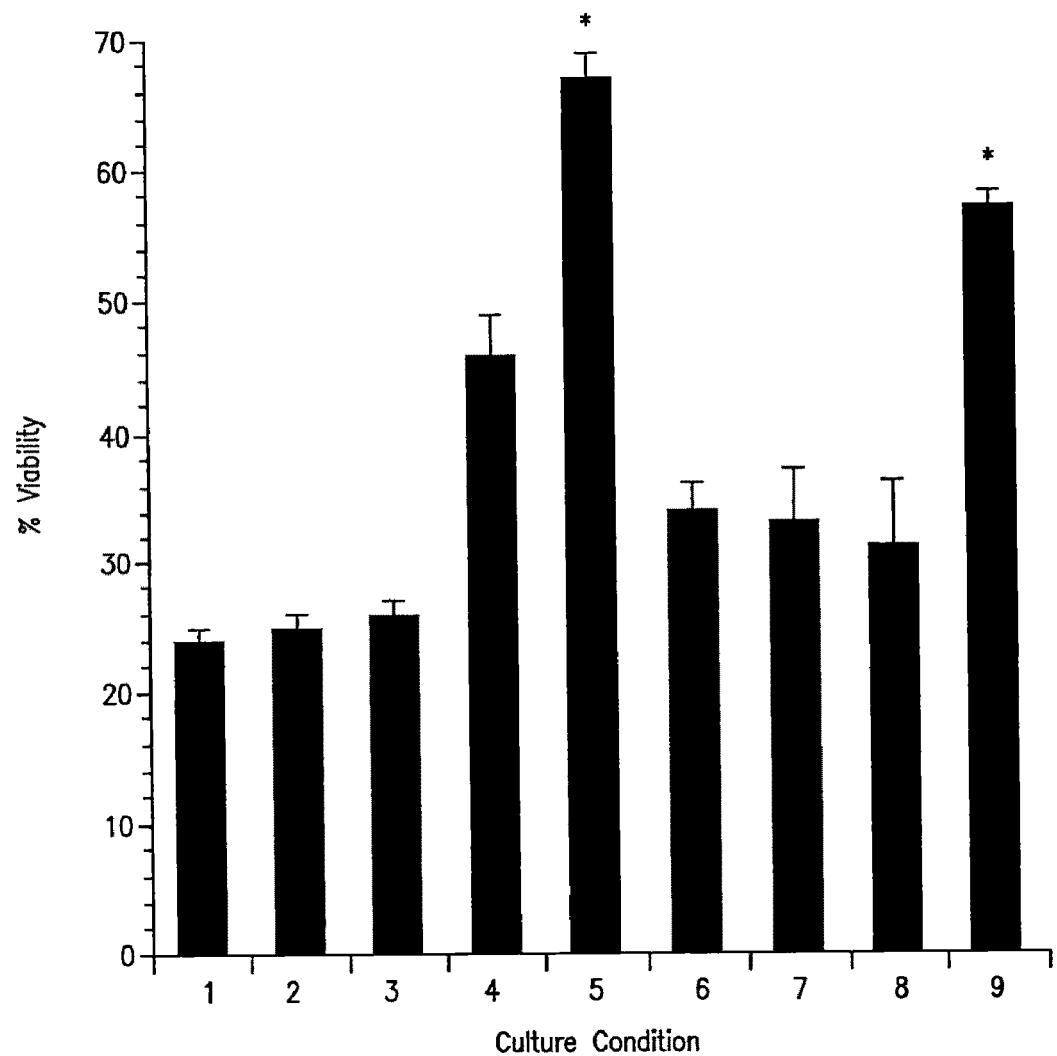
FIG. 18B depicts a chart of the effect of patient sera on the viability of CLL cells in vitro. CLL cells were cultured for 2 days in RPM1 media containing 20% human serum, either alone or together with CHO cells or CHO-Wnt5a cells and then assessed for viability by flow cytometry. The bars indicate the mean percent viability of the CD19' CLL cells, as indicated on the ordinate, of quadrulicate wells for each culture condition, as defined on the abscissa. Except for condition 1, all cultures had serum samples from patient #5 that were collected either before (pre-treatment) or two weeks after the last infusion of autologous Ad-CD154-transduced CLL cells (post-treatment). For culture conditions 1, 2, and 3 the CLL cells were cultured by themselves in media containing 1) normal human serum, 2) pre-treatment serum, or 3) post-treatment serum. For culture conditions 4, 6, and 8 the CLL cells were co-cultured with CHO cells and for culture conditions 5, 7, and 9 the CLL cells were co-cultured with CHO-Wnt5a cells. Cultures 4 and 5 used media with pre-treatment serum, cultures 6 and 7 used media with post-treatment serum that previously had been absorbed on CHO cells, and cultures 8 and 9 used media with post-treatment serum that previously had been absorbed on CHO-ROR1 cells to remove its anti-ROR1 binding activity. The error bars depict the standard error about the mean of quadruplicate wells cultured in parallel. The asterisks above bars for culture conditions 5 and 9 indicate that the CLL cells in those culture conditions had significantly greater percent viability than that of CLL cells in the other culture conditions by Bonferroni t test (PC 0.05).

Although there are other receptors for Wnt5a, the data described herein indicates ROR1 is at least in part responsible for the survival-signal triggered by co-culture with Wnt5a-expressing CHO cells. This is indicated by the finding that serum obtained after treatment with autologous Ad-CD154-CLL cells could neutralize the capacity of CHO-Wnt5a cells to enhance the survival of CLL cells over that of CLL cells co-cultured with CHO cells or CLL cells cultured alone (FIG. 18B). Absorption of such antiserum with CHO-ROR1 cells abrogated the capacity of the post-treatment serum to neutralize the activity of CHO-Wnt5a cells. Conceivably, such anti-ROR1 antibodies could be responsible for some of the size-reductions observed in the lymph nodes of patients who had received infusions of autologous Ad-CD154-CLL cells.

ROR1 Antibody

Certain embodiments comprise immunopeptides directed against ROR1 protein. The immunoglobulin peptides, or antibodies, described herein are shown to bind to the ROR1 protein. The ROR1 binding activity is specific; the observed binding of antibody to ROR1 is not substantially blocked by non-specific reagents. These ROR1 specific antibodies can be used to differentiate between ROR1 cells and normal cells. The ROR1 specific antibodies can also be used in immunotherapy against a ROR1 cancer and to determine the response after therapy for a ROR1 cancer.

Such immunopeptides can be raised in a variety of means known to the art. For example, and as shown in the examples, Ad-CD154 therapy induces humoral immunity against CLL, thus allowing the derivation of immunoglobulin peptides specific against ROR1. The inventors have discovered that tandem injections of Ad-CD154 induces antibody production against a novel cell surface TAA of CLL B cells, orphan tyrosine kinase receptor ROR1.

As used herein, the term antibody encompasses all types of antibodies, e.g., polyclonal, monoclonal, and those produced by the phage display methodology. Particularly preferred antibodies of the invention are antibodies which have a relatively high degree of affinity for ROR1. In certain embodiments, the antibodies exhibit an affinity for ROR1 of about $Kd<10^{-8}$ M.

Substantially purified generally refers to a composition which is essentially free of other cellular components with which the antibodies are associated in a non-purified, e.g., native state or environment. Purified antibody is generally in a homogeneous state, although it can be in either in a dry state or in an aqueous solution. Purity and homogeneity are typically determined using analytical chemistry techniques such as polyacrylamide gel electrophoresis or high performance liquid chromatography.

Substantially purified ROR1-specific antibody will usually comprise more than 80% of all macromolecular species present in a preparation prior to admixture or formulation of the antibody with a pharmaceutical carrier, excipient, adjuvant, buffer, absorption enhancing agent, stabilizer, preservative, adjuvant or other co-ingredient. More typically, the antibody is purified to represent greater than 90% of all proteins present in a purified preparation. In specific embodiments, the antibody is purified to greater than 95% purity or may be essentially homogeneous wherein other macromolecular species are not detectable by conventional techniques.

Immunoglobulin peptides include, for example, polyclonal antibodies, monoclonal antibodies, and antibody fragments. The following describes generation of immunoglobulin peptides, specifically ROR1 antibodies, via methods that can be used by those skilled in the art to make other suitable immunoglobulin peptides having similar affinity and specificity which are functionally equivalent to those used in the examples.

Polyclonal Antibodies

Polyclonal antibodies may be readily generated by one of ordinary skill in the art from a variety of warm-blooded animals such as horses, cows, various fowl, rabbits, mice, or rats. Briefly, ROR1 antigen is utilized to immunize the animal through intraperitoneal, intramuscular, intraocular, or subcutaneous injections, with an adjuvant such as Freund's complete or incomplete adjuvant. Following several booster immunizations, samples of serum are collected and tested for reactivity to ROR1. Particularly preferred polyclonal antisera will give a signal on one of these assays that is at least three times greater than background. Once the titer of the animal has reached a plateau in terms of its reactivity to ROR1, larger quantities of antisera may be readily obtained either by weekly bleedings, or by exsanguinating the animal.

As discussed, it has been found that human subjects treated with Ad-CD154 therapy developed anti-sera that abrogated Wnt5a/ROR1 binding. Such purified human sera include those on deposit with the American Type Culture Collection as Accession No. PTA-8634.

Monoclonal Antibodies

Monoclonal antibody (mAb) technology can be used to obtain mAbs to ROR1. Briefly, hybridomas are produced using spleen cells from mice immunized with ROR1 antigens. The spleen cells of each immunized mouse are fused with mouse myeloma Sp 2/0 cells, for example using the polyethylene glycol fusion method of Galfre, G. and Milstein, C., Methods Enzymol., 73:3-46 (1981). Growth of hybridomas, selection in HAT medium, cloning and screening of clones against antigens are carried out using standard methodology (Galfre, G. and Milstein, C., Methods Enzymol., 73:3-46 (1981)).

HAT-selected clones are injected into mice to produce large quantities of mAb in ascites as described by Galfre, G. and Milstein, C., Methods Enzymol., 73:3-46 (1981), which can be purified using protein A column chromatography (Bio-Rad, Hercules, Calif.). mAbs are selected on the basis of their (a) specificity for ROR1, (b) high binding affinity, (c) isotype, and (d) stability.

mAbs can be screened or tested for ROR1 specificity using any of a variety of standard techniques, including Western Blotting (Koren, E. et al., Biochim. Biophys. Acta 876:91-100 (1986)) and enzyme-linked immunosorbent assay (ELISA) (Koren, E. et al., Biochim. Biophys. Acta 876:91-100 (1986)).

Humanized Antibodies

Humanized forms of mouse antibodies can be generated by linking the CDR regions of non-human antibodies to human constant regions by recombinant DNA techniques (see, e.g., Queen et al., Proc. Natl. Acad. Sci. USA 86:10029-10033, 1989 and WO 90/07861, each incorporated by reference). Human antibodies can be obtained using phage-display methods (see, e.g., Dower et al., WO 91/17271; McCafferty et al., WO 92/01047). In these methods, libraries of phage are produced in which members display different antibodies on their outersurfaces. Antibodies are usually displayed as Fv or Fab fragments. Phage displaying antibodies with a desired specificity may be selected by affinity enrichment.

Human antibodies may be selected by competitive binding experiments, or otherwise, to have the same epitope specificity as a particular mouse antibody. Using these techniques, a humanized ROR1 antibody having the human IgG1 constant region domain and the human kappa light chain constant region domain with the mouse heavy and light chain variable regions. The humanized antibody has the binding specificity of a mouse ROR1 mAb, specifically the 45A mAb described in Example 9.

Antibody Fragments

It may be desirable to produce and use functional fragments of a mAb for a particular application. The well-known basic structure of a typical IgG molecule is a symmetrical tetrameric Y-shaped molecule of approximately 150,000 to 200,000 daltons consisting of two identical light polypeptide chains (containing about 220 amino acids) and two identical heavy polypeptide chains (containing about 440 amino acids). Heavy chains are linked to one another through at least one disulfide bond. Each light chain is linked to a contiguous heavy chain by a disulfide linkage. An antigen-binding site or domain is located in each arm of the Y-shaped antibody molecule and is formed between the amino terminal regions of each pair of disulfide linked light and heavy chains. These amino terminal regions of the light and heavy chains consist of approximately their first 110 amino terminal amino acids and are known as the variable regions of the light and heavy chains. In addition, within the variable regions of the light and heavy chains there are hypervariable regions which contain stretches of amino acid sequences, known as complementarity determining regions (CDRs). CDRs are responsible for the antibody's specificity for one particular site on an antigen molecule called an epitope. Thus, the typical IgG molecule is divalent in that it can bind two antigen molecules because each antigen-binding site is able to bind the specific epitope of each antigen molecule. The carboxy terminal regions of light and heavy chains are similar or identical to those of other antibody molecules and are called constant regions. The amino acid sequence of the constant region of the heavy chains of a particular antibody defines what class of antibody it is, for example, IgG, IgD, IgE, IgA or IgM. Some classes of antibodies contain two or more identical antibodies associated with each other in multivalent antigen-binding arrangements.

Fab and F(ab')$_2$ fragments of mAbs that bind ROR1 can be used in place of whole mAbs. Because Fab and F(ab')$_2$ fragments are smaller than intact antibody molecules, more antigen-binding domains are available than when whole antibody molecules are used. Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(ab')$_2$ fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

Recombinant DNA methods have been developed which permit the production and selection of recombinant immunoglobulin peptides which are single chain antigen-binding polypeptides known as single chain Fv fragments (ScFvs or ScFv antibodies). Further, ScFvs can be dimerized to produce a diabody. ScFvs bind a specific epitope of interest and can be produced using any of a variety of recombinant bacterial phage-based methods, for example as described in Lowman et al. (1991) Biochemistry, 30, 10832-10838; Clackson et al. (1991) Nature 352, 624-628; and Cwirla et al. (1990) Proc. Natl. Acad. Sci. USA 87, 6378-6382. These methods are usually based on producing genetically altered filamentous phage, such as recombinant M13 or fd phages, which display on the surface of the phage particle a recombinant fusion protein containing the antigen-binding ScFv antibody as the amino terminal region of the fusion protein and the minor phage coat protein g3p as the carboxy terminal region of the fusion protein. Such recombinant phages can be readily grown and isolated using well-known phage methods. Furthermore, the intact phage particles can usually be screened directly for the presence (display) of an antigen-binding ScFv on their surface without the necessity of isolating the ScFv away from the phage particle.

To produce an ScFv, standard reverse transcriptase protocols are used to first produce cDNA from mRNA isolated from a hybridoma that produces an mAb for ROR1 antigen. The cDNA molecules encoding the variable regions of the heavy and light chains of the mAb can then be amplified by standard polymerase chain reaction (PCR) methodology using a set of primers for mouse immunoglobulin heavy and light variable regions (Clackson (1991) Nature, 352, 624-628). The amplified cDNAs encoding mAb heavy and light chain variable regions are then linked together with a linker oligonucleotide in order to generate a recombinant ScFv DNA molecule. The ScFv DNA is ligated into a filamentous phage plasmid designed to fuse the amplified cDNA sequences into the 5' region of the phage gene encoding the minor coat protein called g3p. *Escherichia coli* bacterial cells are than transformed with the recombinant phage plasmids, and filamentous phage grown and harvested. The desired recombinant phages display antigen-binding domains fused to the amino terminal region of the minor coat protein. Such "display phages" can then be passed over immobilized antigen, for example, using the method known as "panning", see Parmley and Smith (1989) Adv. Exp. Med. Biol. 251, 215-218; Cwirla et al. (1990) Proc. Natl. Acad. Sci. USA 87, 6378-6382, to adsorb those phage particles containing ScFv antibody proteins that are capable of binding antigen. The antigen-binding phage particles can then be amplified by standard phage infection methods, and the amplified recombinant phage population again selected for antigen-binding ability. Such successive rounds of selection for antigen-binding ability, followed by amplification, select for enhanced antigen-binding ability in the ScFvs displayed on recombinant phages. Selection for increased antigen-binding ability may be made by adjusting the conditions under which binding takes place to require a tighter binding activity. Another method to select for enhanced antigen-binding activity is to alter nucleotide sequences within the cDNA encoding the binding domain of the ScFv and subject recombinant phage populations to successive rounds of selection for antigen-binding activity and amplification (see Lowman et al. (1991) Biochemistry 30, 10832-10838; and Cwirla et al. (1990) Proc. Natl. Acad. Sci. USA 87, 6378-6382).

Once an ScFv is selected, the recombinant ROR1 antibody can be produced in a free form using an appropriate vector in conjunction with *E. coli* strain HB2151. These bacteria actually secrete ScFv in a soluble form, free of phage components (Hoogenboom et al. (1991) Nucl. Acids Res. 19, 4133-4137). The purification of soluble ScFv from the HB2151 bacteria culture medium can be accomplished by affinity chromatography using antigen molecules immobilized on a solid support such as AFFIGEL™ (BioRad, Hercules, Calif.).

Other developments in the recombinant antibody technology demonstrate possibilities for further improvements such as increased avidity of binding by polymerization of ScFvs into dimers and tetramers (see Holliger et al. (1993) Proc. Natl. Acad. Sci. USA 90, 6444-6448).

Because ScFvs are even smaller molecules than Fab or F(ab')$_2$ fragments, they can be used to attain even higher densities of antigen binding sites per unit of surface area when immobilized on a solid support material than possible using whole antibodies, F(ab')$_2$, or Fab fragments. Furthermore, recombinant antibody technology offers a more stable genetic source of antibodies, as compared with hybridomas. Recombinant antibodies can also be produced more quickly and economically using standard bacterial phage production methods.

Recombinant Antibody Production

To produce antibodies described herein recombinantly, nucleic acids encoding light and heavy chain variable regions, optionally linked to constant regions, are inserted into expression vectors. The light and heavy chains can be cloned in the same or different expression vectors. For example, the heavy and light chains of SEQ ID NOs: 3-7 can be used according to the present invention. The teachings of U.S. Pat. No. 6,287,569 to Kipps et al., incorporated herein by reference in its entirety, and the methods provided herein can readily be adapted by those of skill in the art to create the vaccines of the present invention. The DNA segments encoding antibody chains are operably linked to control sequences in the expression vector(s) that ensure the expression of antibody chains. Such control sequences include a signal sequence, a promoter, an enhancer, and a transcription termination sequence.

Expression vectors are typically replicable in the host organisms either as episomes or as an integral part of the host chromosome. *E. coli* is one procaryotic host particularly useful for expressing antibodies of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda. Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired. Mammalian tissue cell culture can also be used to express and produce the antibodies of the present invention (see, e.g., Winnacker, From Genes to Clones VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CV1 line transformed by SV40 (COS-7, ATCC CRL 1651); human embryonic kidney line; baby hamster kidney cells (BHK, ATCC CCL 10); Chinese hamster ovary-cells (CHO); mouse sertoli cells; monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and TRI cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts (see, e.g., Sambrook et al., Molecular Cloning: A Laboratory Manual, Cold Spring Harbor Press, 2nd ed., 1989). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, e.g., Scopes, Protein Purification, Springer-Verlag, N.Y., 1982). Substantially pure immunoglobulins of at least about 90 to 95% homogeneity are preferred, and 98 to 99% or more homogeneity most preferred.

Labeled Antibody

A labeled antibody or a detectably labeled antibody is generally an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art include radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds., 1988, Antibodies: A Laboratory Manual, Cold Spring Harbor Laboratory Press, Cold Spring Harbor, N.Y.) Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

Diagnosis of ROR1 Cancer

Figure 15:
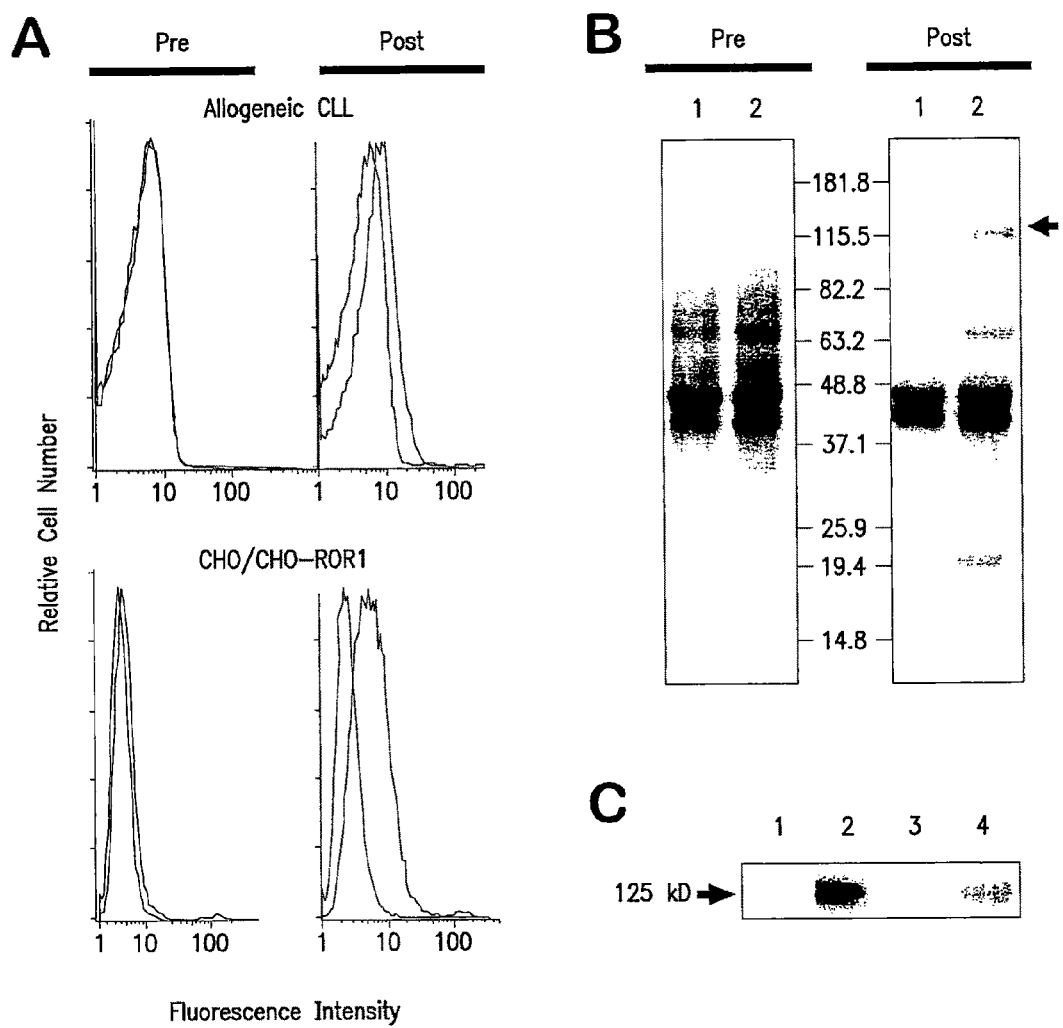
FIG. 15A depicts histograns showing levels of ROR1 in cells from either a CLL patient pre and post-Ad-CD154 treatment or a healthy donor.
FIG. 15B depicts a immunoblot analyses using lysates of membrane proteins isolated from the blood lymphocytes of a healthy donor (lane 1) or the CLL cells of an untreated patient (lane 2), as indicated at the top of each immunoblot using sera from patient #7 obtained before (PRE, left panel) or after treatment with autologous Ad-CD154-transduced CLL cells (POST, right panel).
FIG. 15C depicts an immunoblot analysis using lysates of membrane proteins isolated from CHO cells (lane 1) or CHO-ROR1 cells (lane 2) or the blood lymphocytes of a healthy donor (lane 3) or the CLL cells of an untreated patient (lane 4), as indicated at the top of each immunoblot using sera from patient #7 after treatment with autologous Ad-CD154-transduced CLL cells.

The ROR1 antibodies described herein can be used to differentiate between ROR1 expressing cells and normal cells and, thus, can be used to detect and/or diagnose disease in subjects. ROR1 expressing cancer cells include CLL and other lymphoma (e.g. Burkitt's), renal cell carcinoma, colon adenocarcinoma, colorectal (see, e.g., FIG. 15).

The methods for detecting such disease generally include contacting a sample from a subject having, or at risk of having, a lymphoma with a reagent that detects ROR1, and detecting the reaction of the reagent. Within these methods, detection of a reaction is indicative of the presence and/or quantity of ROR1 in the sample. The reaction of the reagent with the sample is then compared to a control. Any biological sample which may contain a detectable amount of ROR1 can be used. Examples of biological samples of use with the invention are blood, serum, plasma, urine, mucous, feces, cerebrospinal fluid, pleural fluid, ascites, and sputum samples. Tissue or cell samples can also be used with the subject invention. These samples can be obtained by many methods such as cellular aspiration, or by surgical removal of a biopsy sample. The level of ROR1 in the sample can be compared with the level in a sample not affected by the targeted disorder or condition. Control samples not affected by a targeted disease processes can be taken from the same subject, or can be from a normal control subject not affected by the disease process, or can be from a cell line.

Contacting the sample and anti-ROR1 antibody generally includes incubation under conditions which allow contact in solution and/or solid phase between the reagent and sample. Detection can be performed by any means suitable to identify the interaction of the reagent with ROR1. In one embodiment, when the reagent is an antibody, the antibody can be detectably labeled. Detectable labels are well known in the art, and include radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Alternatively, when the reagent is an antibody, detection can be performed using a second antibody which is detectably labeled which recognizes the antibody that binds ROR1. The antibody may also be biotinylated, and a second avidinated label used to determine the presence of the biotinylated reagent which detects ROR1.

The antibodies of the invention are suited for use, for example, in immunoassays in which they can be utilized in liquid phase or bound to a solid phase carrier. The antibodies employed in these immunoassays can be detectably labeled in various ways. Examples of types of immunoassays which can effectively employ antibodies of the invention are, competitive and non-competitive immunoassays, in either a direct or indirect format. Examples of such immunoassays include a radioimmunoassay (RIA), and a sandwich (immunometric) assay. Those of skill in the art will readily discern additional immunoassay formats useful within the invention Other immunoassays for use within the invention include "forward" assays for the detection of a protein in which a first anti-protein antibody (e.g., an anti-ROR1 antibody) bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample. The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The antibody component of immunometric assays described herein may be added to a solid phase support capable of immobilizing proteins. By "solid phase support" or "support" is intended any material capable of binding proteins. Well-known solid phase supports include glass, polystyrene, polypropylene, polyethylene, dextran, nylon, amylases, natural and modified celluloses (including nitrocellulose sheets and filters), polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate. For immunoassay and immunodiagnostic purposes, the antibodies of the invention can be bound to many different carriers, both soluble and insoluble, and can be used to detect the presence of an antigen comprising ROR1 (or fragments, derivatives, conjugates, homologues, or variants thereof). Those skilled in the art will discern other suitable carriers for binding antibodies useful within the invention. In addition, there are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds, as described above.

In using the antibodies described herein for the in vitro or in vivo detection of ROR1, the detectably labeled antibody is provided in an amount which is diagnostically effective. Thus, an amount of detectably labeled antibody is contacted or administered in sufficient quantity to enable detection of ROR1 in the subject sample to be assayed.

Within more detailed diagnostic methods of the invention, in vivo immunodiagnostic tools are provided, as exemplified by immunoscintigraphic methods and compositions. Immunoscintigraphy (IS) is discussed in detail in P. Lechner et al., Dis Colon Rectum 1993; 36:930-935 and F. L. Moffet et al., J Clin Oncol 14:2295-2305 (1966). IS (or radioscintigraphy) employs radioactive-labeled antibody, typically Fab' fragments (Goldenberg et al.; Eur J Nucl Med 1989; 15:426), to recognize defined epitopes of targeted proteins. Fab' fragments of the antibodies provided herein, comprising immunoglobulins of the IgGI fraction that have their Fc portions removed, are highly capable of targeting epitopes on proCPR, activated CPR, and/or inactivated CPR in a test sample or subject. Because these Fab' fragments have minimal antigenity, they cause neither human antimouse antibody response, nor any allergic reactions of unpredictable nature. The smaller molecular weight of Fab' fragments compared with intact antibody allows the fragment to leave the intravascular space and target a broader array of in vivo compartments for diagnostic purposes.

For radioscintigraphy, an anti-ROR1 radioactive monoclonal antibody is typically injected into a patient for identifying, measuring, and/or localizing ROR1 in the subject, (see, e.g., Delaloye et al., Seminars in Nuclear Medicine 25(2): 144-164, 1995). In radioimaging with monoclonal antibodies, a chemically modified (chelate) form of the monoclonal antibody is typically prepared and stored as a relatively stable product. To be used clinically, however, the monoclonal antibody sample must be mixed with a radioactive metal, such as $^{99}$Tc, then purified to remove excess, unbound radioactive metal, and then administered to a patient within 6 hours, (see, e.g., Eckelman et al., Nuc. Med. Biol. 16: 171-176, 1989). Radioisotopes, for example $^{99}$Tc, an isotope with a short physical half-life and high photon abundance, can be administered at high doses and allow early imaging with a gamma camera. This is very suitable for use in conjunction with Fab' fragments, the half-lives of which are also short.

Monitoring of a ROR1 Cancer and Cancer Therapy

Further, the anti-ROR1 antibodies described herein can be used in vitro and in vivo to monitor the appearance, status, course, or treatment of a ROR1 cancer in a subject. For example, by measuring an increase or decrease in the amount of ROR1 in a subject (optionally in comparison to control levels in a normal subject or sample), the appearance, status, course, or treatment of the cancer or condition in the subject number can be observed or evaluated. Based on these and comparable diagnostic methods, it is further possible to determine whether a particular therapeutic regimen, such as a treatment regimen employing antibodies of the invention directed against the cancer is effective. Methods of detecting and/or quantifying levels of ROR1 and corresponding cancer disease state are as described above.

Therapeutic Treatment of Lymphoma

ROR1 antagonists (including ROR1 antibodies, anti-sera that abrogate Wnt5a/ROR1 interactions, small molecule inhibitors, antisense RNA, and siRNA) can be employed as therapeutic or prophylactic pharmacological agents in any subject in which it is desirable to administer, in vitro, ex vivo, or in vivo the subject antagonists that bind ROR1. Typical subjects for treatment or management according to the methods herein are subjects presenting with a ROR1 cancer. The antagonists described herein specifically recognize ROR1 protein, found in lymphoma samples but not expressed in cells of normal adults, and therefore can be used for detecting and/or neutralizing these biomolecules, and/or blocking their interactions with other biomolecules, in vitro or in vivo. While under no obligation to provide a mechanism of action, it is thought that ROR1 can serve as a receptor for Wnt5a to trigger the NF-kappa B pathway, which pathway is implicated in oncogenesis. See e.g. Example 12. Thus, the ROR1 gene, which plays a role in disease pathogenesis and/or progression, encodes a protein that can be targeted by immune therapy for patients with a ROR1 cancer.

Antibodies

In certain therapeutic embodiments, the selected antibody will typically be an anti-ROR1 antibody, which may be administered alone, or in combination with, or conjugated to, one or more combinatorial therapeutic agents. When the antibodies described herein are administered alone as therapeutic agents, they may exert a beneficial effect in the subject by a variety of mechanisms. In certain embodiments, monoclonal antibodies that specifically bind ROR1 are purified and administered to a patient to neutralize one or more forms of ROR1, to block one or more activities of ROR1, or to block or inhibit an interaction of one or more forms of ROR1 with another biomolecule.

The immunotherapeutic reagents of the invention may include humanized antibodies, and can be combined for therapeutic use with additional active or inert ingredients, e.g., in conventional pharmaceutically acceptable carriers or diluents, e.g., immunogenic adjuvants, and optionally with adjunctive or combinatorially active agents such as anti-inflammatory ant anti-fibrinolytic drugs.

In other embodiments, therapeutic antibodies described herein are coordinately administered with, co-formulated with, or coupled to (e.g., covalently bonded) a combinatorial therapeutic agent, for example a radionuclide, a differentiation inducer, a drug, or a toxin. Various known radionuclides can be employed, including $^{90}$Y, $^{123}$I, $^{125}$I, $^{131}$I, $^{186}$Re, $^{188}$Re, and $^{211}$At. Useful drugs for use in such combinatorial treatment formulations and methods include methotrexate, and pyrimidine and purine analogs. Suitable differentiation inducers include phorbol esters and butyric acid. Suitable toxins include ricin, abrin, diptheria toxin, cholera toxin, gelonin, *Pseudomonas exotoxin*, *Shigella* toxin, and pokeweed antiviral protein. These combinatorial therapeutic agents can be coupled to an anti-ROR1 antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Alternatively, it may be desirable to couple a combinatorial therapeutic agent and an antibody via a linker group as a spacer to distance an antibody from the combinatorial therapeutic agent in order to avoid interference with binding capabilities. A linker group can also serve to increase the chemical reactivity of a substituent on an agent or an antibody, and thus increase the coupling efficiency. It will be further evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be affected, for example, through amino groups, carboxyl groups, sulfhydryl groups or oxidized carbohydrate residues.

Where a therapeutic agent is more potent when free from the antibody portion of the immunoconjugates described herein, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.) It may also be desirable to couple more than one agent to an anti-ROR1 antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A variety of routes of administration for the antibodies and immunoconjugates may be used. Typically, administration is intravenous, intramuscular, or subcutaneous.

It will be evident that the precise dose of the antibody/immunoconjugate will vary depending upon such factors as the antibody used, the antigen density, and the rate of clearance of the antibody. A safe and effective amount of an anti-ROR1 agent is, for example, that amount that would cause the desired therapeutic effect in a patient while minimizing undesired side effects. Generally, a therapeutically effective amount is that sufficient to promote production of one or more cytokines and/or to cause complement-mediated or antibody-dependent cellular cytotoxicity. The dosage regimen will be determined by skilled clinicians, based on factors such as the exact nature of the condition being treated, the severity of the condition, the age and general physical condition of the patient, and so on.

siRNA

In certain therapeutic embodiments, the ROR1 antagonist is siRNA. The levels of ROR1 can be down-regulated by RNA interference by administering to the patient a therapeutically effective amount of small interfering RNAs (siRNA) specific for ROR1. siRNA specific for ROR1 can be produced commercially from a variety of sources, such as Ambion (Austin, Tex.). The siRNA can be administered to the subject by any means suitable for delivering the siRNA to the blood. For example, the siRNA can be administered by gene gun, electroporation, or by other suitable parenteral or enteral administration routes, such as intravitreous injection.

RNA interference is the process by which double stranded RNA (dsRNA) specifically suppresses the expression of a gene bearing its complementary sequence. Suppression of the ROR1 gene inhibits the production of the ROR1 protein. Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. Preferably, the siRNA comprises short double-stranded RNA from about 17 nucleotides to about 29 nucleotides in length, preferably from about 19 to about 25 nucleotides in length, that are targeted to the target mRNA.

As an example, an effective amount of the siRNA can be an amount sufficient to cause RNAi-mediated degradation of the target ROR1 mRNA, or an amount sufficient to inhibit the progression of a lymphoma in a subject. One skilled in the art can readily determine an effective amount of the siRNA of the invention to be administered to a given subject by taking into account factors such as the size and weight of the subject; the extent of the neovascularization or disease penetration; the age, health and sex of the subject; the route of administration; and whether the administration is regional or systemic. Generally, an effective amount of siRNA comprises an intercellular concentration of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The siRNA can be targeted to any stretch of approximately 19-25 contiguous nucleotides in any of the ROR1 mRNA target sequences. Target sequences can be selected from, for example, the sequence of ROR1, Genebank accession number: NM 005012. Searches of the human genome database (BLAST) can be carried out to ensure that selected siRNA sequence will not target other gene transcripts. Techniques for selecting target sequences for siRNA are given, for example, in Elbashir et al. ((2001) Nature 411, 494-498). Thus, the sense strand of the present siRNA comprises a nucleotide sequence identical to any contiguous stretch of about 19 to about 25 nucleotides in the target mRNA of ROR1. Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon.

Antisense

In certain therapeutic embodiments, the ROR1 antagonist is an antisense oligonucleotide. The levels of ROR1 can be down-regulated by administering to the patient a therapeutically effective amount of an antisense oligonucleotide specific for ROR1 mRNA. The antisense oligonucleotide specific for ROR1 mRNA may span the region adjacent to the initiation site of ROR1 translation.

An effective amount of the antisense oligonucleotide specific for ROR1 mRNA as isolated in a purified form may is generally that amount capable of inhibiting the production of ROR1 or reducing the amount produced or the rate of production of ROR1 such that a reduction in symptoms of lymphoma occurs. Antisense oligonucleotides can be administered via intravitreous injection at a concentration of about 10 μg/day to about 3 mg/day. For example, administered dosage can be about 30 μg/day to about 300 μg/day. As another example, ROR1 antisense oligonucleotide can be administered at about 100 μg/day. Administration of antisense oligonucleotides can occur as a single event or over a time course of treatment. For example, ROR1 antisense oligonucleotides can be injected daily, weekly, bi-weekly, or monthly. Time course of treatment can be from about a week to about a year or more. In one example, ROR1 antisense oligonucleotides are injected daily for one month. In another example, antisense oligonucleotides are injected weekly for about 10 weeks. In a further example, ROR1 antisense oligonucleotides are injected every 6 weeks for 48 weeks.

In various embodiments of the invention regarding antisense oligonucleotides, such as siRNAs and antisense nucleic acid molecules, the molecules are directed to SEQ ID NO: 1 or a homologue thereof. Thus the molecule may be directed to the coding or non-coding strand comprising DNA or may be RNA and directed to the mRNA transcript of the transcribed ROR1 gene. Accordingly, the molecule may specifically bind and inhibit expression of ROR1 and include at least a 10 nucleotide fragment of SEQ ID NO: 1 or complement thereof. For example, the molecule can be DNA or RNA and include at least a 10, 11, 12, 13, 14, 15, 16, 17, 18, 19, 20 or greater nucleotide fragment of SEQ ID NO: 17 or/and complement thereof, having a total length of about 10, 15, 20, 25, 30, 35, 40, 45, or 50 nucleotides.

Vaccines

As will be clear from the description herein of anti-ROR1 antibody, the present invention also provides for use of ROR1 in vaccines against diseases, such as a lymphoma, e.g., CLL, that involve the expression of ROR1. Because normal adult tissues do not appear to express ROR1, it represents a tumor-specific antigen that can be targeted in active immune therapy. For example, the levels of ROR1 can be down-regulated by administering to the patient a therapeutically effective amount of a ROR1 polynucleotide or polypeptide that produces in animals a protective or therapeutic immune response against ROR1 and the effects of its expression. The vaccines, can include polynucleotides or polypeptides. Methods of using such polynucleotides and/or polypeptides include use in vaccines and for generating antibodies against the polypeptides, such as those expressed by the polynucleotides. The polynucleotides can be a ROR1 gene, or a variant or fragment thereof. The polypeptides can be a ROR1 protein, or a variant or fragment thereof. In certain aspects, the ROR1 polynucleotide fragment can be a fragment comprising a fragment of the ROR1 gene. Such polynucleotide fragments can be comprised by a vector. A cell can be transformed and/or transfected by such polynucleotides and vectors and in certain aspects, the polynucleotides and vectors can express polypeptides of the invention. Typically the vaccine composition includes a pharmaceutically acceptable carrier or diluent. The teachings of U.S. Pat. No. 6,287,569 to Kipps et al., incorporated herein by reference in its entirety, can readily be adapted by those of skill in the art to create the vaccines of the present invention.

When describing a vaccine, a "polynucleotide variant" refers to any degenerate nucleotide sequence. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence. For example, a variant polynucleotide consisting of 80, 81, 82, 83, 84, 85, 86, 87, 88, 89, 90, 91, 92, 93, 94, 95, 96, 97, 98, and 99% to the polynucleotide consisting of ibpA. A "polynucleotide fragment" of a ROR1 polynucleotide is a portion of a ROR1 polynucleotide that is less than full-length and comprises at least a minimum length capable of hybridizing specifically with a native ROR1 polynucleotide under stringent hybridization conditions. The length of such a fragment is preferably at least 15 nucleotides, more preferably at least 20 nucleotides, and most preferably at least 30 nucleotides of a native ibpA polynucleotide sequence. A "polypeptide variant" refers to a polypeptide of differs in amino acid sequence from the ibpA polypeptide. Generally, differences are limited so that the sequences of the reference polypeptide and the variant are closely similar overall and, in many regions, identical. A variant polypeptide may differ in amino acid sequence by one or more substitutions, additions, deletions in any combination. A substituted or inserted amino acid residue may or may not be one encoded by the genetic code. Finally, a "polypeptide fragment" refers to any polypeptide of a portion of a ibpA polypeptide that is less than full-length (e.g., a polypeptide consisting of 5, 10, 15, 20, 30, 40, 50, 75, 100 or more amino acids of a native ROR1 protein), and preferably retains at least one functional activity of a native ROR1 protein.

DNA Vaccines for ROR1

Polypeptides with Arg at their N-terminus have a shorter half-life in the cytosol than those with a Met residue, provided that the polypeptide has a lysine residue to function as an ubiquitin acceptor site, spaced within 20 amino acids of the N-terminus. Plasmids encoding antigens targeted for rapid degradation by the proteasome are more effective than plasmids encoding the native protein in inducing CTL responses against cells expressing the target antigen.

Vectors have been constructed that encode a chimeric ROR1 protein with ubiquitin located at the amino terminus separated from ROR1 by an intervening codon for Met, and one with a codon for the destabilizing amino acid Arg and an in-frame insert of a segment of lacI. This segment contains a lysine residue spaced optimally from the N-terminus. Both constructs contain a sequence from the ubiquitine gene (SEQ ID NO: 8), followed by methionine or arginine sequence, followed by a LacI sequence (SEQ ID NO: 9), and finally followed by the ROR1 cDNA sequence (SEQ ID NO: 10). As detailed further in Example 16, the constructs are useful in ROR1 DNA vaccines, with the arginine construct being expected to cause rapid degradation of the protein and thus a more predominant cellular immune response.

Many embodiments of the invention are provided through well known protocols established in the art. For example, the following references provide multiple protocols which may be adapted for use with anti-ROR1 antibody: Vernon, S. K., Lawrence, W. C., Long, C. A., Cohen, G. H., and Rubin, B. A. Herpesvirus vaccine development: Studies of virus morphological components. In New Trends and Developments in Vaccines, ed. by A. Voller and H. Friedman. Chapter 13, pp. 179-210. MTP Press, Ltd., Lancaster (1978); Sambrook et al. (1989) Molecular Cloning—A Laboratory Manual (2nd ed.) Vol. 1-3, Cold Spring Harbor Laboratory, Cold Spring Harbor Press, N.Y., ("Sambrook"); and Current Protocols in Molecular Biology, F. M. Ausubel et al., eds., Current Protocols, a joint venture between Greene Publishing Associates, Inc. and John Wiley & Sons, Inc., (e.g., current through 1999, e.g., at least through supplement 37) ("Ausubel")), each of which are incorporated herein by reference in its entirety. With respect to vaccine technologies, U.S. Patent Application Nos. 20040253240 and 20030124141, are incorporated herein by reference in their entirety. These references also provide one of skill in the art instructions how to make and use the polynucleotides and polypeptides of the present invention for active and passive vaccines. Those of skill in the art will readily recognize how to adapt the disclosures of these references to the present polynucleotides and polypeptides of the present invention.

Kits

In carrying out various assay, diagnostic, and therapeutic methods of the invention, it is desirable to prepare in advance kits comprises a combination of an anti-ROR1 antibody or purified anti-sera as described herein with other materials. For example, in the case of sandwich enzyme immunoassays, kits of the invention may contain a monoclonal antibody that specifically binds ROR1 optionally linked to an appropriate carrier, a freeze-dried preparation or a solution of an enzyme-labeled monoclonal antibody which can bind to the same antigen together with the monoclonal antibody or of a polyclonal antibody labeled with the enzyme in the same manner, a standard solution of purified ROR1, a buffer solution, a washing solution, pipettes, a reaction container and the like. In addition, the kits optionally include labeling and/or instructional materials providing directions (i.e., protocols) for the practice of the methods described herein in an assay environment. While the instructional materials typically comprise written or printed materials, they are not limited to such. Any medium capable of storing such instructions and communicating them to an end user is contemplated. Such media include, but are not limited to electronic storage media (e.g., magnetic discs, tapes, cartridges, chips), optical media (e.g., CD ROM), and the like. Such media may include addresses to internet sites that provide such instructional materials.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Demonstration of Production of Anti-Adenovirus Antibody

Chronic lymphocytic leukemia (CLL) CLL cells were transduced with replication-defective adenovirus encoding CD154 (Ad-CD154). The seven patients of the study all had progressive intermediate or high-risk CLL by the modified Rai criteria. All patients had performance status of 0 to 2, life expectancy of more than 3 months, and normal renal, hepatic, and pulmonary function on study entry. Ad-CD154 were prepared and transduced into CLL cells as described in Wierda et al. (2000) Blood 96, 2917-24; and Cantwell et al. (1996) Blood 88, 4676-83. Six patients received five intravenous infusions of 3-6× 10' autologous CLL cells that had been transduced ex vivo with a replication-defective, serotype-5 adenovirus encoding murine CD154. Sera, collected sequentially during the studies from these 6 patients, was examined. Before treatment 4 out of 6 patients had hypogammaglobulinemia and residual 2 patients also have relatively low titers of immunoglobulins. After completion of therapy total IgG and IgM were slightly increased, whereas serum levels of IgA were not detectably changed. (IgG; 656±297 to 940±487 p=0.04, IgA; 72±63 to 69±61 p=0.4, IgM; 38±21 to 74±48 p=0.07) (FIG. 1A).

Figure 1B:
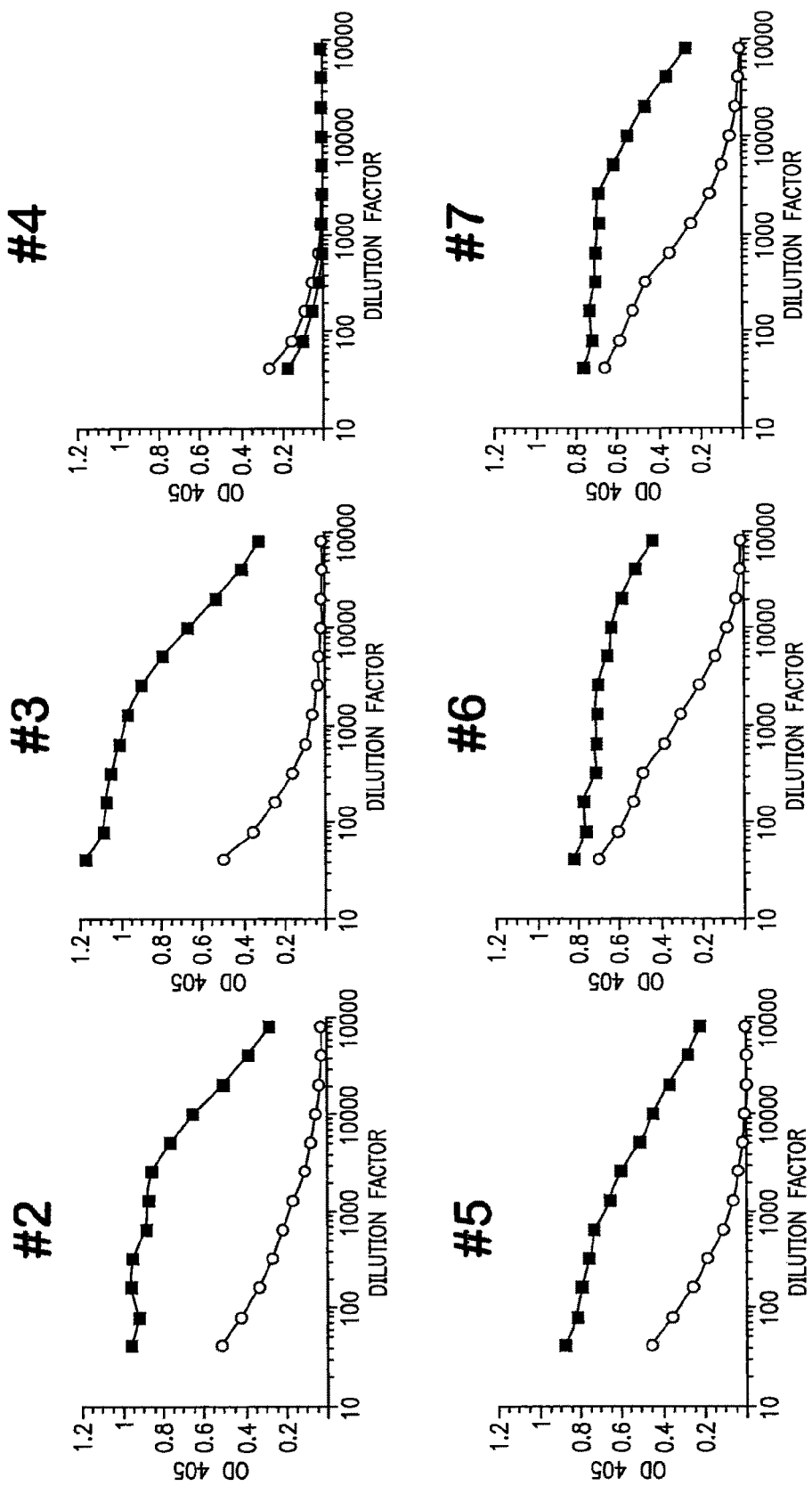
Figure 1C:
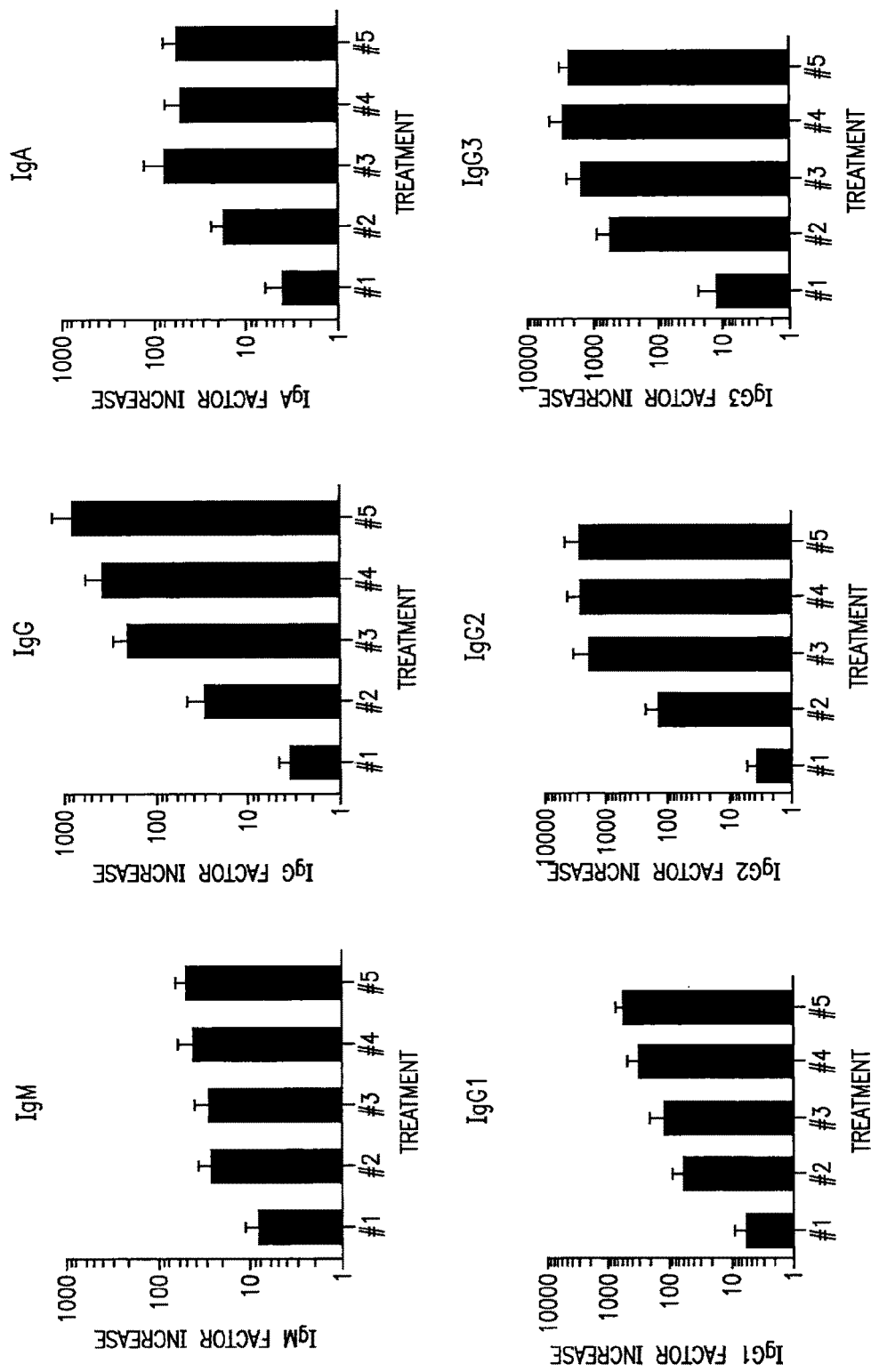
Figure 1D:
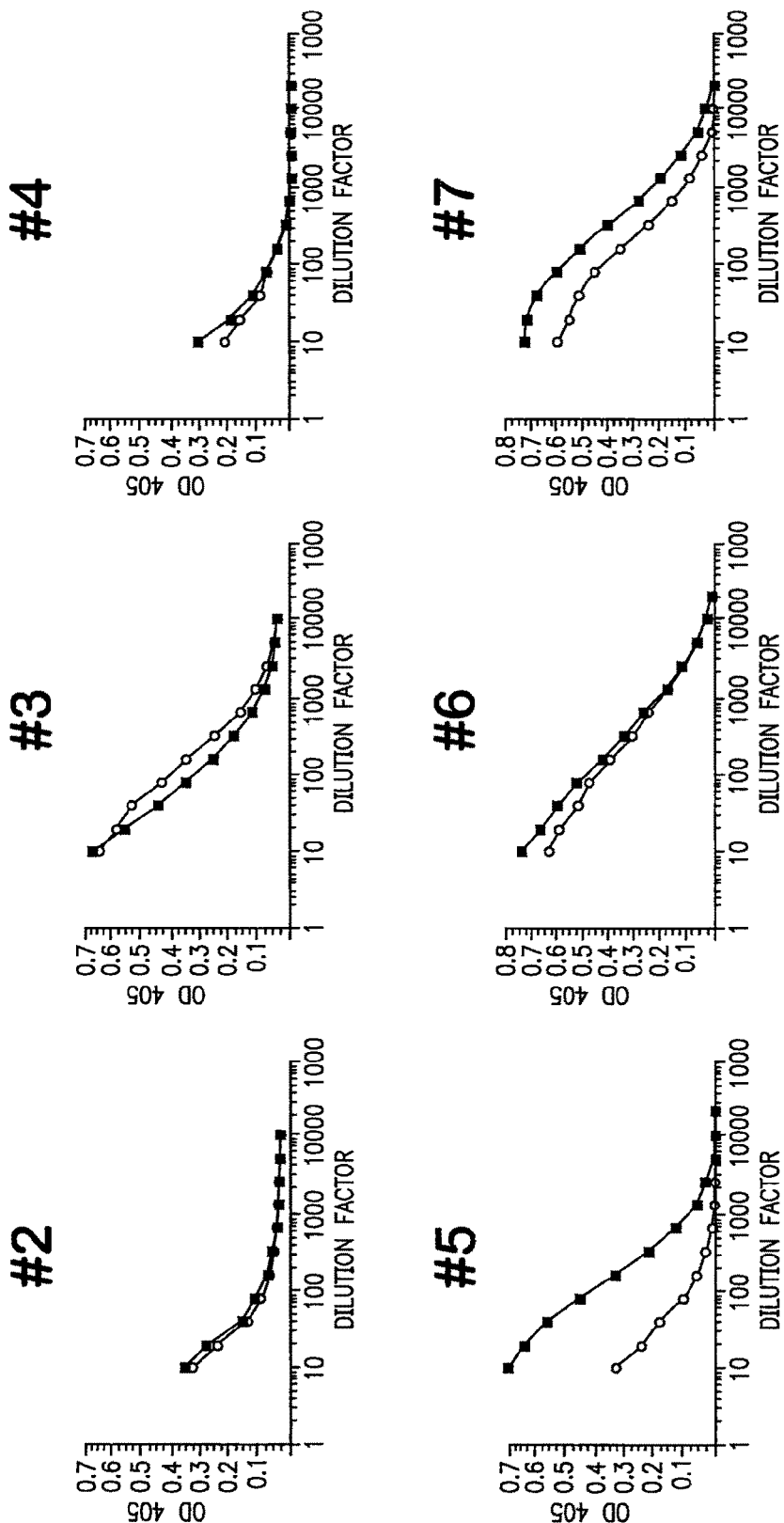

The antibody response was measured against the recombinant adenovirus used to transduce the CLL cells. Five of six patients had a vigorous polyclonal antibody response to adenovirus antigens following treatment (FIG. 1B). This response initially involved antibodies of the IgM class, and then subsequently antibodies of the IgG and IgA classes, but not IgE (FIG. 1C and not shown). On average, 50-fold, 60-fold, or nearly 1,000-fold increases in the titers of IgM, IgA, or IgG anti-adenovirus antibodies were observed, respectively. The IgG response involved antibodies of IgG1 and IgG3 isotypes (FIG. 1C), which primarily are observed in Th1-type immune responses. Moreover, no significant increases were observed in anti-adenovirus antibodies of the IgG4 isotype (data not shown), which typically are observed in Th2-type immune responses. Compared with this vigorous response, the increases in the titers of anti-tetanus toxin antibodies were not obvious unless patients received subsequent booster immunizations with tetanus toxoid. Patient #5 received tetanus toxoid after the second infusion of Ad-0154-transduced cells and had a greater than ten-fold increase in the serum titer of anti-tetanus toxoid 1 g following infusions of Ad-CD154-transduced cells (FIG. 1D). All other patients failed to increase their serum titers of anti-tetanus toxoid Ig by more than three-fold following treatment. None of the treated patients developed detectable autoantibodies against autologous red cells or platelets or allogeneic blood lymphocytes or human CD154 (data not shown). In addition, development of autoantibodies to red cells, platelets, or the human CD154 molecule following treatment was not observed.

Example 2

Flow Cytometry Analysis of Anti-CLL Activities

To analyze sera for IgG anti-CLL antibodies, the cells were stained with serial dilutions of antisera for 30 minutes at 4° C. in RPMI-1640 supplemented with 0.5% bovine serum albumin (BSA) (Staining media, SM). The cells were washed twice in SM and then counterstained with phycoerythrin (PE) or allophycocyanin (APC)-labeled mouse anti-human IgG, fluorescein-conjugated anti-CD3, and/or PE or APC-conjugated anti-CD19 or anti-CD5 for 30 minutes at 4° C. In others studies, CLL cells, CHO cells, and/or CHO-ROR1 cells were each stained with sera collected from treated patients or healthy adult donors, or antisera generated in mice that had been immunized against ROR1 via DNA immunization. Serial dilutions in SM were used to stain cells as noted for studies with human antisera, except that the cells were counterstained with fluorescein-conjugated goat-anti-mouse IgG or IgM (PharMingen). The washed cells were examined using a FACSCalibur™ (Becton Dickinson, Mountain View, Calif.) and the data analyzed with FlowJo™ software (Tree Star, San Carlos, Calif.). In most studies, CHO cells were stained with PKH26 (Sigma) prior to mixing them 1:1 with CHO-ROR1 cells. This allowed for simultaneous to discriminatation of differences in antisera staining of non-transfected, PKH26-labeled CHO cells versus non-labeled CHO-ROR1 cells using flow cytometry.

To examine the capacity of the 4A5 anti-ROR1 mAb to bind human cells, the isolated mAb and an IgG2b isotype control mAb of irrelevant specificity were conjugated with Alexa Fluor™ 647 (Molecular Probes, Invitrogen). The mean fluorescence intensity ratio (MFIR) was assessed to define the specific staining intensity of 4A5 each sample. The MFIR is the mean fluorescence intensity of cells stained with 4A5 divided by the mean fluorescence intensity of the same cell population stained with fluorochrome-conjugated IgG2b mAb of irrelevant specificity. Intracellular staining for the zeta-associated protein of 70 kDa (ZAP-70) was also preformed.

Anti-CLL activities were determined by flow cytometry. Peripheral blood mononuclear cells (PBMC) from IgG negative CLL case or healthy donor were incubated with one-fifth diluted serum from the patient or healthy donor, and bound IgG was detected by mouse anti-human IgG antibody (Pharmingn). B cells (CD19+CD3−) were gated using anti-CD19 antibodies conjugated APC and anti-CD3 antibody conjugated with FITC.

Example 3

ROR1 Anti-Sera Production

Anti-ROR1 mouse sera by means of DNA vaccination with ROR1 expression vector. Eight-week old Balb/c female mice were injected intradermally with 100 µg of ROR1 cDNA (Origene) with 50 µg of GM-CSF and CD154 expression vector as adjuvants. After 3 courses of injection, sera was collected from the mice. Chinese hamster ovary cells (CHO) were obtained from the American-type Tissue Culture Collection (ATCC, Manassas, Va.).

To generate CHO-ROR1, CHO-ROR1-rIgG, or CHO-Wnt5a cells, the CHO cells were transfected with pROR1, pROR1-rIgG, or pWnt5a, respectively, using lipofectamine 2000 (Invitrogen). The cells transfected with pROR1 or pROR1-rIgG were cultured in Dulbecco Modified Eagle's Minimal Essential Medium™ (DMEM, Gibco, Rockville, Md.) supplemented with 10% fetal calf serum (FCS) for 24 hours and then placed in media containing G418 (250 pg/ml) or Zeocin™ (300 pg/ml) (Invitrogen, Carlsbad, Calif.) for selection of stable transfectants that have acquired neomycin or Zeocin™ resistance, respectively. Following selection, the cells were cloned by limiting dilution and evaluated for expression of ROR1 or ROR1-rIgG by immunoblot analysis. Stable, subcloned CHO-ROR1-rIg transfectant cells were adapted to suspension culture in IMGX II medium (HyClone, Logan, Utah). Suspended CHO-ROR1-rIg cells were cultured in ProCHO-5 medium (Cambrex Bio Science, Baltimore, Md.), and recombinant ROR1-rIg was purified from the culture supernatant using protein A sepharose (Pierce Biotechnology, Rockford, Ill.). The purity of the isolated protein was assessed by polyacrylamide gel electrophoresis (PAGE) and immunoblot analysis. The K8.1 glycoprotein of Kaposi sarcoma-associated herpes virus protein fused with the rabbit Ig (rIg) Fc recombinant protein (K8.1A-rIg), was used as a control recombinant rIg protein. Stable CHO-ROR1 or CHO-Wnt5a transfectants were subcloned by limiting dilution and examined for expression of ROR1 or Wnt5a by immunoblot analysis (data not shown).

The spleen cells of mice immunized with pROR1 and found to make high-titer anti-ROR1 antisera were used to generate mAb-producing hybridomas. For this the splenocytes were fused with P3-X63-Ag8 in polyethylene glycol and subsequently selected in media containing hypoxanthine, aminopterin, and thymine (HAT medium). One hybridoma, designated 4A5, produced IgG2b anti-ROR1 mAb.

CHO cells with or without transfection with ROR1 cDNA cloned into pcDNA3 vector by lipofectamine 2000 (Invitrogen) was used to determine the titer of anti-ROR1 antibody in serum. Bound antibody from immunized mice was detected by flow cytometry using anti-mouse antibody with fluorescence (Pharmingen). To distinguish the untransfected CHO from transfectants in the mixture, it was stained with PKH26 (Sigma) according to the manufacture's protocol. Anti-ROR1 activity was determined by incubating CHO transfectants and serum from patient followed by detection with anti-human Ig labeled with fluorescence (Southern Biotech).

The generated antisera reacted specifically with the human ROR1-rIg recombinant protein but not control K8.1A-rIg recombinant rIg by ELISA (data not shown). These anti-ROR1-antisera, but not the pre-immunization sera, reacted with the CLL cells from each of 8 patients tested, but not with the lymphocytes of healthy donors (N=3) (data not shown). Splenocytes from mice with high-titer anti-ROR1 antisera were used to generate hybridomas with P3-X63-Ag8. One hybridoma, designated 4A5, produced mouse IgG2b mAb specific for the extracellular domain of ROR1.

Figure 16:
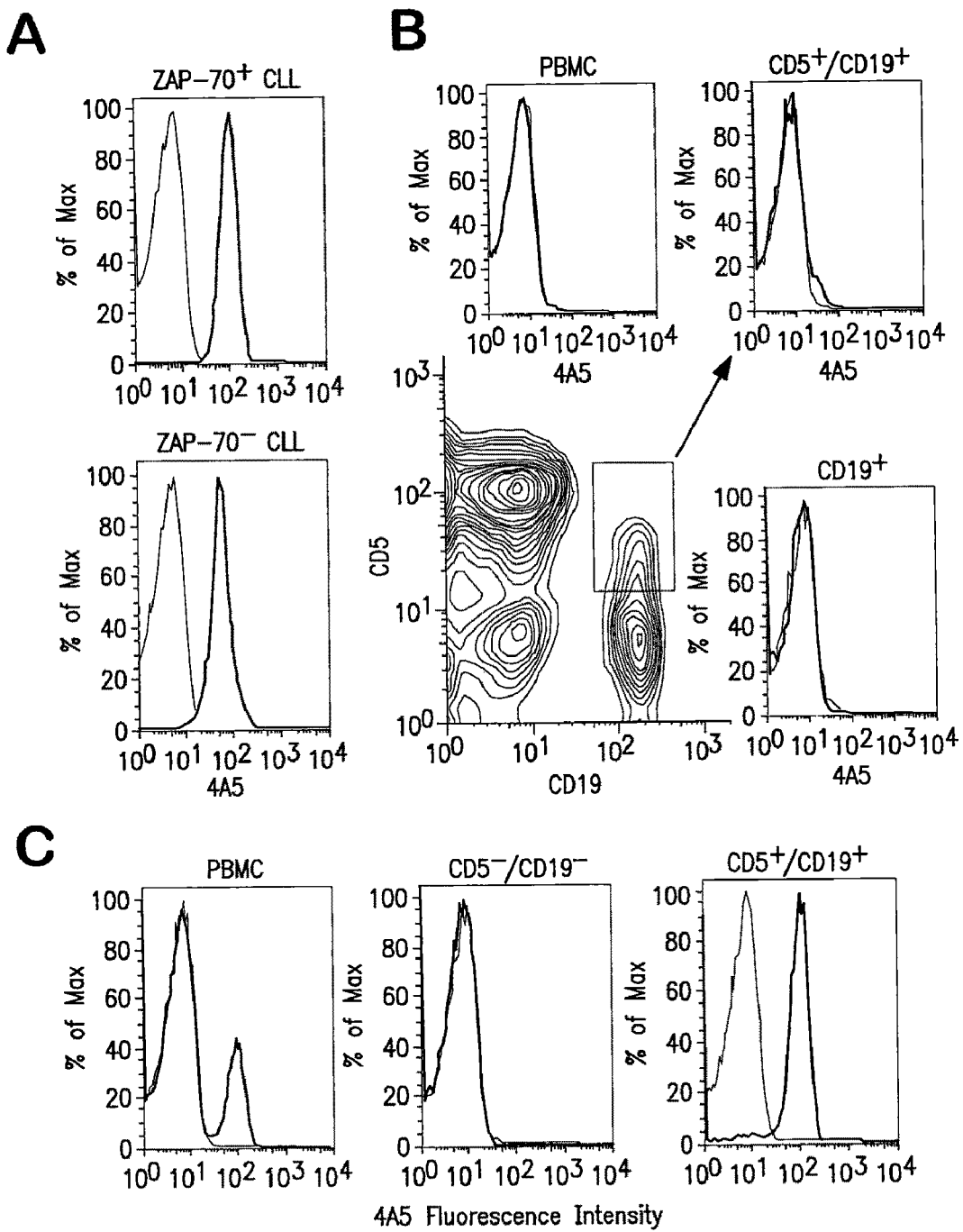
FIG. 16A depicts histograms depicting the fluorescence of CLL cells stained with 4A5 or an IgG2b isotype control antibody of irrelevant specificity.
FIG. 16B shows staining of peripheral blood mononuclear cells (PBMC) of a normal healthy adult using 4A5 or the control IgG2b along with fluorochrome conjugated mAb specific for CD5, and CD19.
FIG. 16C depicts the PBMC of a patient with nascent stage 0 CLL. The left histogram (labeled "PBMC") depicts the fluorescence of the entire mononuclear cell population after staining with 4A5 or the isotype control IgG2b. The middle histogram provides the fluorescence of the gated CD19-negative cells when co-stained with the 4A5 or isotype control. The right histogram provides the fluorescence of the gated CD5+/CD19+ CLL cells when co-stained with the 4A5 or isotype control.

The Alexa-647-conjugated 4A5 mAb specifically stained CLL cells, but not non-leukemic leukocytes (FIG. 16). The fluorochrome-conjugated 4A5 mAb reacted with the $CD5^+$/$CD19^+$ CLL cells of each patient tested (N=69), allowing for resolution of leukemia versus non-leukemia cells by flow cytometry (FIG. 16A). The 4A5 mAb reacted with ZAP-70-positive CLL samples with similar intensity as with ZAP-70-negative CLL samples. For 4A5-stained ZAP-70-positive cases (N=33), the average mean fluorescence intensity ratio (MFIR) was 12.0±4.4 (S.D.) and the median MFIR was 12.2, with MFIR values ranging from 2.6 to 21.2. For 4A5-stained ZAP-70-negative CLL cases (N=36), the average MFIR was 12.4±5.5 (S.D.) and the median MFIR was 12.0, with MFIR values ranging from 2.4 to 25.8. In contrast, the 4A5 mAb failed to react with the blood lymphocytes of healthy donors, including normal blood B cells or $CD5^+$/$CD19^+$ blood B cells (FIG. 16B). For 4A5-stained normal blood B cells of unrelated donors (N=10) the average MFIR was 0.9±0.1 (S.D.) and the median MFIR was 0.9, with MFIR values ranging from 0.8 to 1.3. The 4A5 mAb also did not react with non-leukemic blood mononuclear cells of patients with CLL, allowing for the single-color detection of CD5+/CD23+/CD19+, light-chain restricted leukemia cell subpopulations in the blood of patients with early-stage disease (FIG. 16C). Similarly, the 4A5 mAb failed to react with non-leukemia marrow mononuclear cells, allowing for the single-color detection of CLL cells in the marrow of patients with minimal residual disease after therapy (data not shown).

Example 4

ELISA

To produce recombinant ROR1 protein, its extracellular region was cloned into the pcDNA3-zeocin vector encoding rabbit IgG Fc region in frame. Stable CHO transfectant (CHO-ROR1rIg) was made with this vector, and was adapted to suspension culture using IMGX II medium (HyClone).

Suspended CHO-ROR1rIg was cultured in ProCHO-5 medium, and rROR1rIg was purified using protein A sepharose (Pierce).

For ELISA, 5 μg/ml ROR1-rIg (at 5 pg/ml in phosphate buffered saline, pH 7.4, (PBS)), rabbit Ig (rIg) (at 5 pg/ml in PBS), or $10^8$/ml adenovirus that had previously been heated to 65° C. for 15 minutes was absorbed in a 96 well plate overnight at 4° C. After washing and blocking with 2% BSA/PBS, serum dilutions of antisera were added and incubated for 1 hour at room temperature. Goat anti-human Ig, IgG, IgA, IgM, IgG1, IgG2, IgG3 and IgG4 conjugated with horseradish peroxidase (HRP) or alkaline phosphatase (AP) (Southern Biotechnology, Birmingham, Ala.) were used as secondary antibody. TMB (KPL, Gaithersburg, Md.) or pNPP (Sigma) was used for substrate for HRP and AP respectively. All experiments were done duplicate and were shown the average.

Example 5

Analysis of Microarray Data

Gene expression profiles of normal human tissues were obtained from the data series GSE803 of Gene Expression Omnibus™ (GEO) database. The gene set of CLL signature genes were made according to the published papers Klein et al. (2001) J Exp Med 194, 1625-38; Rosenwald et al. (2001) J Exp Med 194, 1639-47. The data were clustered and visualized with GeneSpring™ software (Silicon Genetics).

Example 6

Immunoblotting

Total cell lysates were made by incubation cells in a lysis buffer containing 1% Triton X-100, 50 mM Tris-HCl (pH 7.5), 100 mM NaCl, 50 mM NaF, 5 mM EDTA, 40 mM glycerophosphate, 1 mM sodium orthovanadate, with complete protease inhibitor mix (Roche). Cell lysates were separated 7.5% or 5-15% gradient SDS-PAGE and blotted on Immobilon-P membrane (Millipore). For immunoblot, rabbit (Cell signaling) or goat (R&D) anti-ROR1 antibodies were used followed with anti-rabbit or anti-goat antibodies conjugated with HRP (Santa Cruz). Conditioned medium of culture with CHO with or without transfection with HA-tagged Wnt5a cDNA (Upstate) was incubated with 1 μg of ROR1rIg or rabbit IgG followed by immunoprecipitation with anti-HA matrix (Roche) or protein A/G agarose (SantaCruz). Bound proteins were immunoblotted with anti-HA (Roche) or anti-rabbit Ig antibody.

Example 7

Reporter Assay

A reporter assay was performed as described in Lu et al. (2004) Proc Natl Acad Sci USA 101, 3118-23. Briefly, HEK293 cells were transfected in 12-well plates by using FuGENE™ (Roche, Mannheim, Germany), and 0.5 μg of reporter plasmid, 0.1-0.2 μg of the control plasmid pCMXβ-gal, 100-200 ng of the various expression plasmids, and carrier DNA pBluescriptKSII, for a total of 1 μg per well. The luciferase values were normalized for variations in transfection efficiency by using the β-galactosidase internal control, and are expressed as fold stimulation of luciferase activity, compared with the designated control cultures. All of the transfection results are representative of a minimum of three independent transfections.

Example 8

Induction of Humoral Immunity Against CLL Cell

The production of anti-adenovirus antibody suggests the induction of humoral immunity against the CLL cell itself. Allogeneic CLL cells were incubated with serum from patient before and after treatment. Antibody binding was checked by flow cytometry.

Figure 2A:
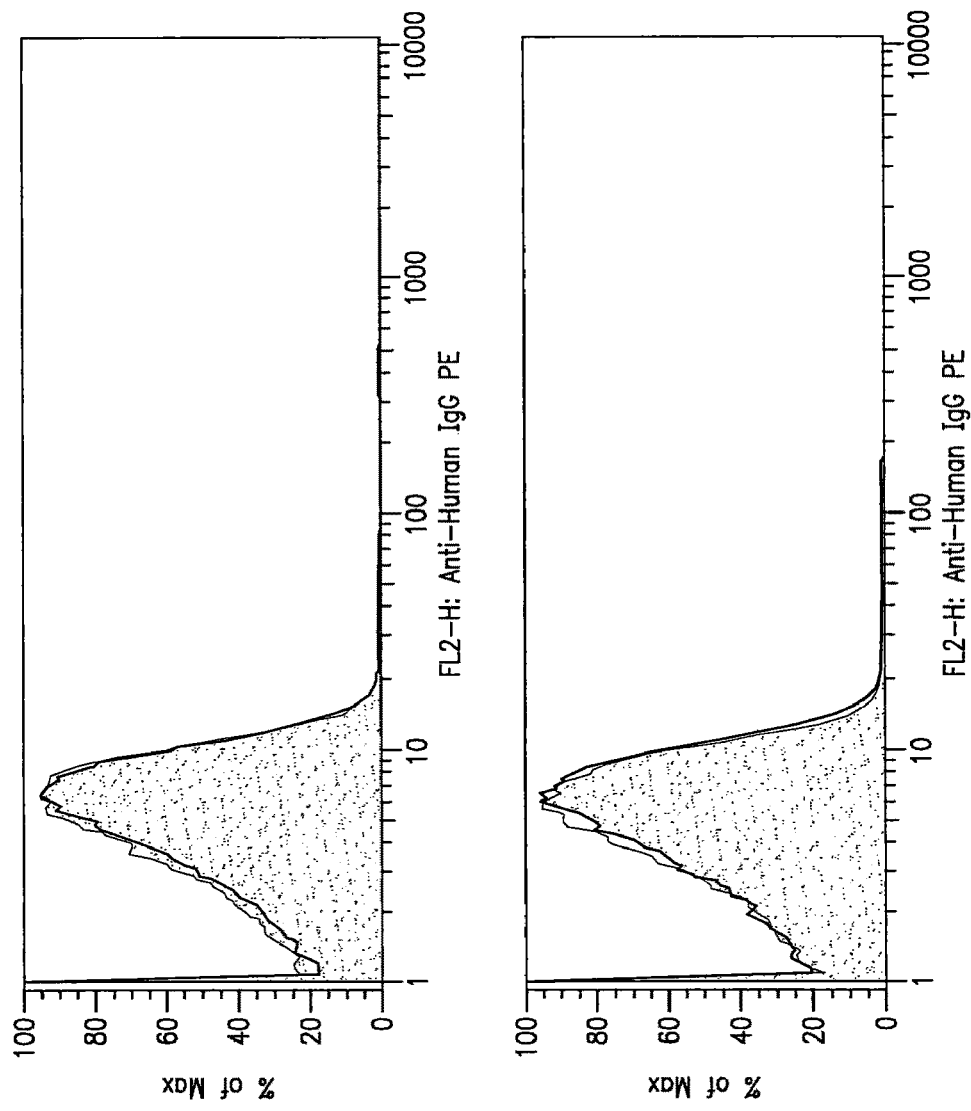
FIGS. 2A through 2B are a series of histograms showing antibody production against surface molecules on CLL B cells by Ad-CD154 therapy. Antibody bound on CD19+ CD3- cells were detected by goat anti-human antibody.
Figure 2B:
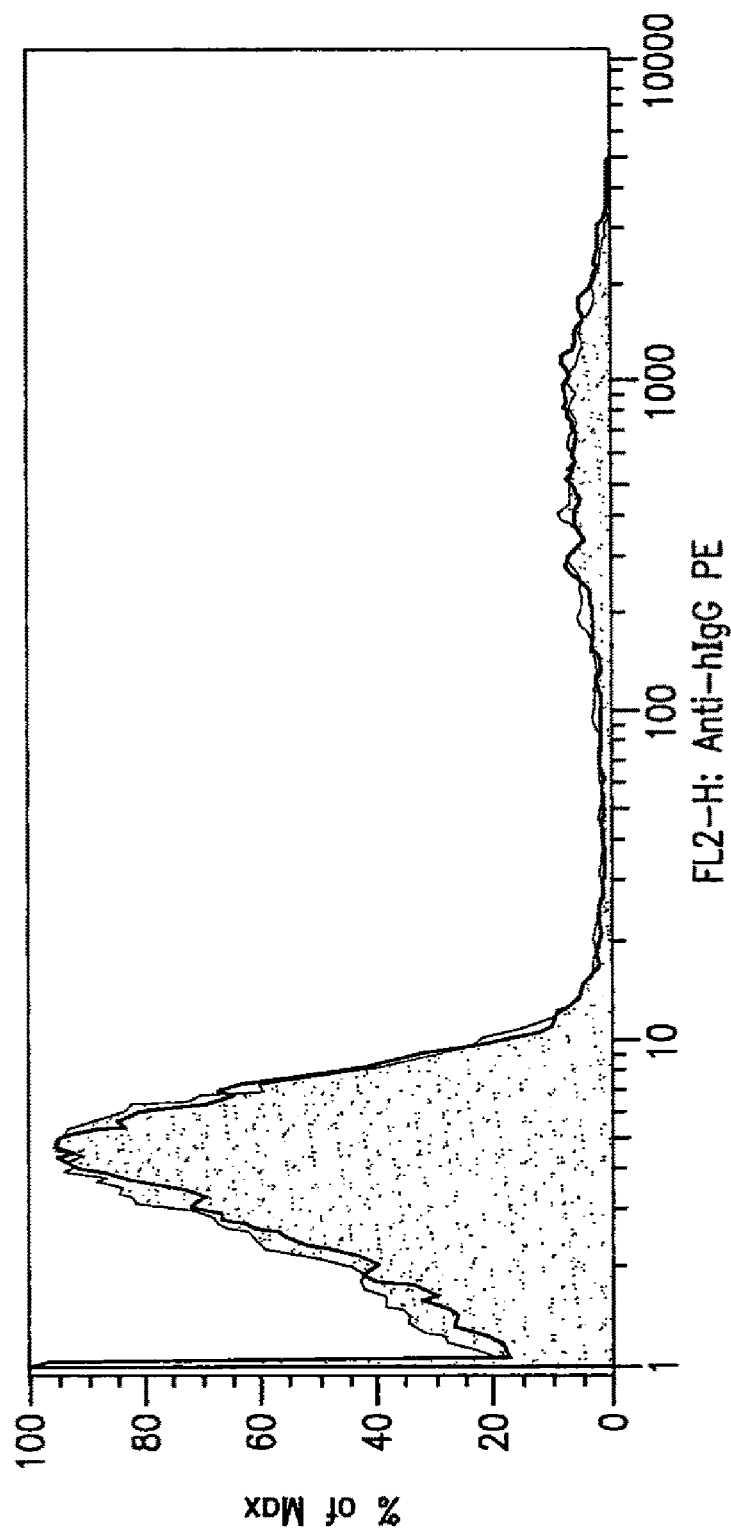
Figure 2B:
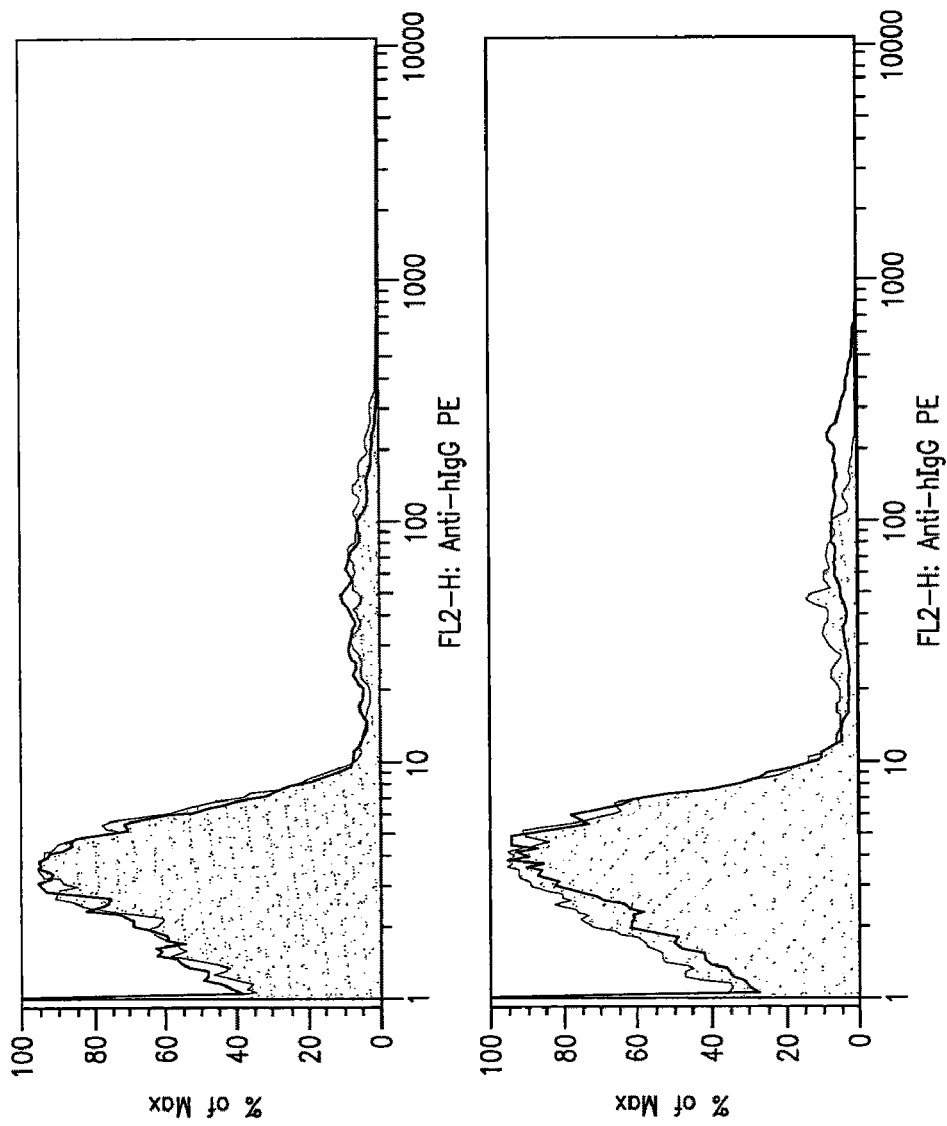
Figure 2B:
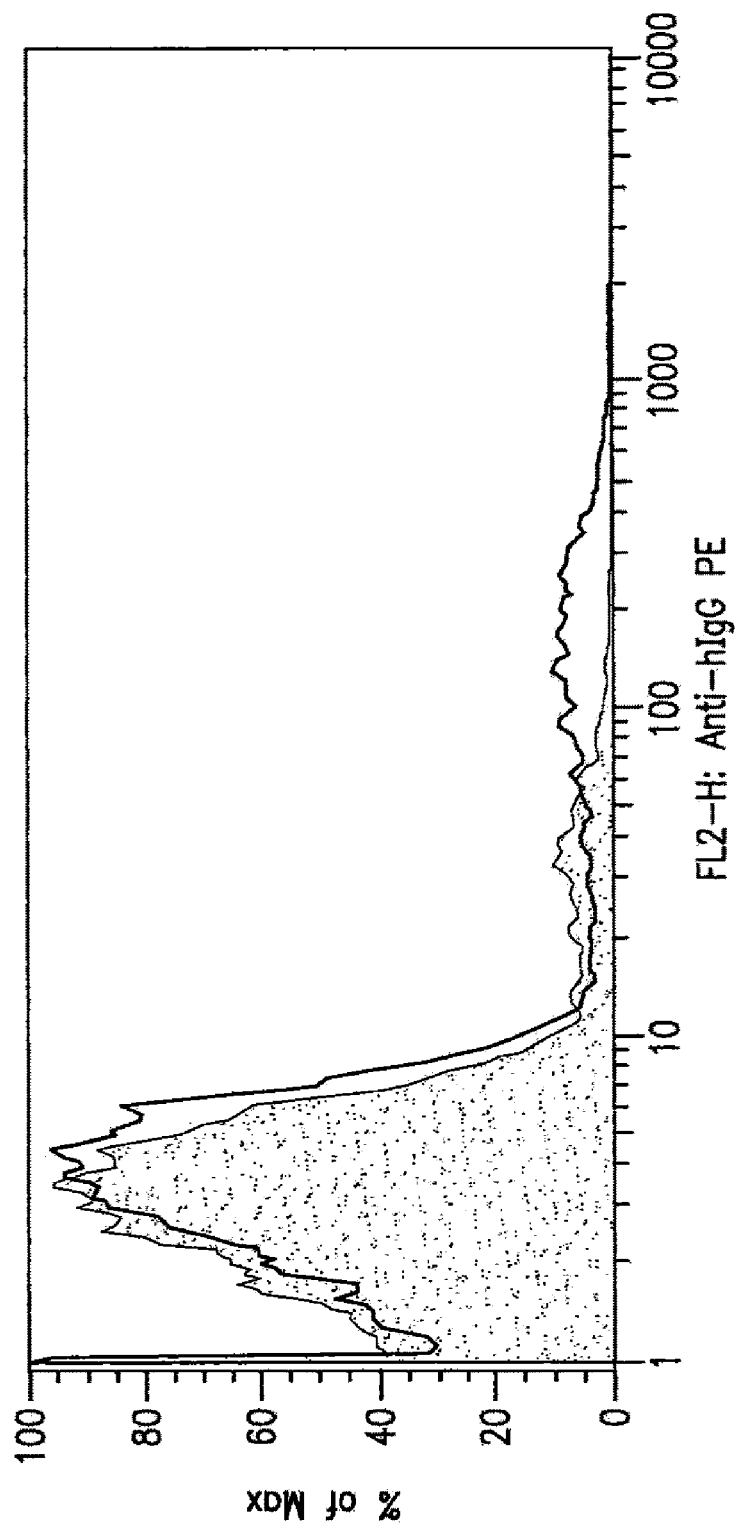

Results showed that the sera from 3 patients after Ad-CD154 therapy had the reactivity against CLL B cells compared with the sera before therapy (FIG. 2A). The shift of the histograms were reproducible with another 3 CLL B cells, and it was not detectable against B cells from healthy donors (FIG. 2B). This data suggests a TAA(s) may exist on the surface of CLL cells in a hidden fashion from surveillance of immunity, becoming immunogenic after CLL received the immune-costimulatory molecules.

However, when we incubated allogeneic, IgG-negative CLL cells with serial dilutions of each sera we found that three patients (#5, #6, and #7) had IgG reactive with CLL cells after treatment that were detectable at serum dilutions of up to 1/32. This reactivity was not detected in the pre-treatment sera of any patient or the sera of healthy control donors (n=6) (FIG. 15A, and data not shown).

The microarray analyses of CLL samples identified the relatively small number of genes that are differentially expressed in CLL cells in compared with normal B cell subsets and another types of B cell malignancies. Klein et al. (2001) J Exp Med 194, 1625-38; Rosenwald et al. (2001) J Exp Med 194, 1639-47. These CLL signature genes are candidates for TAAs of CLL. The expressions of these genes were examined in normal human tissues because where there is an abundant expression in normal tissue, antibody production against such a gene cannot occur in vivo. The expression profiles of CLL signature genes in normal adult tissues wad determined (data not shown). Genes that had low expressions in all tissues were spotlighted. Attention was directed to receptor tyrosine kinase ROR1 gene, because it is a probable cell surface molecule and is expressed mainly in developing cells. Yoda et al. (2003) J Recept Signal Transduct Res 23, 1-15; Al-Shawi et al. (2001) Dev Genes Evol 211, 161-71; Matsuda et al. (2001) Mech Dev 105, 153-6 (2001).

Example 9

Immunoblot

Cell lysates were prepared for immunoblot analyses using sera from patients before and after treatment. Total cell lysates were made by incubation cells in a RIP lysis buffer containing 1% Triton X-100, 50 mM Tris-HCl (pH 7.5), 100 mM NaCl, 50 mM NaF, 5 mM ethylenediaminetetraacetic acid with protease inhibitors (10 pg/mL aprotinin, 10 pg/mL leupeptin, 10 pg/mL pepstatin, and 1 mM phenylmethylsulfonyl fluoride), and phosphatase inhibitors (40 mM glycerophosphate and 1 mM sodium orthovanadate) (Roche, Basel, CH). Cell lysates were separated on a 7.5% or 5-15% gradient SDS-PAGE and transferred onto Immobilon-P™ membranes (Millipore, Billerica, Mass.). Non-specific binding sites were blocked by incubating the membranes with 10% powdered milk for 2 hours at room temperature prior to treating the membranes with patient sera (diluted 1:10 in phosphate buffered saline (PBS) containing 5% fetal bovine serum (FBS)) or with rabbit (Cell Signaling Technology, Boston, Mass.) or goat (R&D Systems, Minneapolis, Minn.) anti-ROR1-peptide antibodies in 5% FBS for overnight incubation at 4° C. Antibodies to human Wnt5a (Cell Signaling Technologies, Danvers, Mass.) were used for detection of Wnt5a in stable CHO-Wnt5a transfectants. For detection of membrane-bound human, rabbit, or goat IgG, the washed membranes respectively were incubated with mouse anti-human IgG, anti-rabbit Ig, or anti-goat Ig that was conjugated to horseradish peroxidase (HRP) (Santa Cruz Biotechnology) for subsequent development with Super Signal West Femto Chemiluminescent Substrate™ (Pierce) for autoradiography with Super RX™ film (Fuji, Tokyo, Japan).

None of the pre-treatment sera reacted selectively with lysates prepared from CLL cells (FIG. 15B, and data not shown). However, the post-treatment sera that reacted with CLL cells in the flow cytometry assay also reacted with a protein of ~125 kD in lysates of CLL cells that was not apparent in lysates of normal blood lymphocytes (FIG. 15B).

Consistent with the assumption that patients #5, #6, and #7 developed IgG antibodies against ROR1, we found that their post-treatment sera, but not pre-treatment sera or sera from control donors (N=3), reacted with Chinese hamster ovary (CHO) cells transfected with a human ROR1 expression vector (CHO-ROR1), but not non-transfected CHO cells (FIG. 15A, and data not shown). Moreover, the positive post-treatment antisera reacted with a ~125 kD protein in lysates of CLL cells or CHO-ROR1 cells that was not detected in lysates from normal blood lymphocytes or CHO cells (FIG. 15C, and data not shown). This protein was larger than the predicted molecular size of the non-glycosylated polypeptide encoded by ROR1 (~102 kD), suggesting that the mature polypeptide expressed in CLL and CHO-ROR1 was glycosylated at deduced N-glycosylation sites.

Figure 3:
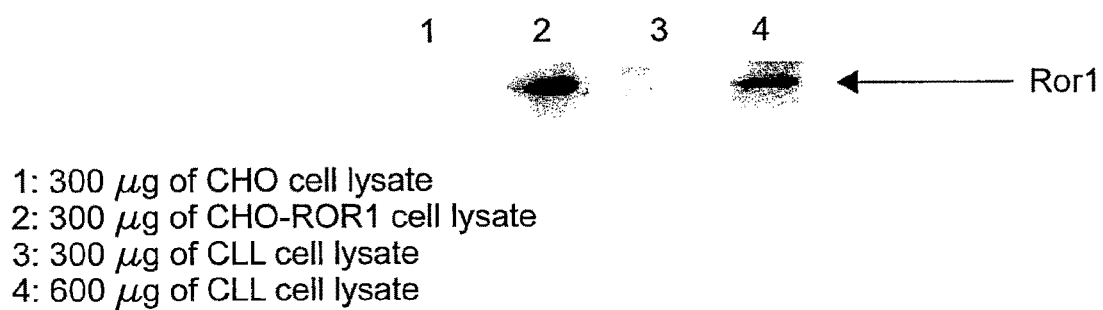
FIG. 3 is an immunoblot of immune precipitates of lysates with 4A5 probed with rabbit anti-ROR1 raised against ROR1 peptides.

FIG. 3 depicts an immunoblot demonstrating that the anti-ROR1 mAb (designated 4A5) can immune precipitate the ROR1 protein from cells made to express human ROR1 (e.g. Chinese Hamster Ovary (CHO)) cells or chronic lymphocytic leukemia (CLL) cells. Prior antibodies to ROR1 were not mAbs, were generated against peptides to ROR1, are of low affinity, and cannot immune precipitate the ROR1 protein. As such, the 4A5 mAb can be used to detect and/or isolate the ROR1 protein, which could have diagnostic, treatment, and/or investigative value.

Example 10

ROR1 Expression in CLL B Cells

The data from microarray gene-expression studies for a gene(s) used by CLL cells but not non-leukemia lymphocytes that could encode a cell surface protein that had a molecular size of ~125 kD were evaluated. Among these, attention was focused on on ROR1, a gene that encodes a cell-surface, orphan-receptor type I tyrosine kinase of greater than 100 kD.

Figure 4B:
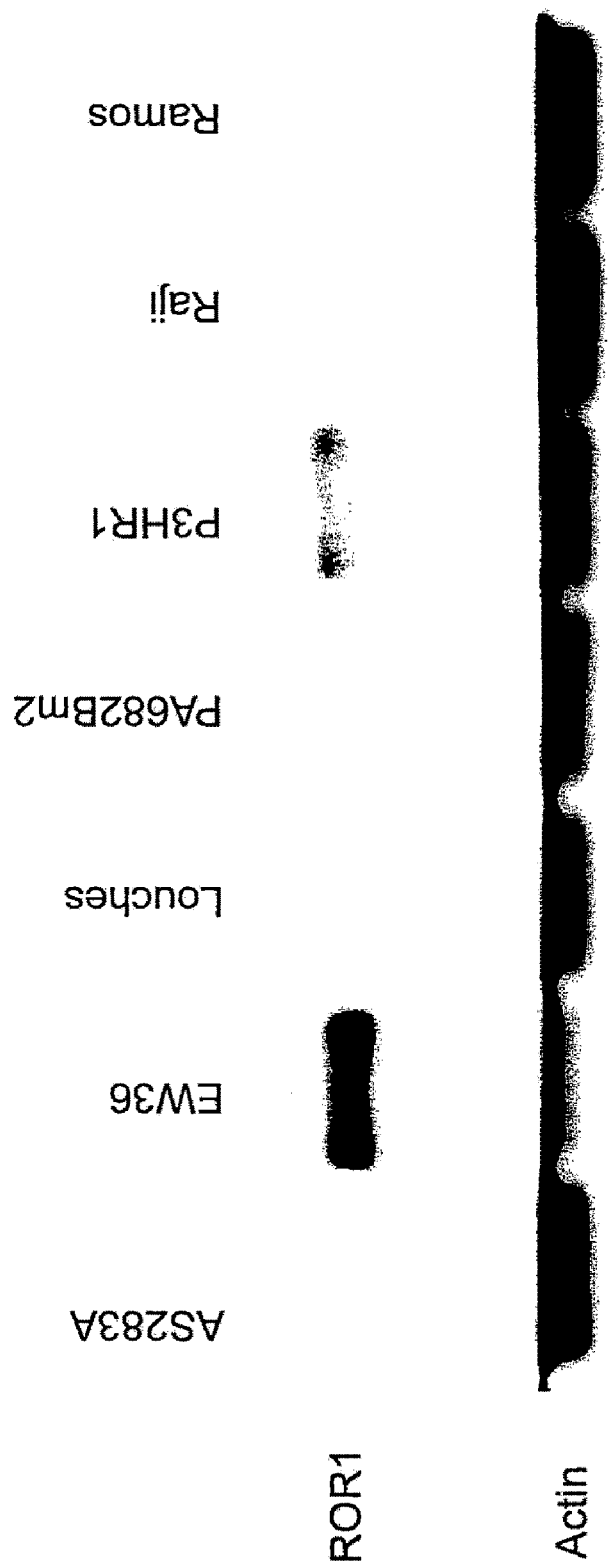

To confirm the ROR1 protein expression in CLL B cells, immunoblot analysis, as described above, using anti-ROR1 antibody was performed. Results showed that the bands at the level of 128 kD were detected in peripheral blood or splenocytes from CLL patients (FIG. 4A). The size is compatible with the reported murine ROR1 and bigger than deduced size of 101 kD from amino acid sequence without putative leader sequence probably due to the glycosylation29. This band could be detected neither in samples of peripheral blood from healthy donor nor splenocytes from idiopathic thrombocytopenia purpura patient. ROR1 protein was detectable also in some Burkitt's B cell lines at the same molecular weight (FIG. 4B).

Figure 17:
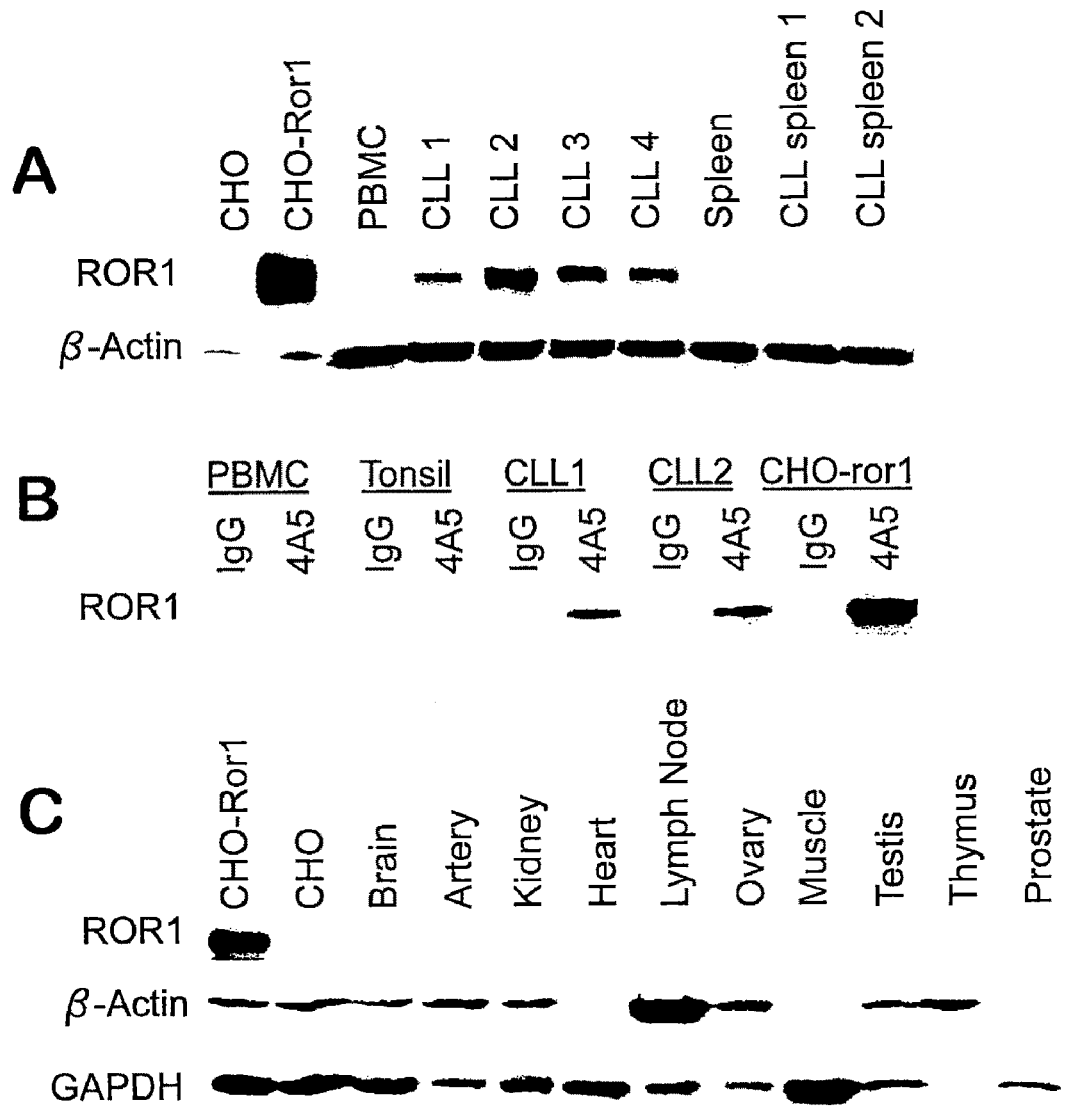
FIG. 17A depicts total cell lysates of CHO cells ("CHO"), CHO-ROR1 cells ("CHO-ROR1"), CLL blood mononuclear cells (CLL samples 1 through 4) or CLL splenocytes ("CLL spleen 1" and "CLL spleen 27, blood mononuclear cells of a healthy donor ("PBMC"), or non-neoplastic, normal human splenocytes ("Spleen") were examined by immunoblot analysis using rabbit anti-ROR1 anti-peptide antibody (top panel) or antibodies to p-actin to monitor for protein loading (bottom panel), as indicated to the left of each panel. The source of the tissue is indicated at the top of each lane.
FIG. 17B depicts an immunoblot of an immunoprecipitation of ROR1 using the 4A5 mAb. Cell lysates of normal donor PBMC, normal tonsil, CLL blood mononuclear cells ("CLLI" and "CLL2") or CHO-ROR1 cells were incubated with the 4A5 mAb or an IgG isotype control mAb for immune precipitation using *Staph* protein A. The immune precipitate was evaluated via immunoblot analysis using anti-ROR1 peptide antisera. This detected protein of 4 2 5 kD in 4A5 immune precipitates prepared from CLL cell samples or CHO-ROR1 cells, but not from blood or tonsillar lymphocytes of normal donors, or the isotype control immune precipitates from any source, as indicated at the top of each lane.
FIG. 17C depicts an immunoblot of cells lysates were prepared as indicated at the top of each lane for immunoblot analyses using anti-ROR1 antibodies (top panel) or antibodies specific for p-actin (middle panel) or GADPH (bottom panel).

Normal lymphoid tissues and isolated CLL cells of several patients were evaluated for expression of ROR1 by immunoblot analyses using anti-ROR1 antibodies generated against an N-terminal-region synthetic peptide corresponding to human ROR1. This analysis revealed a protein of ~125 kD in lysates from CLL cells or CHO-ROR1 cells, but not in lysates of non-transfected CHO cells, blood mononuclear cells of healthy donors, normal blood B lymphocytes, or splenocytes of patients who did not have CLL (FIGS. 4A, 17A, and data not shown). Furthermore, the 4A5 mAb could immunoprecipitate a protein of ~125 kD in lysates of CLL cells or CHO-ROR1 cells that reacted specifically with the anti-ROR1-peptide antisera (FIG. 17B). However, 4A5 could not immune precipitate this protein from lysates prepared from blood mononuclear cells or tonsillar lymphocytes of subjects who did not have CLL (FIG. 17B). Moreover, ROR1 was not detectable by immunoblot analyses in the cell lysates of any other adult tissue (e.g. brain, breast, colon, heart, kidney, lung, liver, pancreas, spleen, thymus, testis, tonsil, or vascular endothelium (FIG. 17C)).

Example 11

ROR1 cDNA Sequence

To isolate and sequencing of ROR1 cDNA, total cellular RNA was isolated from $1 \times 10^7$ CLL B cells using RNeasy™ reagents (Qiagen, Valencia, Calif.), per the manufacturer's instructions. First strand cDNA was synthesized from one-third of the total purified RNA using an oligo-dT primer and Superscript II™ RT (Invitrogen, Carlsbad Calif.). The remaining RNA was removed with RNase H and the cDNA purified using QIAquik™ purification columns (Qiagen). Three µl of cDNA was used for PCR amplification of ROR1 with 200 pM dNTPs, 3% DMSO, Phusion™ Hot Start DNA polymerase (New England Biolabs, Beverly, Mass.), 1× Phusion™ GC Buffer (New England Biolabs), and 250 pM each of oligonucleotide primers ROR1-F (5'-CGAGAGGAGGAATGCAC-3') (SEQ ID NO: 11) and ROR1-R (5'-ATACCACATTTACAAAAGTTGTG-3') (SEQ ID NO: 12). PCR cycling parameters were 98° C. for 2 min., followed by 35 cycles of 98° C. for 15 sec, 59° C. for 30 sec, and 72° C. for 1 min. The PCR products were size selected by electrophoresis in 0.8% agarose containing 0.5 pg/ml of ethidium bromide (Invitrogen), and the expected products were excised and purified using QlAquik purification columns (Qiagen). PCR products were sequenced directly using the fluorescence-dideoxy-chain-termination method and an Applied Biosystems™ 3730 automated nucleic acid sequence analyzer (ABI, Foster City, Calif.). Nucleotide sequences were analyzed using DNASTAR™ (Madison, Wis.) and compared with nucleotide and protein sequences deposited in the GenBank™ sequence databases using BLAST, and the cDNA reference sequence (accession #NM-005012).

The sequence of the ROR1 cDNA generated from the CLL cells of each of four unrelated patients was determined. The ROR1 cDNA of one patient (A50) was identical to that of the published ROR1 cDNA sequence (NM_05012). Two other cases (A364 and A377) had ROR1 cDNA sequences that were identical to each other, but had two nucleotide differences from NM_005012 at positions 1353 and 1553. While the substitution at position 1353 was conservative, the difference at position 1553 resulted in the substitution of threonine for methionine at amino acid 518 of the ROR1 polypeptide sequence. This appears to represent a genetic polymorphism, as the ROR1 cDNA of these two cases matched the annotated genomic DNA contigs identified in the human genome project. This assumption is supported by the ROR1 sequences of the fourth CLL sample (A332), which appeared to be heterozygous, as the CLL cells expressed equal amounts of both types of ROR1 mRNA.

Example 12

Cell Surface Localization of ROR1 Protein in CLL B Cells

Figure 4C:
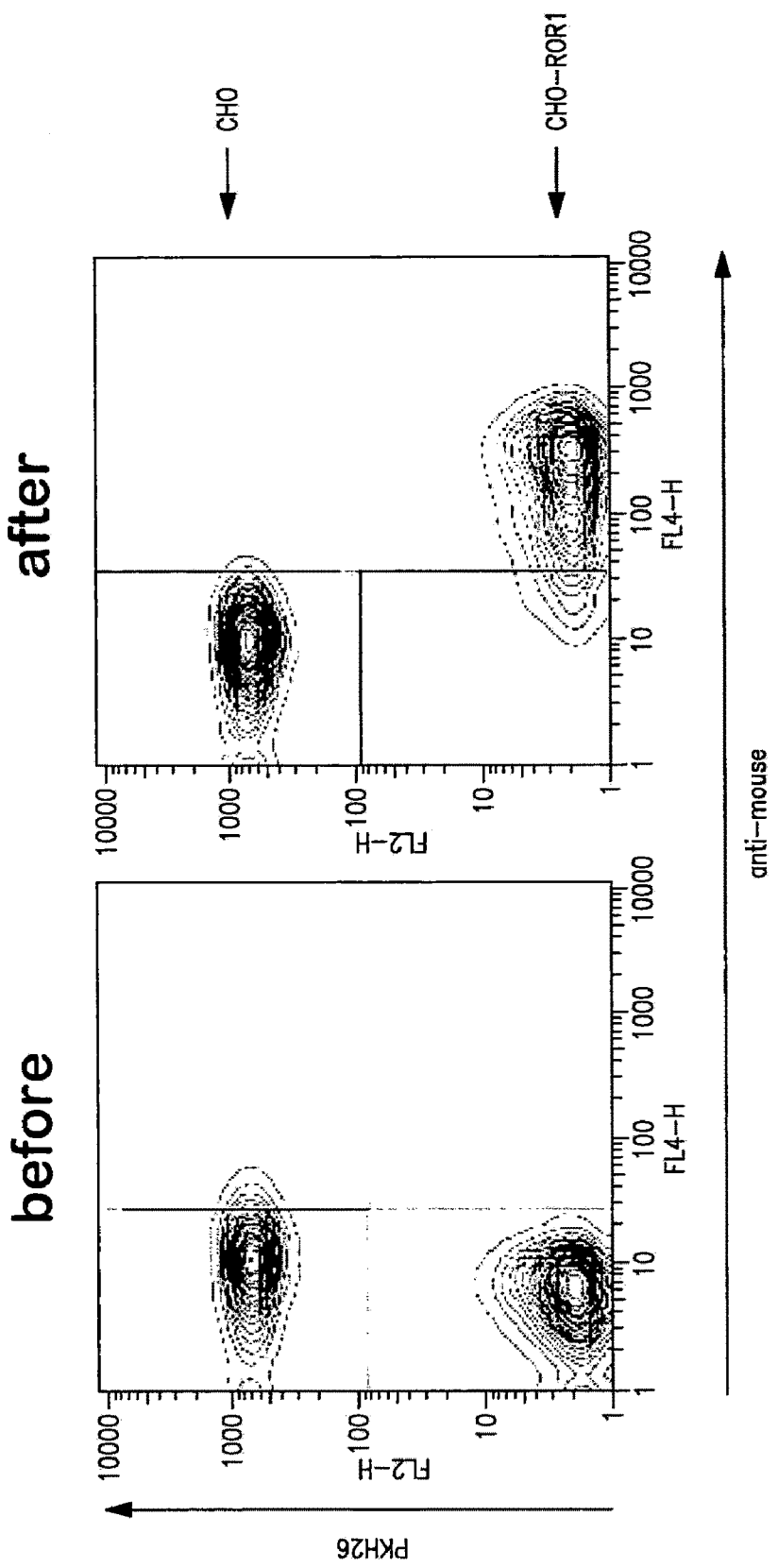

Cell surface localization of ROR1 protein in CLL B cells was confirmed via flow cytometry. Anti-ROR1 mouse sera, produced by means of DNA vaccination with ROR1 expression vector, as described above, was reacted with CHO transfected with ROR1 (CHO-ROR1) but not with CHO parental cell (FIG. 4C). Using this anti-serum, ROR1 expression was detected on cell surface of all CLL samples examined (n=8) but not on PBMC from healthy donors (n=3) (FIG. 4D).

Example 13

Induction of Anti-ROR1 Antibody by AD-CD154 Therapy

Figure 5A:
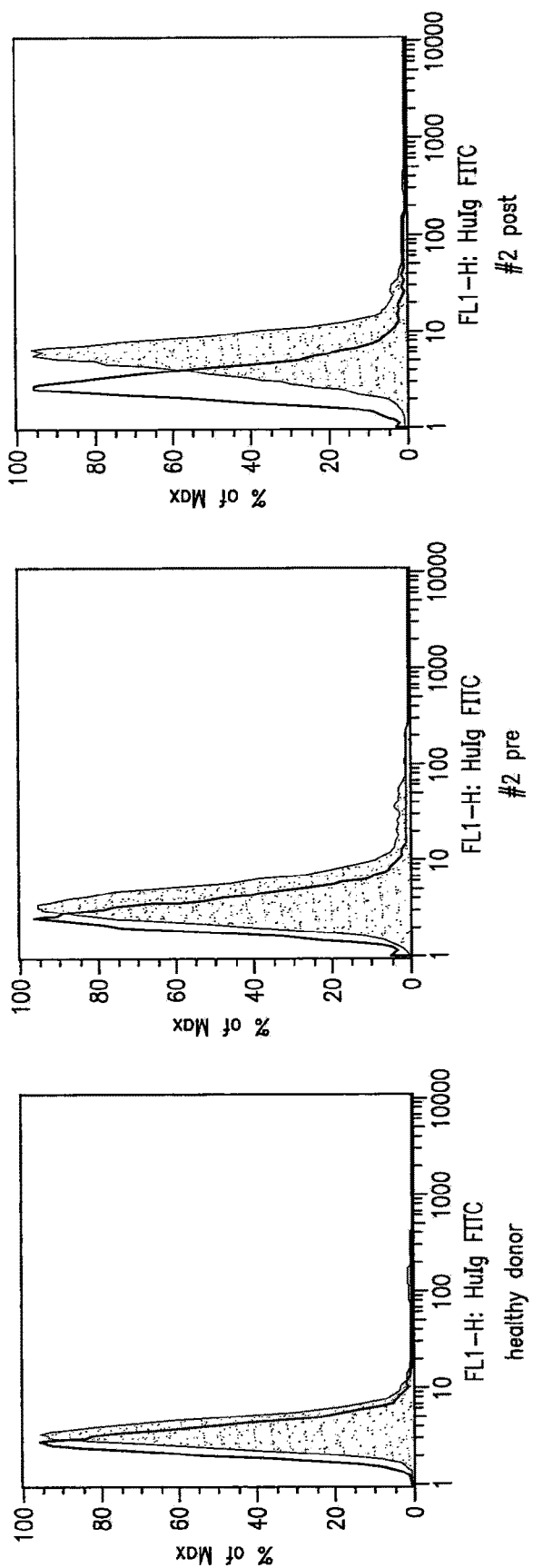
FIG. 5A is a series of histograms where CHO (open histograms) or CHO-ROR1 (shaded histograms) was incubated with serum from patients before (pre) or after (post) therapy. Histograms indicated the bound human Ig detected by PE labeled goat anti-human Ig.
Figure 5B:
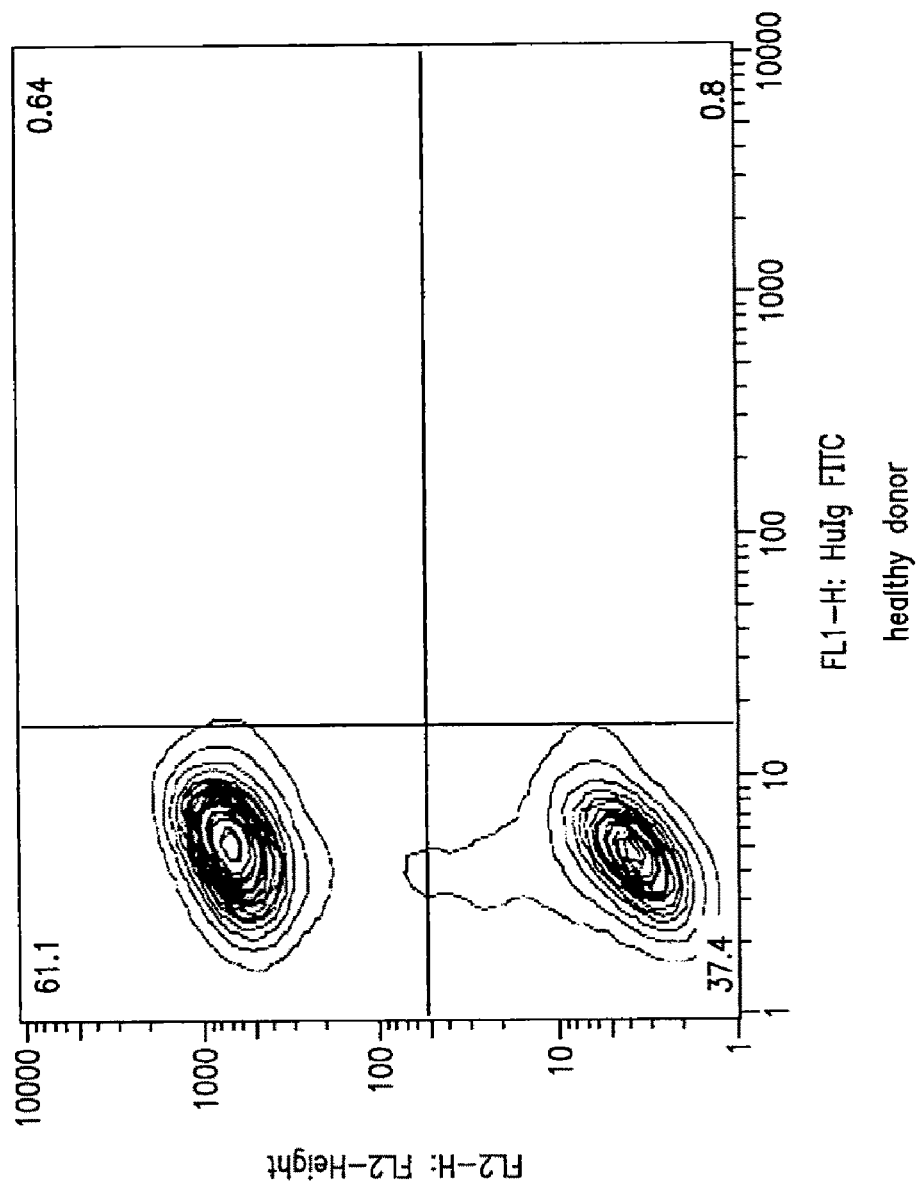
Figure 5B:
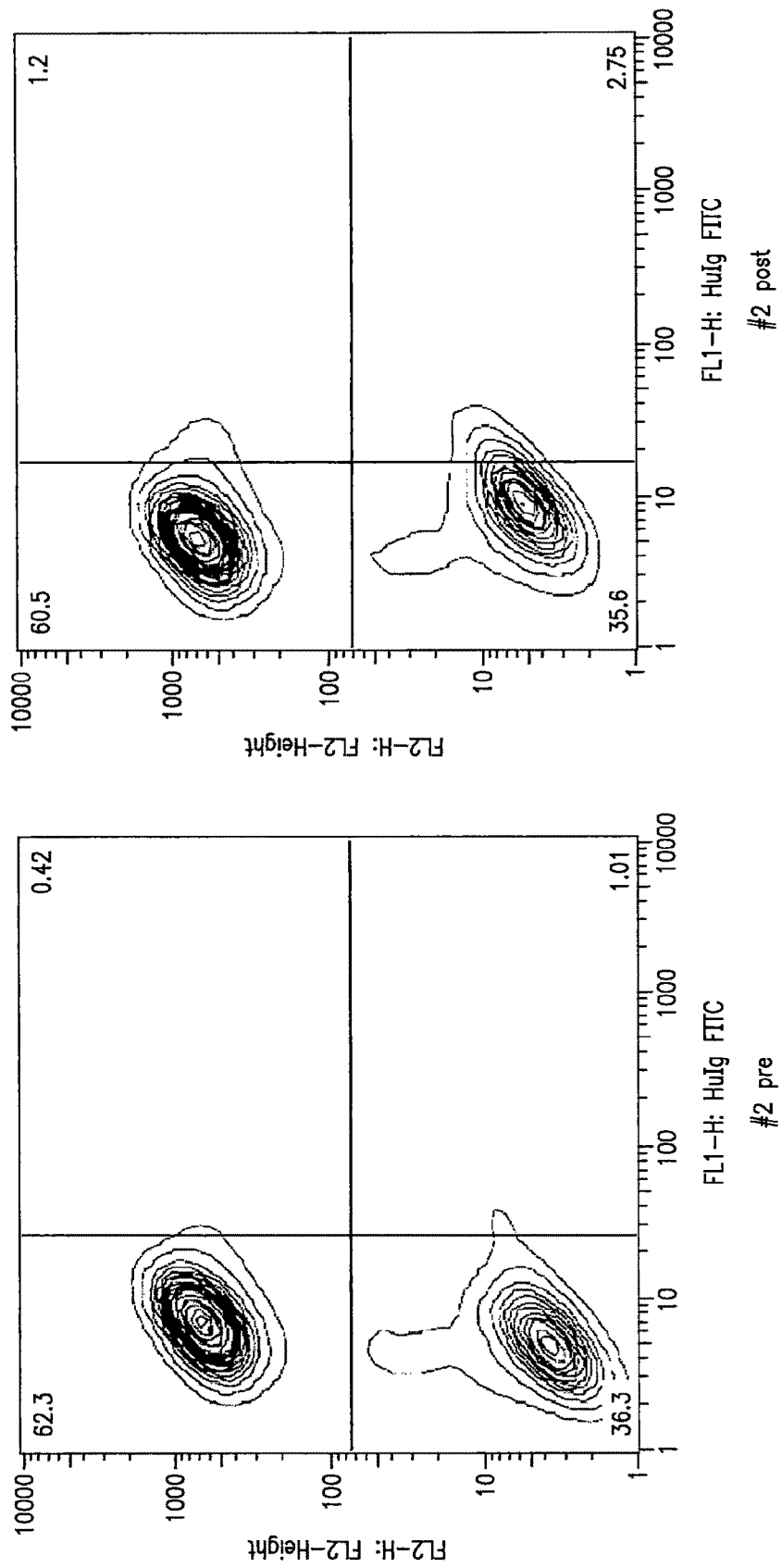
Figure 5B:
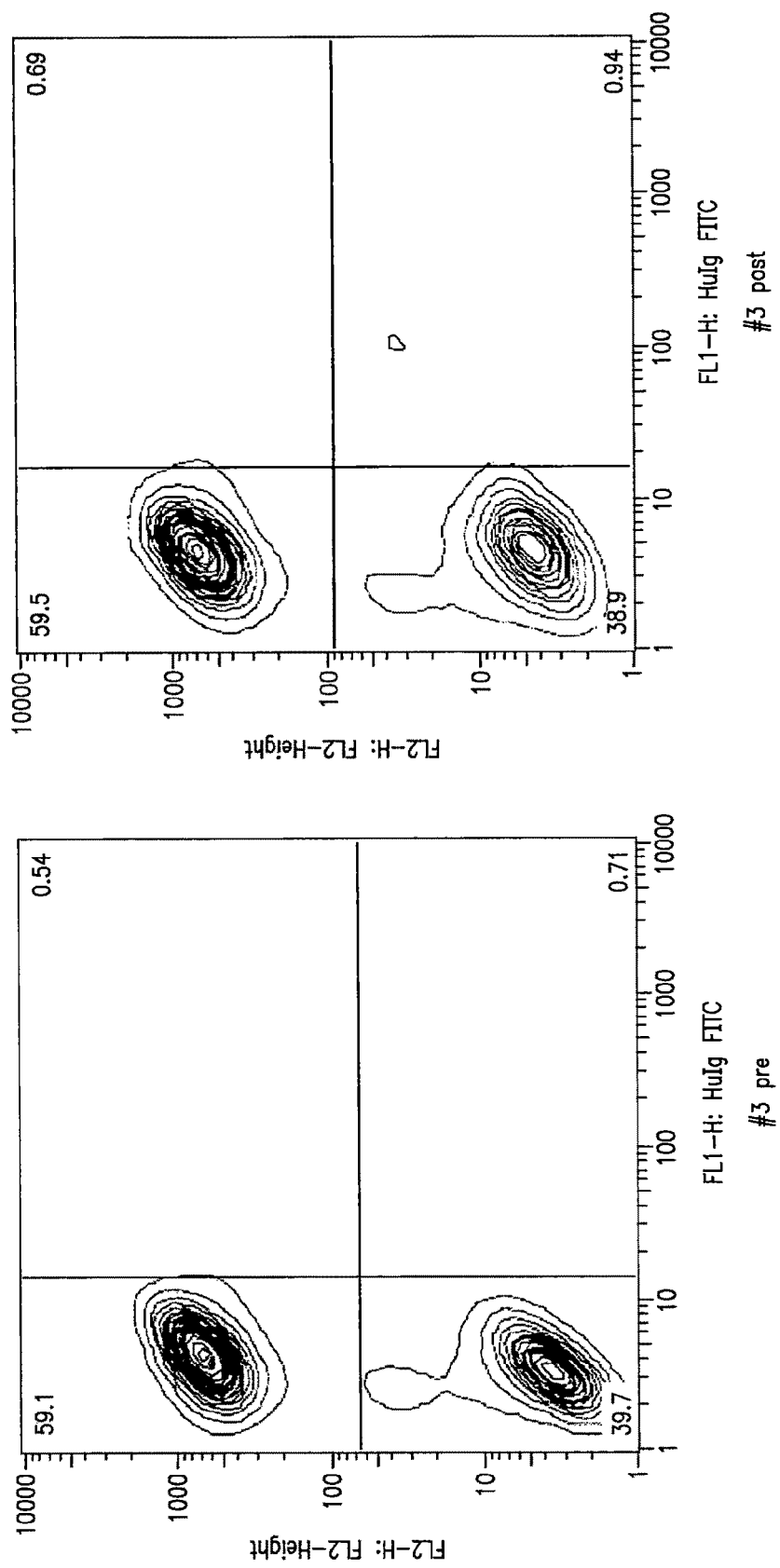
Figure 5B:
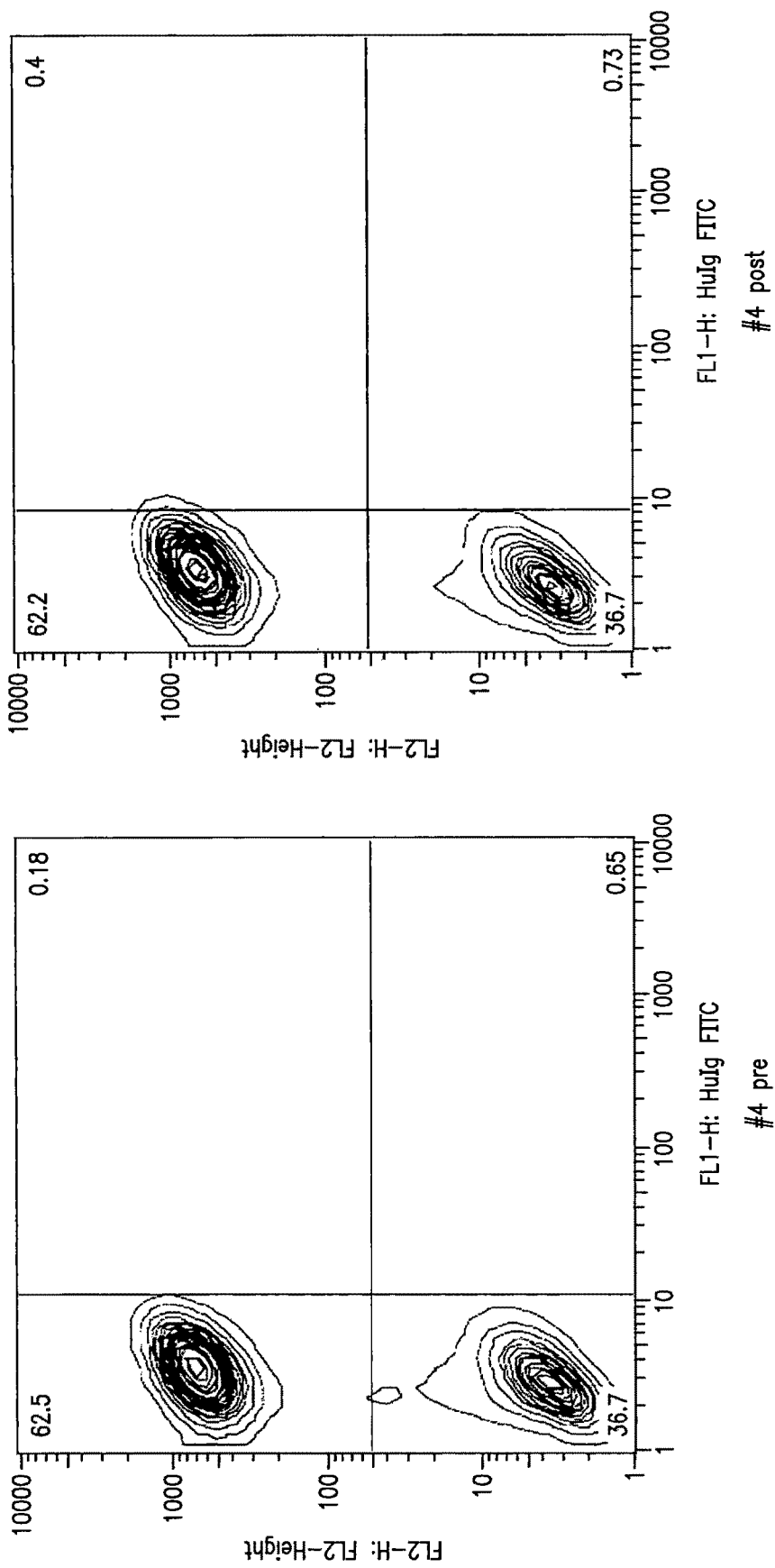
Figure 5B:
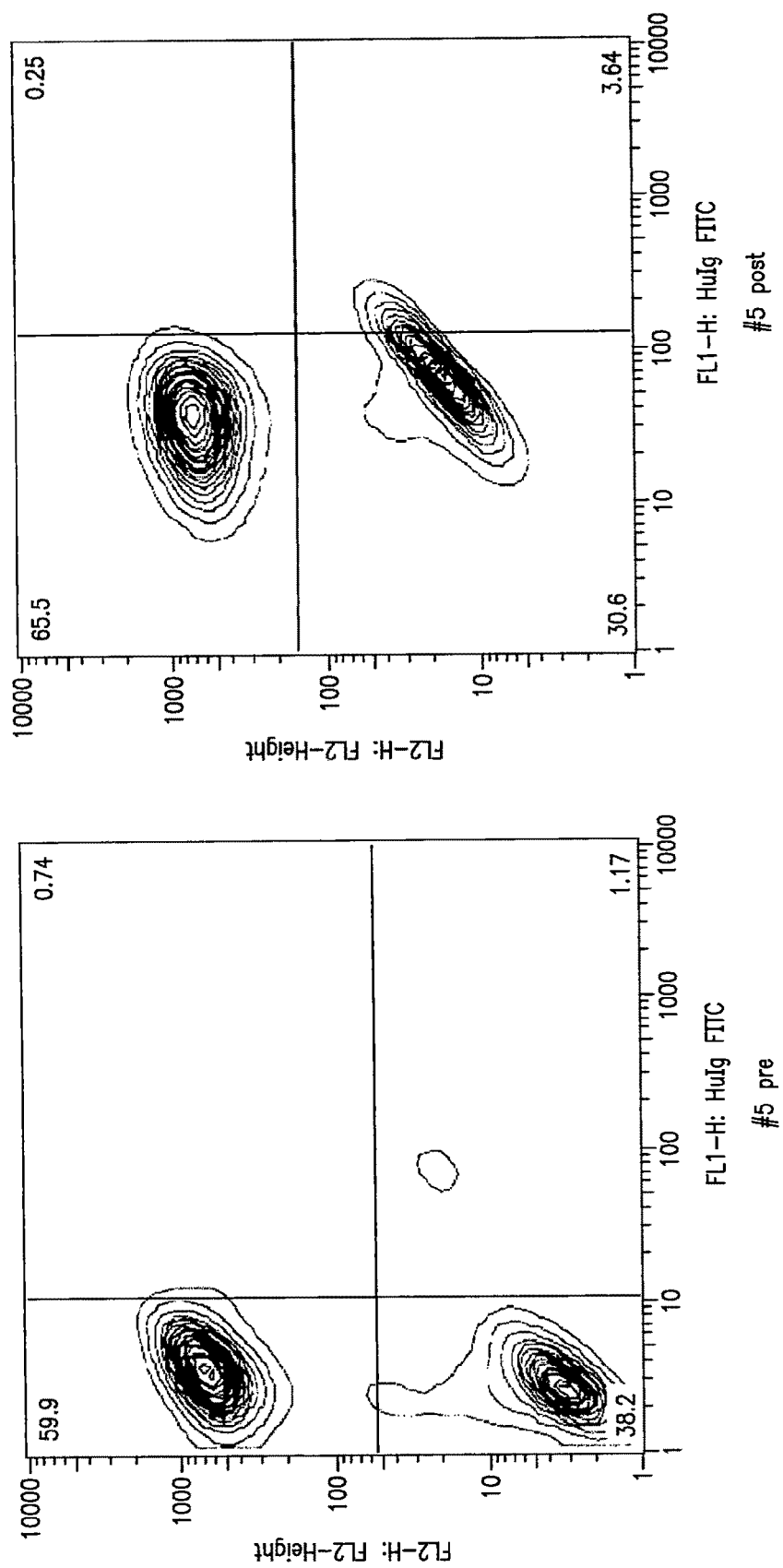
Figure 5B:
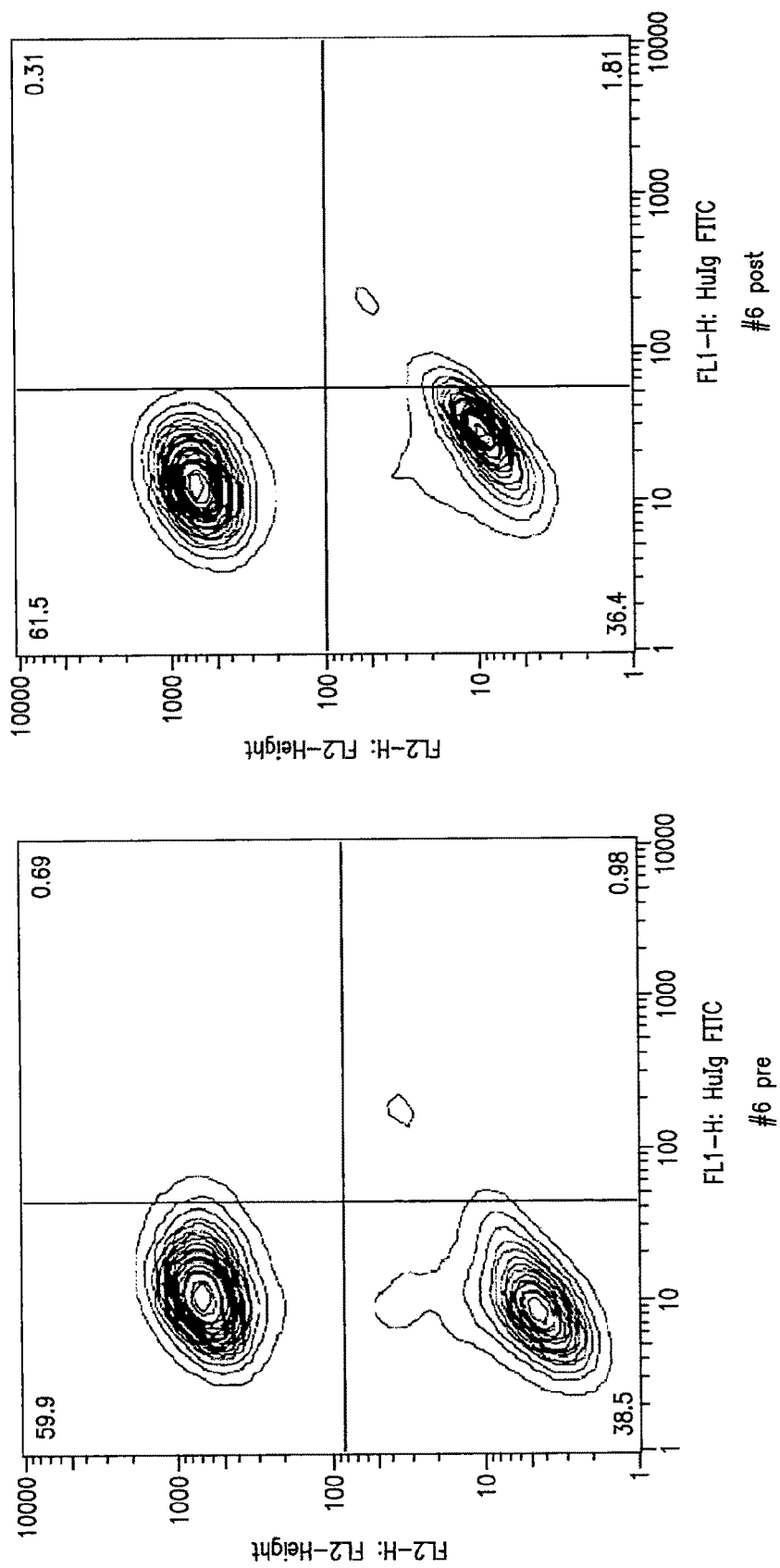
Figure 5B:
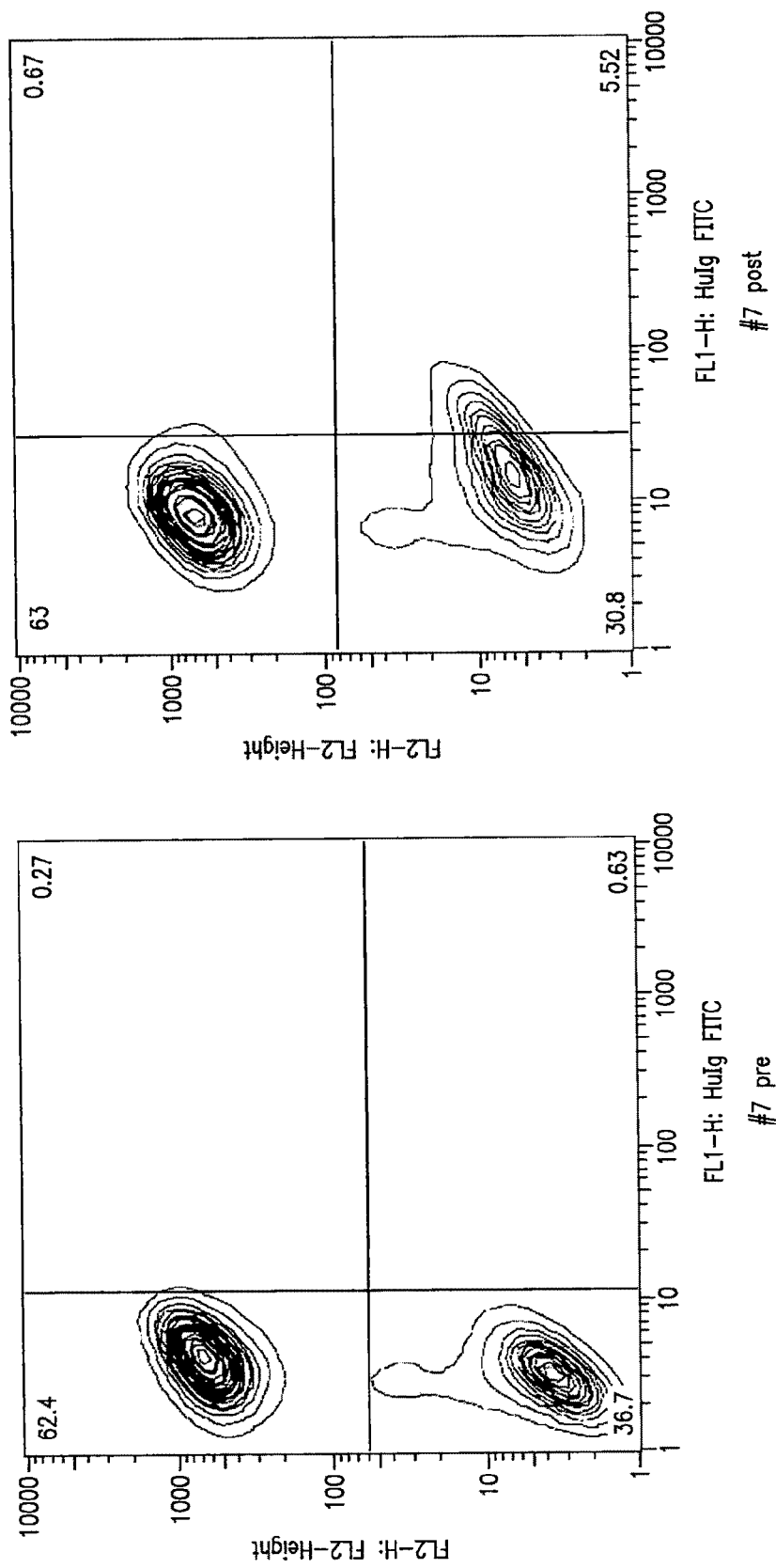

To confirm that the antibody against ROR1 is included in the antibodies against CLL cells induced by Ad-CD154 therapy, the sera from patients was reacted with CHO and CHO-ROR1 shown as FIG. 4C. Results showed that although serum from healthy donor or patient before treatment contained same reactivity against CHO and CHO-ROR1, sera from patient after Ad-CD154 therapy contained more Ig reacted with CHO-ROR1 than with CHO (FIGS. 5A and B).

Figure 6A:
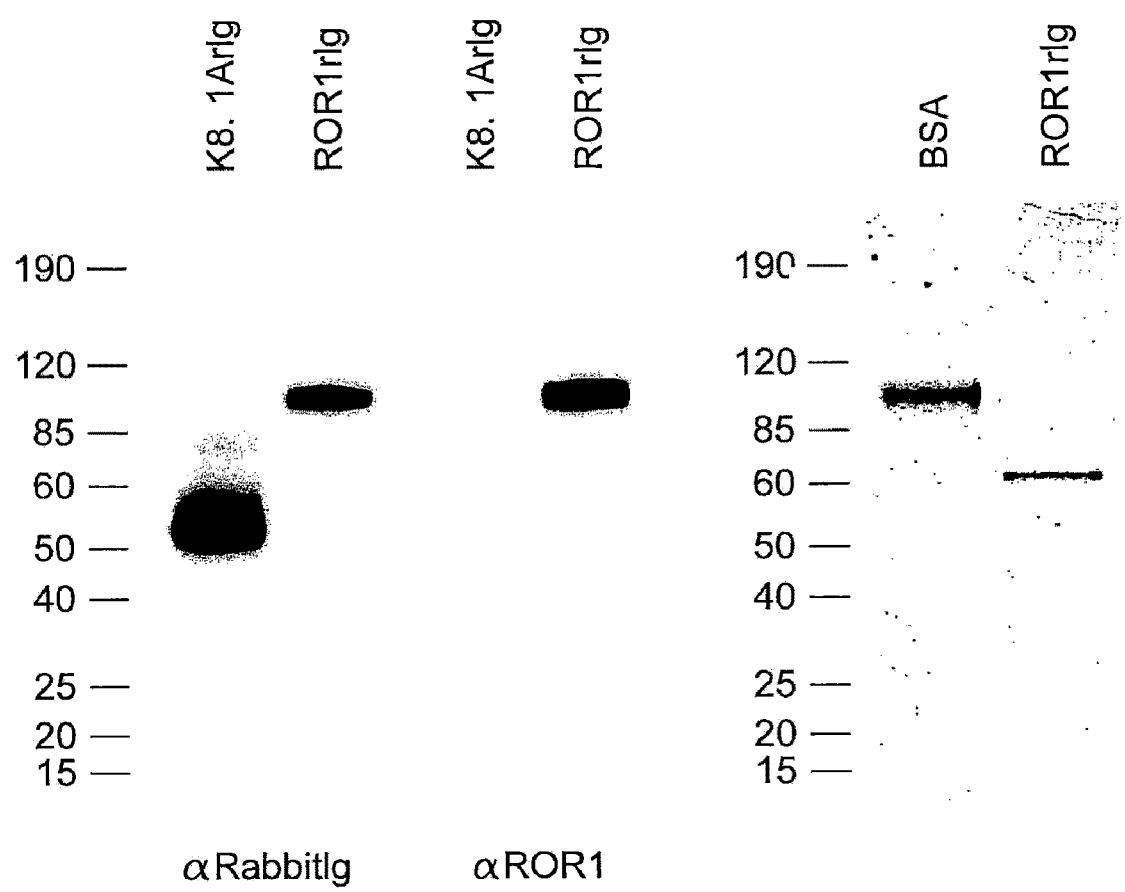
FIGS. 6A through 6C show production of anti-ROR1 antibody detected by ELISA.

A recombinant ROR1-rabbit Ig protein that had the extracellular domain of human ROR1 conjoined with the constant region of rabbit IgG was generated, allowing for its isolation via protein A column chromatography (FIG. 6A). Serial dilutions of sera obtained from patients before (dotted line) or after (solid line) treatment were applied to plates coated with the recombinant ROR1-rIg protein, which subsequently were developed with horse-raddish peroxidase (HRP) anti-human IgG. The pre-treatment sera from each patient or from each of 3 healthy adult donors failed to react with ROR1-rIg or rIg coated plates (FIG. 6B and data not shown). However, the sera of patients that reacted with allogeneic CLL cells (e.g. patients #5, #6, and #7) each reacted with plates coated with ROR1-rIg (FIG. 6B) even when saturating amounts of rabbit Ig were added to the sera prior to the assay. The post-treatment sera of patients #2 and #3 had low-level binding for ROR1-rIg by this ELISA at low serum dilutions (FIG. 3B). However, the post-treatment sera of patient #4 failed to react specifically with ROR1-rIg, even at the lowest serum dilution (e.g. 1/10).

Figure 6C:
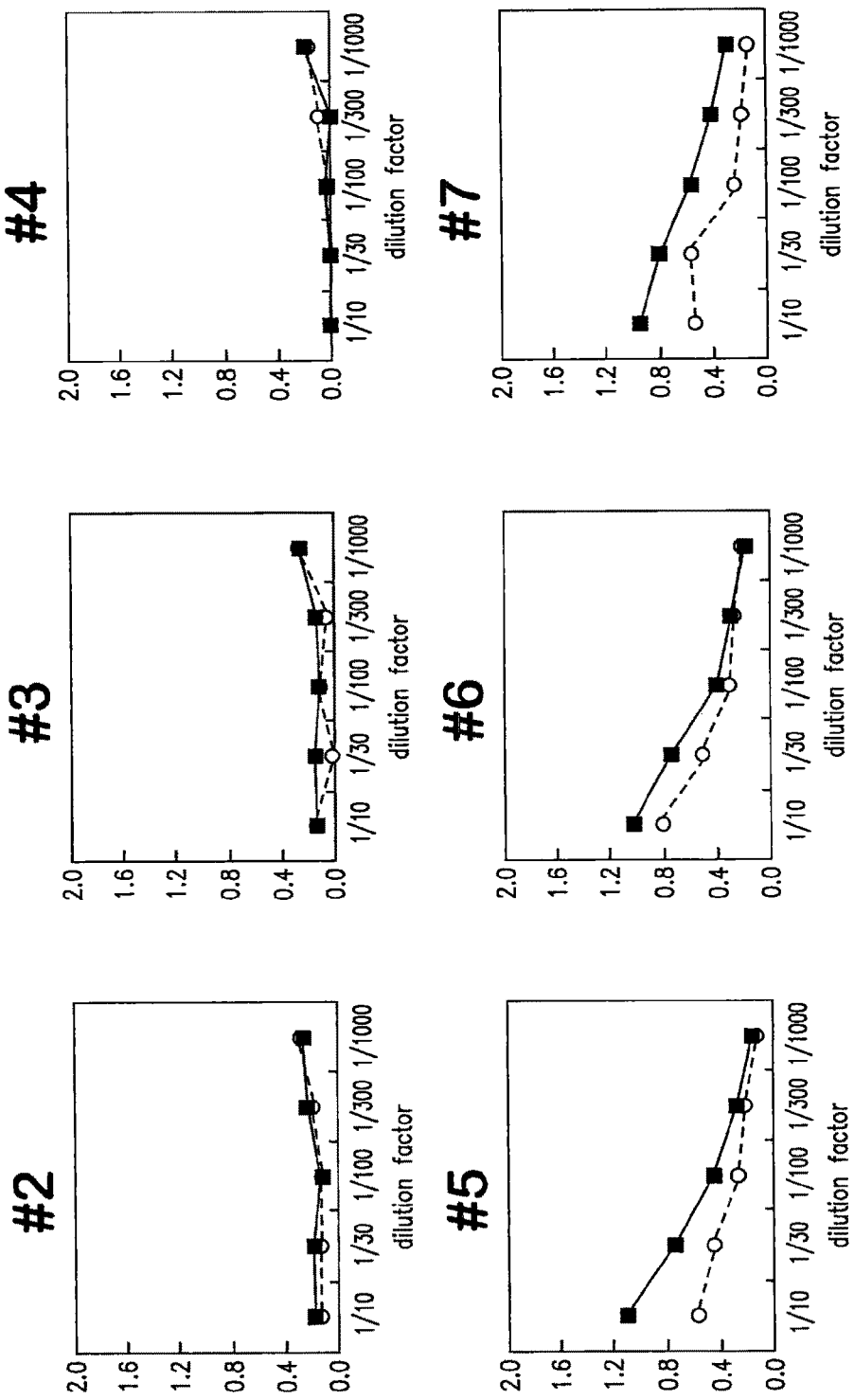

Further verification of the induction of anti-ROR1 antibody by Ad-CD154 therapy was established with an ELISA assay using the recombinant extracellular domain of ROR1 fused with rabbit IgG Fc (FIG. 6A). Results showed that anti-ROR1 antibody was clearly identified in 4 patients (#2, 5, 6, 7) after Ad-CD154 therapy. The remaining one patient (#3) also had a weak anti-ROR1 reaction although one patient (#4) did not get anti-ROR1 antibody by this therapy. This #4 patient was profound hypogammaglobulinemia and was totally unresponsive to this therapy with no decrease of white blood cell count (data not shown). Thus, all responsive patient to Ad-CD154 had induction of anti-ROR1 antibody after completion of therapy. In these patients, anti ROR1 antibody was not obvious before Ad-CD154 therapy. Although three patients (#5, 6, 7) had some reactivity also against rabbit IgG, this reactivity was also detected before therapy (FIG. 6C). Collectively ROR1 was expressed on CLL B cells restrictedly and could induce humoral immunity by means of immune-gene therapy.

Example 14

ROR1 Activation of Intracellular Machinery Associated with Development and Progression of CLL To demonstrate that ROR1 can activate intracellular machinery associated with development or progression of CLL, the influence of exogenous ROR1 expression on the reporter gene regulating various transcription factors in HEK293 cells was examined. Various Wnt family members were co-transfected, as ROR1 has a cystein-rich domain, which is shared between frizzled receptors and can bind with Wnt family members.

In prior studies, it was found that CLL cells expressed high-levels of Wnt3, Wnt5b, Wnt6, Wnt10a, Wnt14, and Wnt16, but lacked expression of Wnt5a. Because ROR1 is a receptor for Wnt5a, we examined the effect of Wnt5a on CLL cells in vitro. For this CHO cells were transfected with pWnt5a and selected stable transfectants that expressed high levels of human Wnt5a, which we designated as CHO-Wnt5a. CLL cells were cultured alone or together with CHO cells or CHO-Wnt5a cells and the viability of the CD19-positive CLL cells were examined over time.

Representative studies of three experiments using CLL cells from each of 4 different patients are presented in FIG. 18B. The viability of CLL cells co-cultured with CHO cells or CHO-Wnt5a cells was significantly greater than that of CLL cells cultured alone, particularly after 1 day in culture. However, in each case, the viability of CLL cells co-cultured with CHO-Wnt5a cells was significantly greater than that of CLL cells co-cultured with CHO cells, particularly at later time points. These studies revealed a previously unrecognized survival advantage for CLL cells when co-cultured with Wnt5a-expressing bystander cells.

The survival of CLL cells in vitro in the presence of anti-sera from the patients was evaluated. None of the pre- or post-treatment sera from either of the patients who developed anti-ROR1 antibodies enhanced or reduced the viability of CLL cells relative to that of CLL cell cultured in media with normal human serum or FBS, even at serum concentrations of 20% (FIG. 18B, culture conditions 1, 2, or 3, and data not shown). Because no direct effects on CLL cells of the anti-ROR1 antisera were observed, the question of whether the sera of a treated patient could effect the survival of CLL cells co-cultured with CHO cells or CHO-Wnt5a cells in vitro was examined. For this, the pre-treatment and post-treatment sera of one patient (#5) who developed IgG anti-ROR antibodies and who also experienced a durable partial response to Ad-CD154 gene therapy, as per NCI-working group criteria, were examined. CLL cells co-cultured with CHO-Wnt5a had significantly higher viability than CLL cells co-cultured with CHO cells or CLL cells cultured alone in media containing 20% pre-treatment serum (FIG. 18B, culture condition 5 relative to 4 or 2). However, the post-treatment serum from this patient could neutralize the capacity of CHO-Wnt5a to promote CLL-cell survival relative to that of CHO cells or media alone, even when the post-treatment serum previously had been absorbed on CHO cells (FIG. 18B, culture condition 7 relative to 6 or 3). On the other hand, in the presence of post-treatment serum that previously had been absorbed on CHO-ROR1 cells, the CHO-Wnt5a cells again provided a significant survival advantage to the CLL cells relative to that provided by CHO cells (FIG. 18B, culture condition 9 relative to 8 or 3).

Figure 7C:
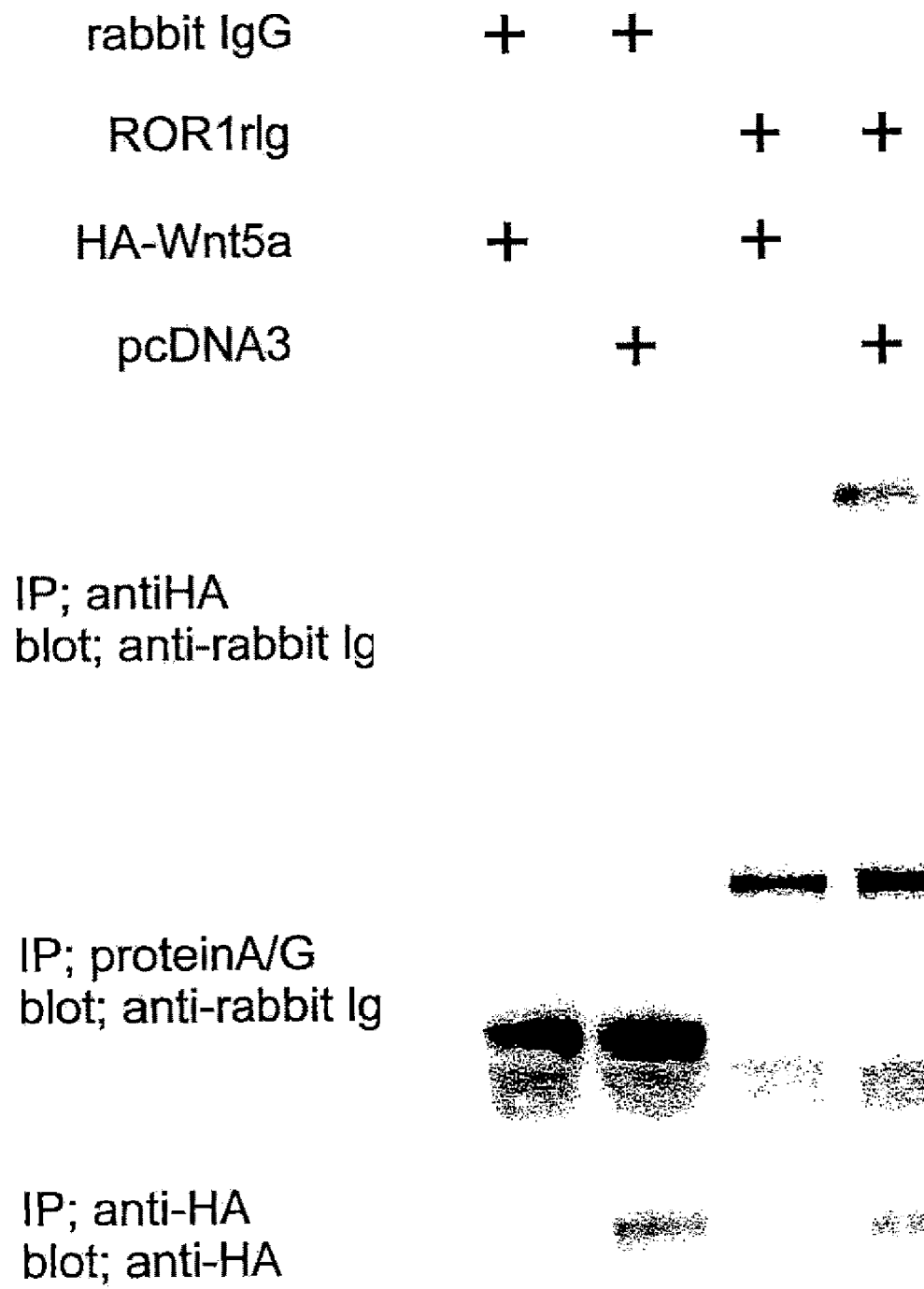

Results showed that the expression of ROR1 with any Wnt factor did not activate T-cell transcription factor (TCF) (FIG. 7A, data not shown), suggesting that ROR1 does not signal via the canonical Wnt-signaling pathway. ROR1 could not activate nuclear factors of activated T cells (NFAT), or AP-1 dependent gene expression (FIG. 7A). However, it was observed that co-expression of ROR1 in HEK293 cells with Wnt5a, but not with any other Wnt factor, induced activation of NF-κB (FIG. 7B). Induction of NF-κB was dose dependent on expression of ROR1 and Wnt5a, but independent of expression of LPR5/6 that ordinarily serve as co-receptors for the frizzled family of Wnt receptors (data not shown). Recombinant extracellular region of ROR1 could bind with Wnt5a in vitro (FIG. 7C). This data suggests non-canonical Wnt member, Wnt5a may be the ligand of ROR1 and induce the activation signaling in cells.

Example 15

Lymphoma Cell Isolation and Purification

Staining of CLL Cells from Patients #1, 2, or 3 with 4A5 mAb

As depicted in FIG. 8, the number of the CLL patient is indicated at the left-hand margin. Each panel depicts the staining of CLL with Alexa-647-conjugated 4A5 mAb (blue histogram) versus an Alexa-647-conjugated isotype control mAb (red histograms). In the first column is the staining of total peripheral blood mononuclear cells, in the middle column is the staining of the CD19+ (total B cells), and in the far right column is the staining of cells that express both CD19 and CD5 (CLL cells), indicated at the columns' bottoms.

Staining of Cells from Normal Donors #1, 2, or 3 with 4A5 mAb

Figure 9:
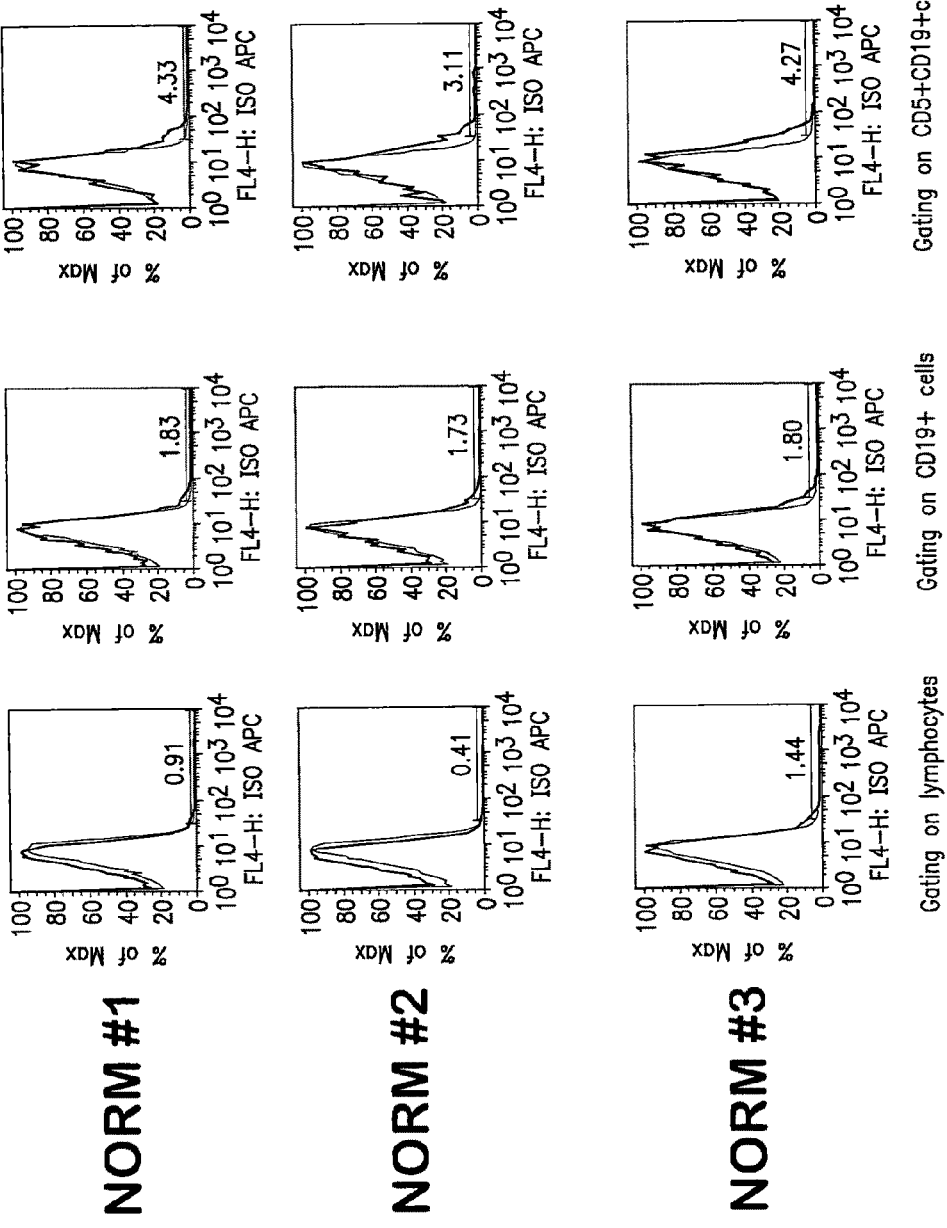
FIG. 9 is a series of histograms showing gated normal patients and CD19+ and CD19+CD5+ cells.

As depicted in FIG. 9, the number of the normal donor (NORM) is indicated at the left-hand margin. Each panel depicts the staining of cells with Alexa-647-conjugated 4A5 mAb (blue histogram) versus an Alexa-647-conjugated isotype control mAb (red histograms). In the first column is the staining of total peripheral blood mononuclear cells, in the middle column is the staining of the CD19+ (total B cells), and in the far right column is the staining of cells that express both CD19 and CD5, as indicated at the bottom of each column.

Staining of Cells from an Exceptional Normal Donors

Figure 10:
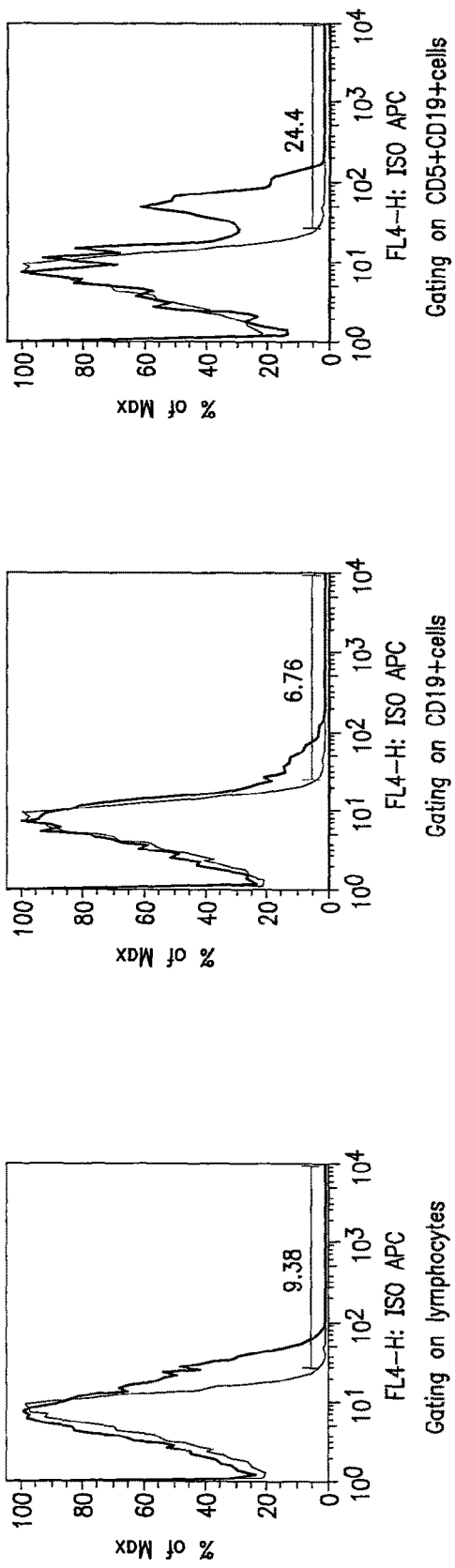
FIG. 10 is a series of histograms showing gated "exceptional" normal patients and CD19+ and CD19+CD5+ cells.

Recent studies indicate that close to 4% of adults over the age of 40 might have low numbers of cells similar to CLL cells in the peripheral blood. Moreover, over 11% of normal donors who have first degree relatives with CLL might have such cells in the peripheral blood. In FIG. 10, it is shown that anti-ROR1 mAb 4A5 can detect an occasional normal donor with ROR1 positive cells. Each panel depicts the staining of cells with Alexa-647-conjugated 4A5 mAb (blue histogram) versus an Alexa-647-conjugated isotype control mAb (red histograms). In the first column is the staining of total peripheral blood mononuclear cells, in the middle column is the staining of the CD19+ (total B cells), and in the far right column is the staining of cells that express both CD19 and CD5, as indicated at the bottom of each column. As can be noted from this figure, the ROR1 positive cells co-express CD5 and CD19, a phenotype common with CLL cells.

Staining of CLL Cells in the Marrow

In FIG. 11, numbers corresponding to a CLL patient are provided at the left-hand margin. Each panel depicts the staining of cells with Alexa-647-conjugated 4A5 mAb (blue histogram) versus an Alexa-647-conjugated isotype control mAb (red histograms). In the first column is the staining of total marrow mononuclear cells, in the middle column is the staining of the CD19+ (total B cells), and in the far right column is the staining of cells that express both CD19 and CD5 (CLL cells), as indicated at the bottom of each column.

Staining of CLL Cells in the Marrow

Figure 12:
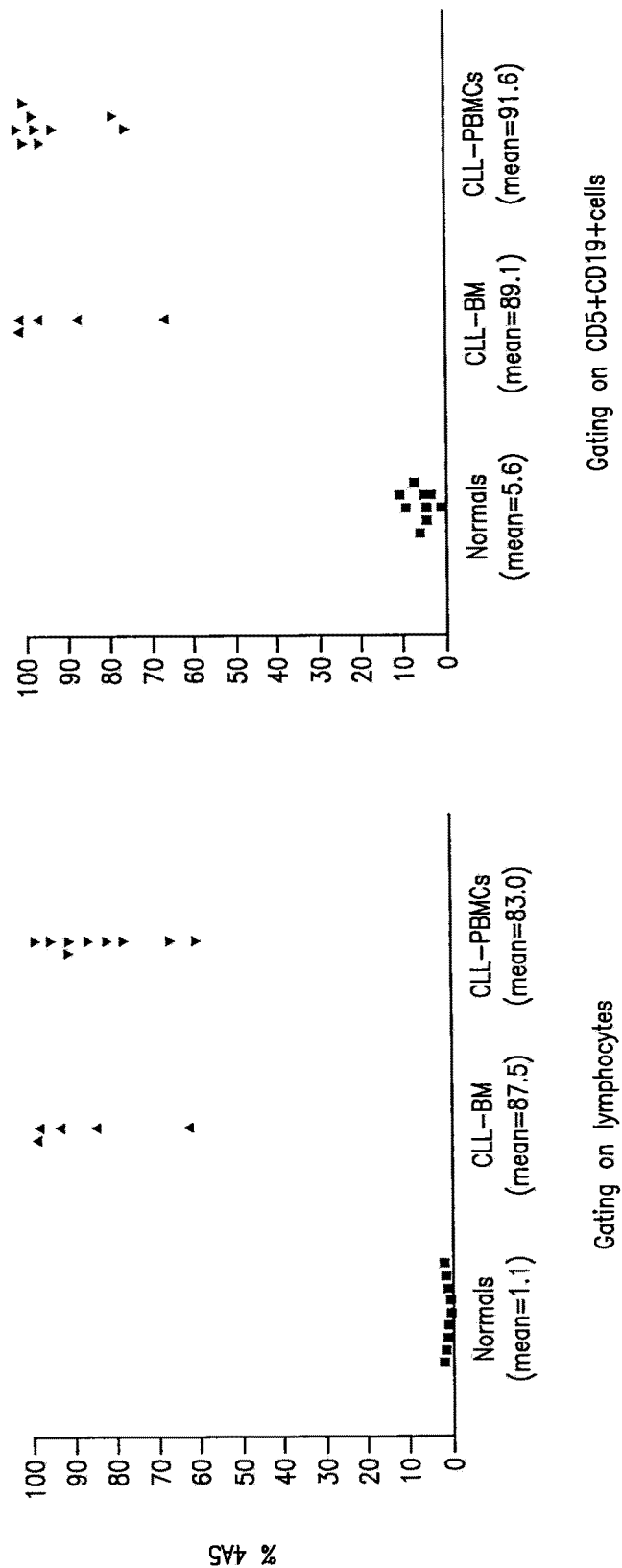
FIG. 12 depicts the expression of 4A5 versus normals versus CLLs and the gating effect.

The proportion of cells that express ROR1, as detected by the mAb 4A5, are indicated in FIG. 12. Each dot represents the proportion of cells from a single donor. The percent of cells scoring positive is indicated by the y-axis. The left hand panel provides the percent lymphocytes (as per light scatter) that stain with 4A5 mAb. The right panel provides the percent of CD5+CD19+ B cells that stain with 4A5. The left panel provides the percent of lymphocytes that stain with 4A5 in samples obtained from the blood normal donors (far left), the marrow of patients with CLL (middle), or blood of patients with CLL (far right).

Example 16

Magnetic Bead Detection and Isolation of Lymphoma Cells

Lymphoma cells can be isolated and purified using the following procedure:
1. Stain CLL cells with PKH67
2. Titrate CLL cells in normal PBMCs (10% to 0.1%)
3. Stain cells with:
    a. Iso-Alexa647 CD5, CD19
    b. 4A5-Alexa647, CD5, CD19
4. Incubate for 20 min on ice followed by a wash 2× with PBS-0.5% BSA
5. Add magnetic beads (Miltenyi) to cells; Incubate 15 min on ice; Wash 1× with PBS-0.5% BSA)
6. Add column to magnet; Wash 1× with 3 ml PBS-0.5% BSA
7. Add this mixture to pre washed column; Wash unbound cells 3× with 3 ml PBS-0.5% BSA; (unbound fraction=4A5 NEG)
8. Remove column from magnet; Add 5 ml PBS-0.5% BSA; (bound fraction=4A5 POS)

Detection of CLL Cells Admixed with Normal Lymphocytes

Figure 13:
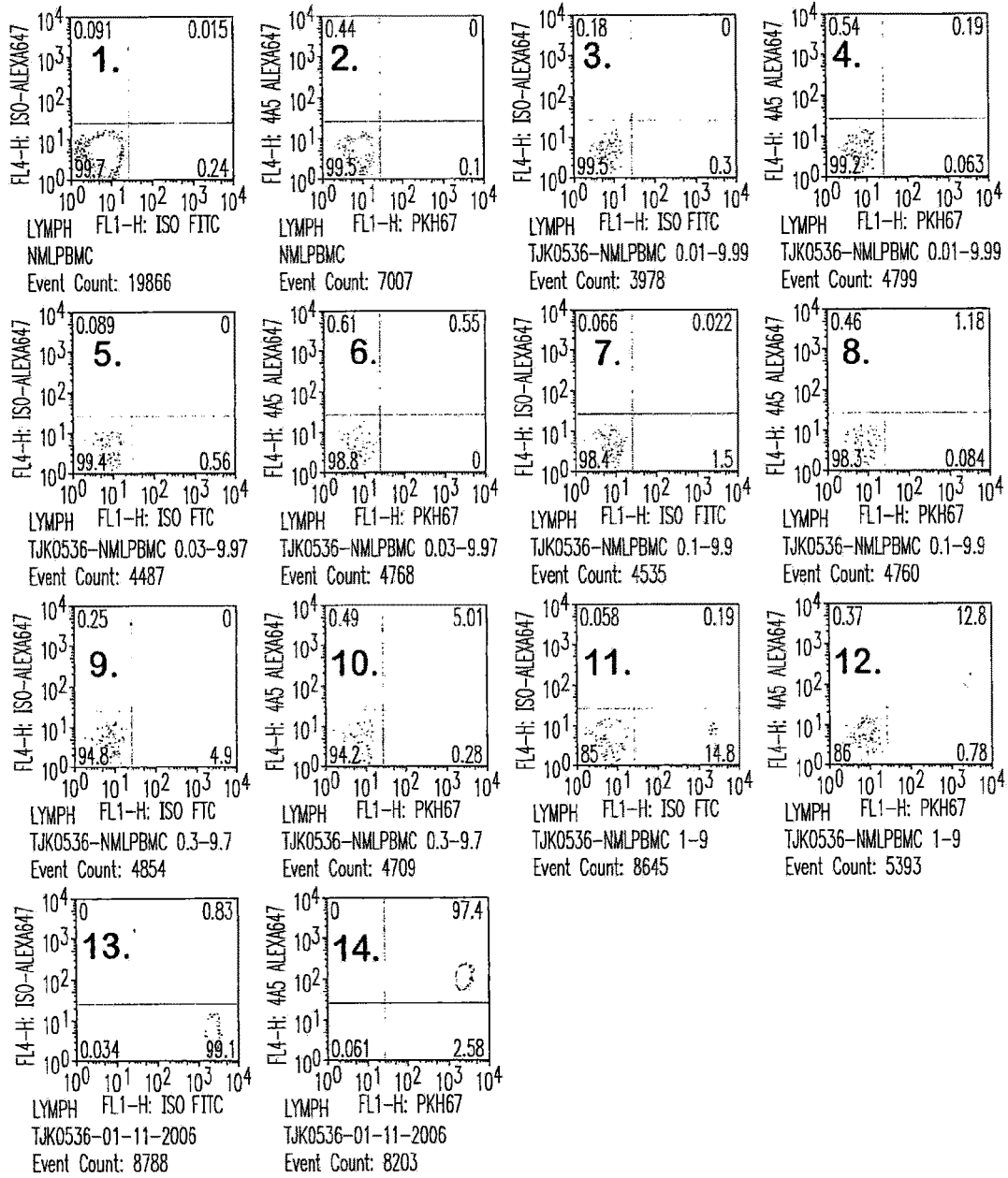
FIG. 13 is a series of histograms showing different levels of 4A5 expression on titrated CLL cells.

4A5+ CLL cells admixed with the lymphocytes from normal donors are shown in FIG. 13. CLL cells were first stained with PKH67, which labeled them bright green (as observed on the x axis), allowing for their detection after being admixed with normal lymphocytes. The stained CLL cells were mixed with the lymphocytes of a normal donor and then the mixture was stained with an Alexa-647-conjugated isotype control mAb (ISO) Alexa-647-conjugated 4A5, allowing for detection of the red fluorescence seen on the y-axis.

Each panel represents a different mixture of cells stained with either the isotype control mAb or 4A5, as indicated in the key, which refers to the number in each panel of the figure. Those samples stained with the isotype control mAb are indicated by the term "Iso", those samples stained with 4A5 are indicated. The percent preceding the CLL is the percent at which the CLL cells are represented in the mixture. As seen from this figure, the 4A5 mAb does not stain normal lymphocytes, allowing for detection of minute proportions of CLL cells that are labeled green.

Isolation of CLL Cells Admixed with Normal Lymphocytes

Figure 14:
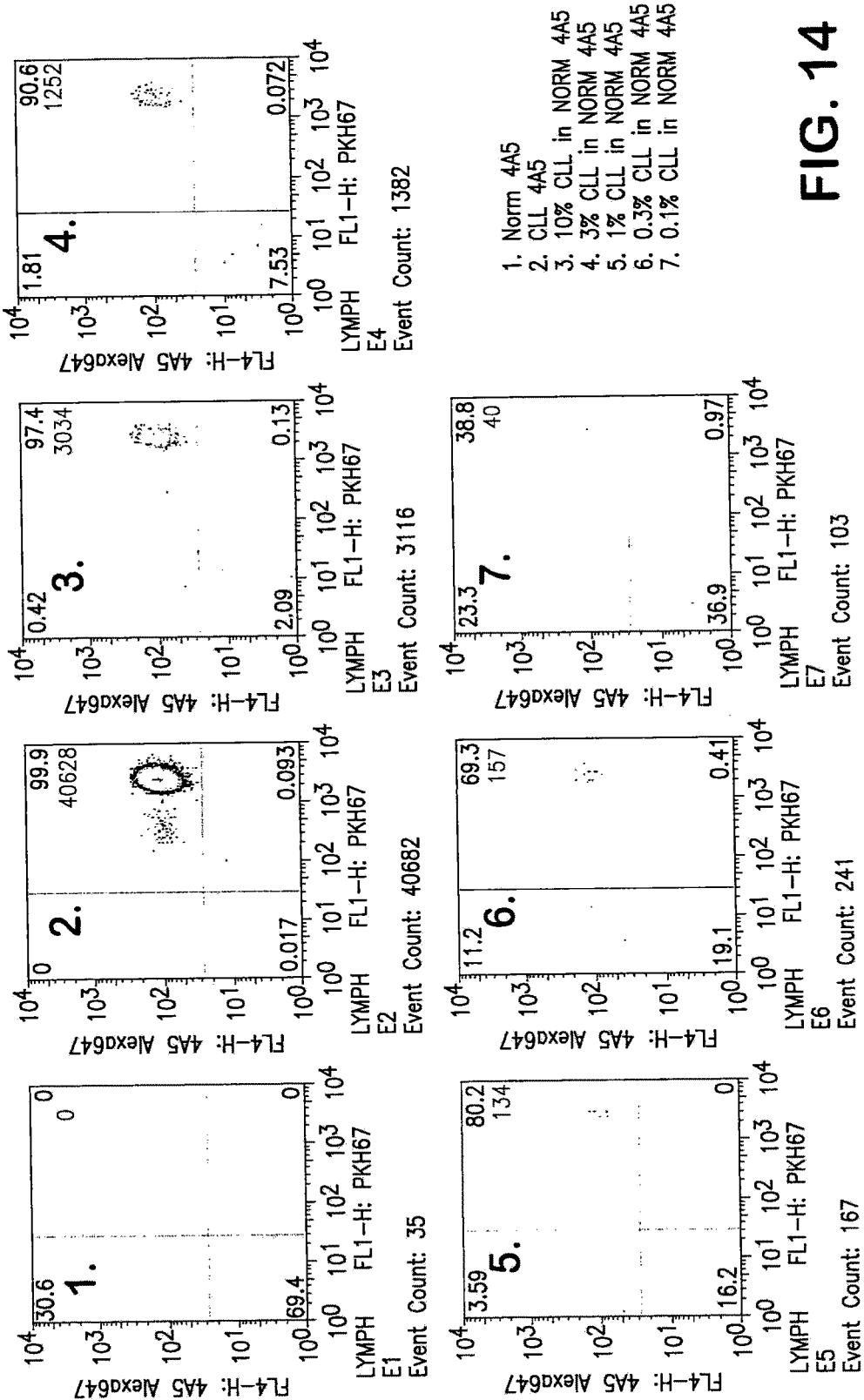
FIG. 14 is a series of histograms showing different levels of 4A5 expression and that such cells can be purified using magnetic beads and methods provided herein.

Isolated 4A5+ CLL cells admixed with the lymphocytes from normal donors are indicated in FIG. 14. CLL cells were stained, mixed with normal lymphocytes at various ratios, and then stained with fluorochrome-conjugated 4A5 mAb, as in Slide #6. Each panel represents analyses of cells isolated from different mixtures of CLL cells with normal lymphocytes, as indicated in the key, which refers to the number in each panel of the figure. The percent preceding the CLL is the percent at which the CLL cells are represented in the mixture.

As seen from this figure, the 4A5 mAb does not stain normal lymphocytes, allowing for detection of minute proportions of CLL cells that are labeled green. As can be seen in these panels, this method can isolate fairly pure populations of CLL cells from mixtures of CLL cells with normal lymphocytes in which the CLL cells constitute only a small fraction of the total cells.

Example 17

Detection of ROR1 Antibody in Cancer but not Normal Cells

To evaluate ROR1 surface expression in the human cell lines listed in the Table below (Table 1), CHO cells were used as a negative control and CHO-ROR1 cells as a positive control for flow cytometry. The ROR1 antibody was the 4A5 mAb. The control mAb was a conjugated isotype 1gG2b mAb.

The following cell lines stained brightly with the 4A5 mAb, confirming ROR1 expression: EW536, CLL, 786-0, HCT116, HT29, SW620, MDA-MB-231, MDA-MB-431, and MDA-MB-468. CHO, MOLT-4, SW948, MCF-7, and SKBR3 were negative for ROR1 expression, indicating preferential ROR1 expression in this population among adenocarcinoma and lymphoma.

In immunoblot studies of the same adult cancer tissues (using a ROR1 antibody raised against ROR1 peptide), the same cancer tissues reacted to indicate ROR1 expression. Using the A5A mAb, immunoprecipitation studies confirmed that ROR1 was not found on normal tonsil cells of CHO, but is strongly expressed in CLL, B cell lymphoma, and breast adenocarcinomas, less so in colon adenocarcinoma (data not shown).

TABLE 1

Descriptions Of The Various Cell Lines Used In Example 17

| Name | Source of Cells |
| --- | --- |
| CHO | Chinese hamster ovary cells |
| CHO-ROR1 | CHO cells transfected to express human ROR1 |
| EW36 | Endemic African Burkitt's lymphoma (a B cell lymphoma) |
| MOLT4 | Human T cell lymphoma |
| CLL | Human chronic lymphocytic leukemia |
| 786-0 | Human renal cell carcinoma cell line |
| HCT116 | Human colon adenocarcinoma cell line |
| HT-29 | Human colorectal adenocarcinoma cell line |
| SW620 | Human colon adenocarcinoma cell line |
| SW948 | Human colon cancer cell line |
| MCF-7 | Human, Caucasian, breast, adenocarcinoma |
| MDA-MB-231 | Highly aggressive human, Caucasian, breast, adenocarcinoma |
| MDA-MB-431 | Highly aggressive human, Caucasian, breast, adenocarcinoma |
| MDA-MB-468 | Highly aggressive human, Caucasian, breast, adenocarcinoma |
| SKBR3 | Human mammary carcinoma |

Example 18

ROR1 DNA Vaccine Constructs

Vectors were constructed to encode the chimeric ROR1 protein with ubiquitin located at the amino terminus separated from ROR1 by an intervening codon for Met, and a separate vector with a codon for the destabilizing amino acid Arg and an in-frame insert of a segment of lacI. This segment contains a lysine residue spaced optimally from the N-terminus. To generate the constructs, ROR1 was PCR amplified from the pCMV6-XL-ROR1 vector (Origene) using primers that encoded for NotI and XbaI. The PCR product was gel-purified, cut with those restriction enzymes and ligated into a pcDNA3 subclone that contained the chimeric Ub-M-(lacI) or Ub-R-(lacI). The final construct contains ROR1 3' of these sequences: Ub-M-ROR1 and Ub-R-ROR1.

Confirmation of ROR1 Protein Expression by Cell-Free Assay

The constructs were evaluated for their capacity to direct synthesis of the ROR1 protein. For this in vitro transcription and translation was performed using the TNT Quick coupled Transcription/Translation System™ from Promega in presence of biotinylated lysine-specific tRNA. A luciferase plasmid served as positive control for the reaction. Both constructs allowed for the expression of one predominant protein at the size of ROR1.

To demonstrate ROR1 protein expression in mammalian cells, P815 cells were transfected with Ub-M-ROR1 or Ub-R-ROR1 using the Amaxa transfection system according to manufacturer's instructions using program L13. The generation of such cells is described below.

Generation of P815 Cells Expressing ROR1

To examine the magnitude of the immune response generated by the Ub-M-ROR1 and Ub-R-ROR1 DNA vaccine, CTL activity of splenocytes harvested from immunized mice will be assessed against the H-2d mastocytoma, P815, and P815 cells transfected to express human ROR1. To generate P815 cells that stably expressed ROR1, P815 cells were transfected with pcDNA3-ROR1, generated using the Amaxa transfection system. To select ROR1 expressing cells, the cells were grown in G418 (400 µg/ml). Subsequently the cells were sub-cloned by limited dilation and analyzed for ROR1 expression by flow cytometry. A stable P185 clone was generated that expresses ROR1 (FIG. 17; P815-ROR1). This cell line will serve as target for CTL assays.

To generate stable transfectants, the cells were subsequently cultured under selection pressure in the presence of 400 µg/ml G418. G418-resistant cells were cloned by limiting dilution. To evaluate the relative intracellular stability of the transgene products in the transfected P815 cells, cells were cultured in the presence of a 26S proteasome inhibitor. P815 cells, and P815 cells stably transfected with the Ub-M-ROR1 or Ub-R—ROR1 constructs were incubated in 100 µM of the proteasome inhibitor LLnL (N-acetyl-L-leucinyl-L-leucinal-L-norleucinal) for 18 h. Lysates were prepared from the transfected cells and evaluated by Immunoblot for ROR1 expression.

As expected, in the absence of LLnL, only P815 cells transfected with the Ub-M-ROR1, but not with Ub-R-ROR1 expressed detectable ROR1 protein. Non-transfected P815 cells did not express ROR1. When both transfectants were cultured in the presence of LLnL a strong increase in ROR1 expression was observed. These results show that ROR1 expressed from the Ub-M-ROR1 and more so from the Ub-R-ROR1 constructs was degraded in the proteasome.

These constructs can be reasonably expected to induce antibody responses or anti-ROR1 CTL responses. To this end, cell based assays are useful to confirm the activity of candidate ROR1 vaccines, to compare and contrast activity among candidates and with ROR1 constructs that are not targeted for degradation. CTL activity is measurable using ROR1 expressing target cells and target cells without ROR1 as controls; e.g., in the P815 cells described.

Example 19

CLL Cell Culture Assays

CHO cells or CHO-Wnt5a cells were cultured in DMEM supplemented with 10% FBS. These cells were plated into separate wells of 24-well culture plates in 500 pl media at $5 \times 10^5$ cells/well.

Primary CLL cells from different patients that were viably frozen in 10% DMSO/50% FBS for storage in liquid nitrogen were rapidly thawed, suspended in cold RPMl media (4° C.), washed thrice, and then suspended in RPMI media at $1 \times 10^7$ cells/ml. The viability of each CLL cell population exceeded 85%. CLL cells at $5 \times 10^6$ cells/well were seeded onto wells containing media alone or CHO cells or CHO-Wnt5a cells. The viability of the CD19+ CLL cells in each of quadruplicate wells for each condition and time point was examined by flow cytometry after staining the cells with PI and $DiOC_6$.

Patient sera collected before (pre) or two weeks after (post) treatment with autologous Ad-CD154-transduced CLL cells were examined for their capacity to alter the viability of primary CLL cells cultured alone or together with CHO cells or CHO-Wnt5a cells. For studies using absorbed serum samples, 20% human serum in RPMI was used to suspend cell pellets of CHO cells or CHO-ROR1 cells to a final cell concentration of $2 \times 10^8$ ml. The samples were incubated for 30 minutes at 4° C. and then spun at 200×g for 4 minutes. The supernatant from each was removed and used as culture media. For this, $2.5 \times 10^6$ CLL cells in 250 μl of media were added to each well of a 48-well culture plate that contained 250 μl of culture media alone or 250 μl of culture media with $2.5 \times 10^5$ CHO cells or CHO-Wnt5a cells. Quadruplicate wells for each condition were harvested after 48 hours and the viability of the cultured CD19+ CLL cells measured by flow cytometry after staining the cells with PI and $DiOC_6$.

Example 20

Treatment of Cancer by Regulation of ROR1 and Detection of Minimal Residual Disease of Cancer Cells after Therapy The role of ROR1 expression in cancer cells was determined and depletion of ROR1 was determined to reduce tumor growth in vivo.

The neoplastic cells in chronic lymphocytic leukemia (CLL) and acute lymphocytic leukemia (ALL) cells express ROR1. Stimulation of ROR1 in response to Wnt5a activates NF-κB signaling and enhances leukemia-cell survival. Using microarray analysis, it was found that ROR1 protein was expressed by a large variety of human tumor tissues, but not by normal adult tissues. Established human cancer cell lines from a variety of different human cancers also expressed high levels of ROR1, as determined by cytometry and immunoblot analysis. Expression of ROR1 activated NF-κB signaling with Wnt5a in human breast cancer cell lines (e.g. MDA-MB-231). Conversely, RNA-interference-mediated silencing of ROR1 repressed Wnt5a-induced expression of NF-κB-luciferase. Transient transfection of established human tumor cells with a shRNA that interference with ROR1 expression (ROR1-shRNA) resulted in apoptosis. Repression of ROR1 protein expression via stable transfection of ROR1-shRNA inhibited tumor cell growth in vitro and in vivo in using a xenograft mouse model.

As discussed herein, monoclonal antibodies (mAbs) specific for ROR1 were developed for use in flow cytometry, immunoblot analysis, immunohistochemistry detection, and immune precipitation of ROR1. Due to the restricted expression of ROR1, the anti-ROR1 mAb could be used to detect minimal residual disease (MRD) of cancer cells after therapy.

One anti-ROR1 mAb, 4A5, was used to stain blood or marrow cells of patients with CLL. The mAb 4A5 reacted with the CLL cells of all patients examined, and also with some cells that had an immunophenotype of B lymphocyte precursors (BLP) (CD10+, CD19+, CD20-variable, dim CD45+, surface immunoglobulin-negative). 4A5 showed no reactivity with other blood or marrow cells.

The 4A5 mAb can be used to detect CLL cells in blood or marrow of patients after therapy, providing the means with which to assess for MRD following treatment. For this purpose, a four-color combination of mAbs using CD10-FITC, CD19-PE, CD5-PerCP-Cy5.5, and 4A5-Alexa-647 was used. MRD detection limits were established through reconstitution studies in which serial dilutions of CLL cells were made into normal blood or marrow samples. MRD was measured by whole blood lysis and acquisition of 100,000 events using a FACSCalibur™ and a gating strategy designed to exclude CD5-negative, CD10-positive, and 4A5-negative B lymphocytes (CD19+). CLL cells stained with fluorochrome-conjugated (Alexa-647) 4A5, which resulted in the cells having a mean fluorescence intensity (MFI) of 31 (N=100) and a MFI ratio (MFIR) of fluorescence relative to that of CLL cells stained with an isotype control mAb of more than 10:1. On average, 94% of the CLL cells in each sample had higher fluorescence intensity when stained with 4A5-Alexa-647 than when stained with an isotype-control mAb (range 88-98%). Marrow samples (N=9) from adults with diagnoses other than CLL and that had 1-10% BLP had CD5-negative, CD10+, CD19+ cells that reacted with the 4A5-Alexa 647. These cells in such samples had a MFI of 19 and a MFIR relative to that of isotype-control-stained BLP of 6.3. On average, 48% of such cells in each sample had higher fluorescence intensity when stained with 4A5-Alexa-647 than when stained with an isotype-control mAb (range 18-79%). Four color flow cytometric analysis with CD10, CD19, CD5, and 4A5 detected CLL cells present at less than 0.1% in reconstituted blood or marrow samples, including marrow with 3-5% BLP. Background was between 0.01% and 0.1% with whole blood (marrow) lysis when a total of 100,000 flow-cytometric events were acquired. These data indicate that anti-ROR1 mAbs can be used with mAbs specific for CD10, CD19, and CD5 for sensitive detection of MRD in CLL.

Materials and Methods

The following cell lines and animals were used Cell lines were bought from ATCC (American Type Culture Collection, Manassas, Va., USA). All cell lines were routinely maintained in DMEM (Gibco) supplemented with 10% FBS and antibiotics at 37° C. in a humidified atmosphere containing 5% carbon dioxide ($CO_2$) except L cells. L cells and L cells transduced to express Wnt5a, L-Wnt5a cells, were maintained in DMEM supplemented with 5% FBS. At 72 hours after infection with lentivirus containing Ct-shRNA and ROR1-shRNA, stable transfectants were selected with 1 μg/ml of puromycin (Sigma) for 14 days. ROR1 knockdown cells were sorted by flow cytometry after staining with 4A5 for analysis of cell proliferation in vitro and in vivo tumorigenicity. Rag$^{-/-}$γ$^{-/-}$ mice, 4 to 6 weeks' old, were housed in laminar-flow cabinets under specific pathogen-free conditions, with food and water. All experiments in mice were conducted in accordance with the guidelines of National Institutes of Health (NIH; Bethesda, Md., USA) for the care and use of laboratory animals.

Immunohistochemical staining was performed as follows. Tissue microarray (TMA) slides and frozen tissues were purchased from NDRI. Immunohistochemical staining (IHC) using the streptavidin-biotin method was performed to detect ROR1. In brief, sections (NDRI) were deparaffinized and treated for 30 min with 0.1 M citrate buffer (pH 6.0). Endogenous peroxidase in the section was quenched by incubation in 3% hydrogen peroxide for 30 min at room temperature. After washing with phosphate buffered saline (PBS) and incubation with goat serum for 1 h, the sections were incubated with primary antibodies 4A5 at 4° C. overnight. Biotinylated second antibody and peroxidase-conjugated streptavidin from the DAKO Universal LSAB2™ kit (DAKO, Denmark) were applied for 30 min each. Finally, sections were incubated in the Substrate Chromogen (AEC) for 6 min, followed by hematoxylin counterstaining and mounting. Negative controls were obtained by replacing the primary antibody with IgG2b.

Flow cytometry was performed as follows. Cells were stained with 4A5 antibody conjugated with Alexa Fluor 647 for 20 min at 4° C. in staining media (PBS/3% FBS/1 mM Hepes). The cells were washed twice in staining media. Samples were analyzed by using a FACSCalibur™ (Becton-Dickinson, San Jose, Calif.) with FlowJo™ software.

Apoptosis assays were performed as follows. Cells were harvested and then stained with 5 µg/ml annexin V-FITC in the dark for 15 min at room temperature. Samples were analyzed by flow cytometry with a FACScan™ instrument (Becton-Dickinson).

Immunoprecipitate and immunoblot analysis was performed as follows. The cells were lysed with 1 ml of lysis buffer (20 mM Tris-HCl, pH 7.4, 2 mM EDTA, 0.5% Nonidet P-40) plus protease inhibitors (Sigma) for 30 min at 4° C. After 12,000×g centrifugation for 15 min, protein concentrations (BCA protein assay, Pierce) were determined. Using mAb 4A5, ROR1 was immunoprecipitated from equal quantities of lysate protein for 3 h at 4° C. The precipitants were subsequently washed three times and the immune complexes eluted with sample buffer containing 1% SDS for 5 min at 95° C. and analyzed by SDS-PAGE. Immunoblot analysis was performed using rabbit antibodies to ROR1-peptides (Cell Signaling Technology) and secondary anti-rabbit antibodies conjugated with horseradish peroxidase (Amersham Biosciences). Proteins were visualized by chemiluminescence (Pierce).

RT-PCR was performed as follows. Total RNA was prepared from various cells using RNeasy™ Mini kit (Qiagen). One microgram of RNA was reverse transcribed at 42° C. for 45 min in a 20-µl reaction mixture using the Reverse Transcription System™ (Promega). Expression levels of Wnt5a were detected by semi-quantitative PCR with the following primers: 5'-ATTAAGCCCAGGAGTTGC-3' (SEQ ID NO: 13) (forward) and 5'-GAAAGTCCTGCCAGTTGG-3' (SEQ ID NO: 14) (reverse). The primers for the glyceraldehyde 3'-phosphate dehydrogenase (GAPDH) gene were: 5'-GAAGGTGAAGGTCGGAGTC-3' (SEQ ID NO: 15) (forward) and 5'-GAAGATGGTGATGGGATTTC-3' (SEQ ID NO: 16) (reverse).

Luciferase assays were performed as follows. After 24 hours post-transfection, cells were treated with L or L-wnt5a conditioned medium for 20 hours and then harvested for determination of luciferase activity with a luminometer (MicroBeta TriLux™, Gaithersburg, Md.). The luciferase values were normalized for variations in transfection efficiency by using β-galactosidase as an internal control, expressed as relative luciferase activity, and compared with the designated control cultures. All assays were performed in triplicate.

RNA Interference was performed as follows. Virapower lentiviral expression system (Invitrogen) was used for the expression of shRNA according to the manufacturer's instructions. The target sequence of human ROR1 was 5'-ATCCGGATTGGAATTCCCATG-3' (SEQ ID NO: 17). A nonspecific shRNA expression vector pLk0.1 containing the sequence 5'-AGCGGACTAAGTCCATTGC-3' (SEQ ID NO: 18), was constructed as a negative control. Oligonucleotides were synthesized (Integrated DNA Technologies) and inserted into the vector.

Cell proliferation assays were performed as follows. Cell proliferation was analyzed using Cell-Counting Kit™ (CCK)-8 (Dojindo, Kumamoto, Japan). Control and ROR1 knock down cells were harvested and plated in 96-well plates at $1 \times 10^3$ cells/well and maintained at 37° C. in a humidified incubator. 10 µl of CCK-8 solution was added to each well at different time points and cells were incubated for 3 hours. The absorbance at 450 nm was measured to calculate the numbers of vital cells in each well. The morphology of cells was observed by phase-contrast inverted microscope.

Tumorigenicity assays were performed as follows. Subconfluent Ct-shRNA and ROR1-shRNA MDA-MB-231 stable cells infected with or without lentivirus containing luciferase were trypsinized, suspended in serum-free medium ($5 \times 10^6$ cells/ml), and mixed with an equal volume of cold Matrigel™. Cell suspension ($10^6$ cells in 400 ul) was injected into female Rag$^{-/-}$γ$^{-/-}$ immunodeficient mice. Measuring the length and width of tumors every 3 to 4 days allowed us to monitor tumor growth over time. Tumor volumes were estimated using the formula: (length×width)$^2$×0.4. Results are expressed as the mean of tumor volumes for each experimental group. Luciferase signaling was detected using a sensitive in vivo imaging system (IVIS 200 series, Xenogen). Mice were anesthetized with isoflurane and injected with luciferin (150 mg/kg ip injection) approximately 10 min before imaging. The images were analyzed by using total photon flux emission (photons/s) in an ROI covering the entire tumor with Living image software.

Results

Many different human cancers and cancer cell lines express ROR1. As discussed herein ROR1 protein was expressed in leukemia cells including CLL and ALL, but not normal blood cells. Fukuda et al. (2008) Proc Natl Acad Sci USA., 105:3047-3052; Shabani et al. (2007) Tumour Biol., 28:318-326; Baskar et al. (2008) Clin Cancer Res. 14:396-404.

Figure 21:
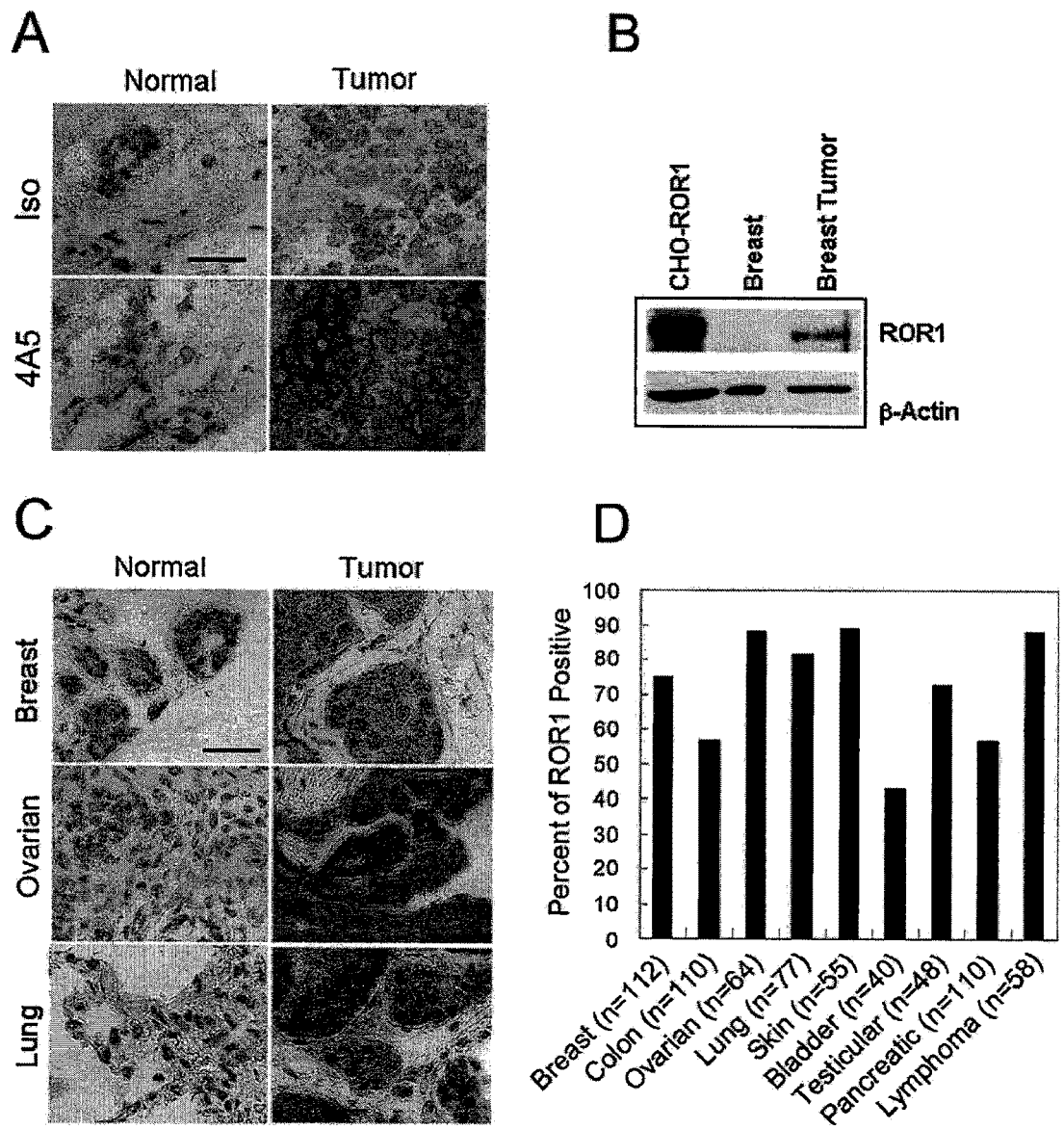
FIG. 21 illustrates ROR1 is highly expressed in various tumors.
Figure 22:
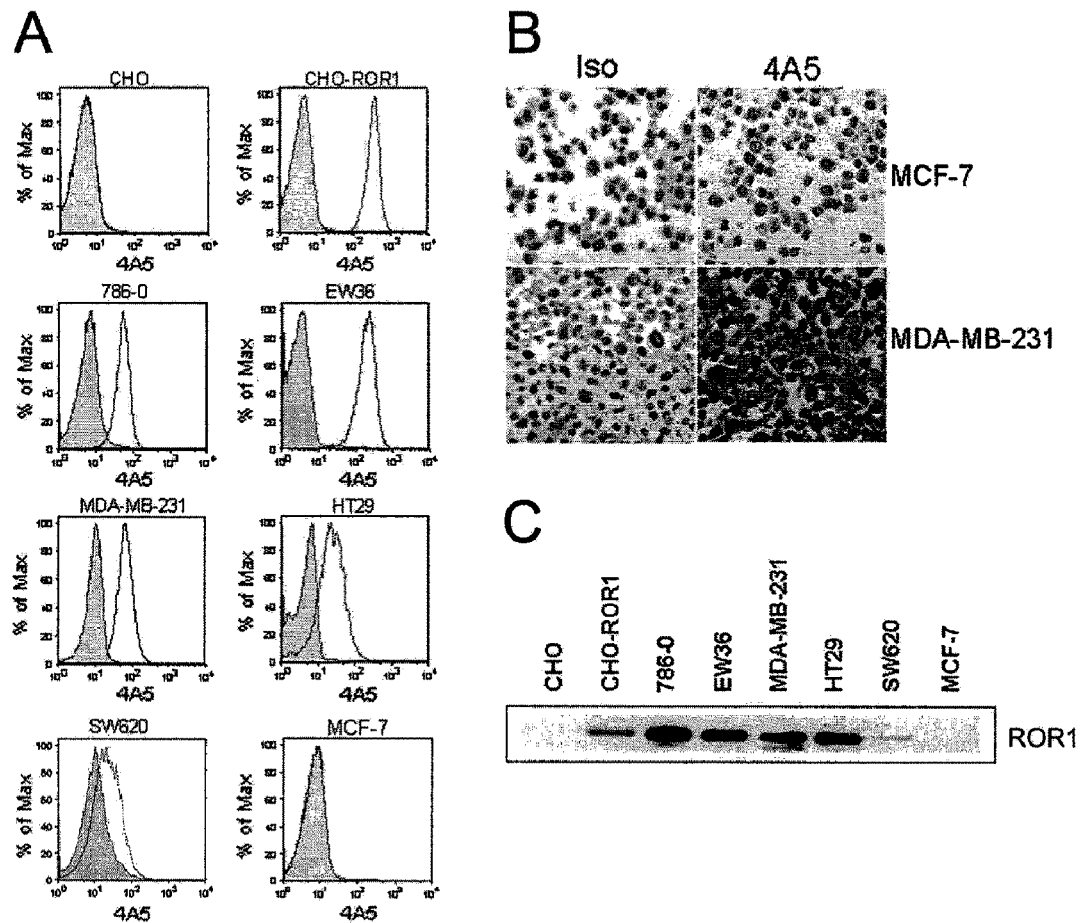
FIG. 22 illustrates expression of ROR1 protein in cancer cell lines.

Fresh frozen breast normal or cancer tissues were examined for ROR1 expression by immunohistochemistry using a monoclonal anti-ROR1 antibody (4A5). Additionally, cell lysate from breast normal or cancer tissues was examined for ROR1 expression by immunoblot using an anti-ROR1 antibody generated against an N-terminal-region synthetic peptide. As shown in FIG. 21A, breast tumor tissue showed staining with anti-ROR1 antibody but not with control antibody. Moreover, ROR1 was expressed on the cell surface in breast tumor tissue. In contrast, normal breast tissue did not stain with either 4A5 or control antibody. Immunoblot analysis demonstrated that the anti-ROR1 antibody detected a 125 kD protein in tumor breast cell lysates not in normal breast cell tissue lysates (FIG. 21B). ROR1 also detected on carcinomas of the colon, ovary, and bladder by immunohischemical staining of fresh-frozen tissue specimens.

To examine the frequency and distribution of ROR1 expression on various human cancers, immunohistochemistry was performed on tissue microarrays of paraffin-embedded sections with the anti-ROR1 antibody (4A5) and examined for expression of ROR1 and reviewed by a pathologist. ROR1 protein was expressed in large proportions of carcinomas of the breast, ovary, lung, colon, prostate, skin, bladder, testicules, pancreas, uterus, and adrenals and in various types of B-cell lymphomas. However, the normal cells of each of these tissues did not stain with the anti-ROR1 antibody. FIG. 21C depicts the frequency of cases of the various human cancers that stained with the anti-ROR1 antibody. ROR1 expression was found in 75% of breast tumor cases, 88% of ovarian tumor cases, 82% of lung tumor cases, 73% of testicular tumor cases, 89% of skin tumor cases, and 90% of various lymphoma cases. Furthermore, ROR1 is expressed in 57% of colon cancer cases, 43% of bladder cancer cases, and 57% of pancreatic cancer cases (FIG. 21D). Subtypes of breast tumor cases included in situ or invasive ductal carcinoma and lobular carcinoma. These subtypes have similar frequency of cases that express ROR1 expression as well as some, as do subtypes of ovarian, skin, or uterine cancer. However, only 60% of squamous cell lung carcinoma cases (n=29) expressed ROR1, whereas 90% of adenocarcinomas of the lung and 90% of large cell lung cancer cases expressed ROR1. Bladder urothelial carcinoma, small cell carcinoma and transitional cell carcinoma expressed high levels of ROR1 in 57% of the cases examined (n=30). ROR1 expression by other types of bladder cancer was not detected among the cases examined (n=10).

Figure 23:
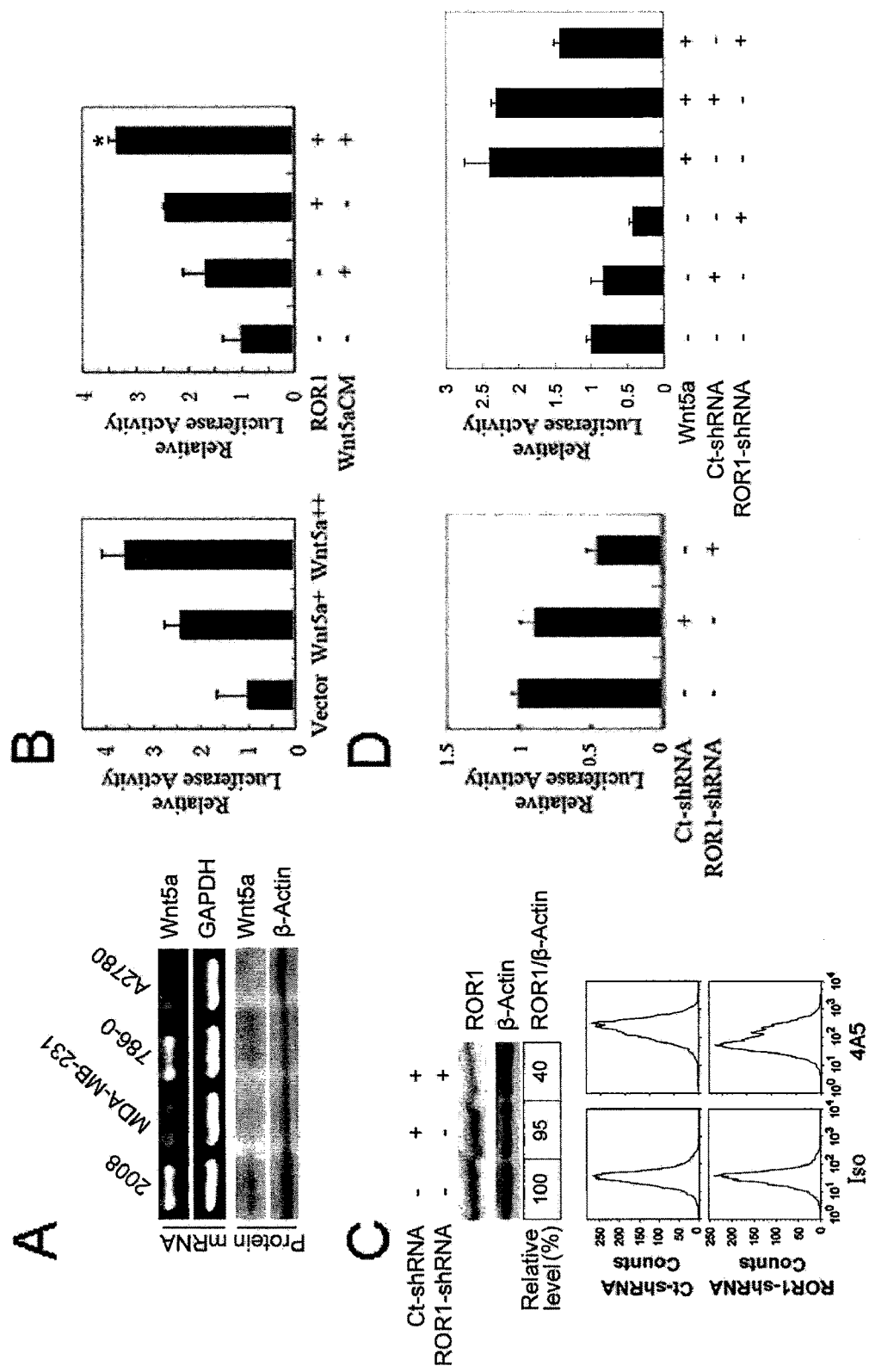

Similar to the noted expression on primary tumor tissues, various established human cancer cell lines also expressed ROR1 as detected using flow cytometry to detect binding of a fluorescence-labeled 4A5 anti-ROR1 antibody. Included in the human cancer cell lines tested were cancer cell lines derived from patients with breast cancer, colon cancer, B-lymphoma, or renal cancer (FIG. 23B). ROR1 also was found to be expressed at high levels on human cancer cell lines derived from patients with carcinomas of the ovary, prostate, pancreas, or bladder. Overall, 60% of breast cancer cell lines, 60% of pancreatic cancer cell lines, 67% of colon cancer cell lines, and 67% of bladder cancer cell lines expressed high-levels of ROR1. The frequency of positive cases for each tumor cell line is similar to that of ROR1 positive cases obtained from human tissue analysis.

ROR1 positive breast cancer cell lines MDA-MB-231 and ROR1 negative breast cancer cell lines MCF-7 were stained with 4A5 for ROR1 detection by immunohistochemistry. Similar to the results using flow cytometry, MDA-MB-231 cells, but not MCF-7 cells, were found to express ROR1 (FIG. 23A). Cell-lysates were prepared from tumor cell lines and each was immune precipitated with 4A5. The immune precipitate was subjected to electrophoresis for immunoblot analysis using different anti-ROR1 antibodies. Results showed that a ROR1 protein was present only in cells that are positive for ROR1 by FACS analysis (FIG. 23C).

ROR1 was Determined to Induce Activation of NF-κB in Human Cancer Cell Lines.

As shown herein, it was demonstrated that ROR1 could bind to Wnt5a. Fukuda et al. (2008) Proc Natl Acad Sci USA., 105:3047-3052. Co-transfection of ROR1 and Wnt5a induced NF-κB activation in 293 cells. Fukuda et al. (2008) Proc Natl Acad Sci USA., 105:3047-3052. The role of ROR1 in regulating Wnt5a-induced NF-κB activation was investigated in solid tumor cell lines. Wnt5A mRNA and protein expression of some tumor cell lines were determined by RT-PCR and immunoblot. As shown in FIG. 23A, the ovarian cancer cell line 2008 and the renal cancer cell line 786-0 express high Wnt5a mRNA and protein. On the other hand, the breast cancer cell line MDA-MB-231 and another ovarian cancer cell line A2780 expressed relatively low-levels of Wnt5a mRNA and protein. However, NF-κB signaling was significantly increased when MDA-MB-231 cells were transfected with Wnt5a expression-plasmids or when placed in Wnt5a-conditioned medium. Transfection of Wnt5a plasmids induced NF-κB activation in a dose-dependent manner (FIG. 23B, left panel). Moreover, increasing ROR1 expression enhanced the NF-κB signaling when MDA-MB-231 cells were cultured in media with, but not without, Wnt5a ($p<0.02$) (FIG. 24B, right panel).

To examine the functional significance of ROR1, ROR1-shRNA was generated to knock down ROR1 gene expression. As shown in FIG. 23C, transfection of MDA-MB-231 cells with ROR1-shRNA reduced the level of ROR1 expression relative to that of non-transduced cells or cells transduced with a control shRNA (Ct-shRNA). The effect of ROR1 on NF-κB activation was examined in MDA-MB-231 cells transfected with Wnt5a and 786-0 cells that expressed relatively high-levels of Wnt5a. The NF-κB signaling was significantly repressed after silencing expression of ROR1 in 786-0 cells (FIG. 23D, left panel). Furthermore, silencing-expression of ROR1 resulted in lower basal level transcriptional activation of NF-κB luciferase in MDA-MB-231 cells. Induction of NF-κB signaling with Wnt5a was attenuated by co-transfection with ROR1-shRNA, but not by co-transfection with Ct-shRNA in MDA-MB-231 cells (FIG. 3D, right panel).

ROR1 was Determined to Contribute to Cell Survival and Proliferation.

NF-κB signaling is a critical signaling of cell survival and studies on CLL have shown that ROR1 can enhance the survival of CLL cells. MDA-MB-231 cells were transfected with Ct-shRNA or ROR1-shRNA and resulting viability of the cells examined. Cells that expressed red-fluorescence protein (RFP) constituted the cells that had been transfected to express both RFP and the shRNA either Ct-shRNA or ROR1-shRNA (FIG. 24A). Consistent with this, RFP-positive cells transfected with ROR1-shRNA, but with Ct-shRNA, had reduced expression of ROR1 (FIG. 24B). Furthermore, the RFP-positive cells of cultures transfected with ROR1-shRNA had a lower viability than the RFP-negative cells in the same culture, or the RFP-positive or negative cells in cultures transfected with Ct-shRNA. There was no difference in the viability of RFP-negative cells in either culture. The viability of the RFP-positive cells of cultures transfected with ROR1-shRNA was approximately 70% (with 30% apoptotic cells), which was significantly lower than the viability of RFP-negative cells and RFP-positive cells of cultures transfected with Ct-shRNA (FIG. 24B), or of control non-transfected cell cultures, which generally was >90% and typically had <10 apoptotic cells ($p<0.01$).

Figure 24:
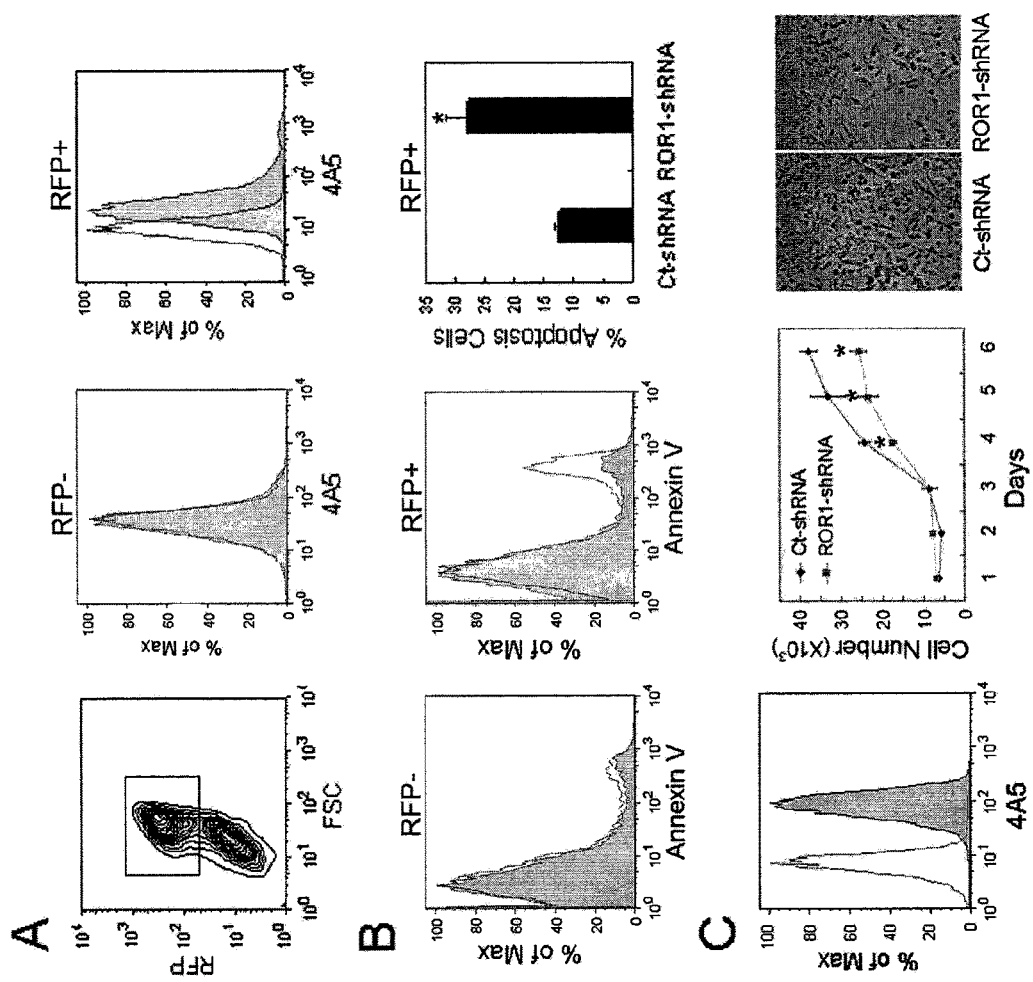
FIG. 24 illustrates that knockdown of ROR1 reduces cell survival and proliferation.

MDA-MB-231 cells transfected with Ct-shRNA or ROR1-shRNA were selected to generate stable cell lines that did or did not express ROR1 (FIG. 24C). Equal amounts of MDA-MB-231 cells transfected with Ct-shRNA or ROR1-shRNA was seeded and cell number was counted at different time points with CCK assay. The MDA-MB-231 cells with low-negligible expression of ROR1 had significantly slower growth in vitro than MDA-MB-231 cells that expressed ROR1. Moreover, the numbers of cells for each culture were significantly lower in cells transfected with ROR1-shRNA than that in cells transfected with Ct-shRNA on day 4 (p<0.05) (FIG. 24). These data together indicate that silencing ROR1 sensitizes the cells to apoptosis and represses cell proliferation.

Silencing Expression of ROR1 was Determined to Impair Tumor Cell Growth In Vivo.

Figure 25:
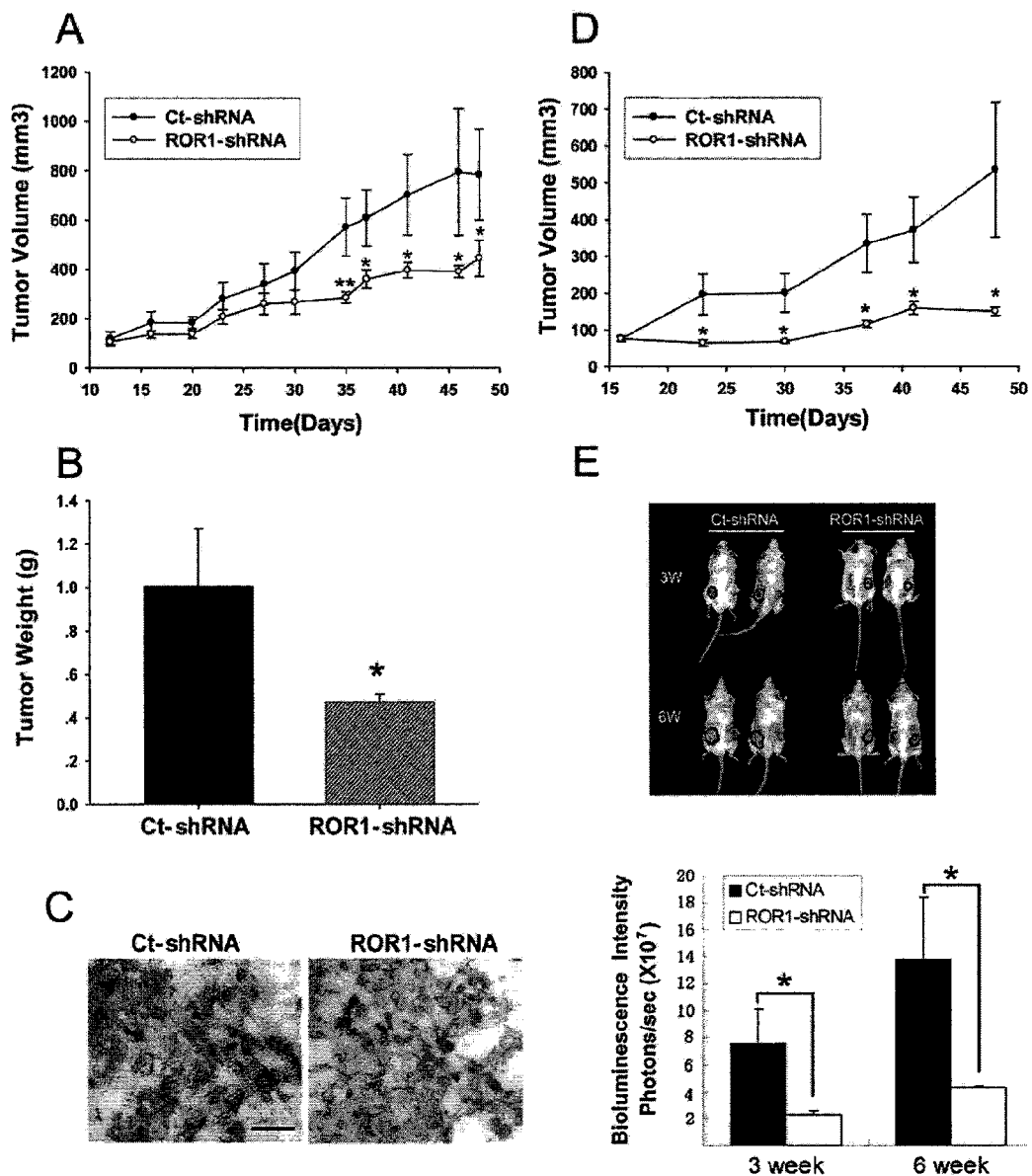
FIG. 25 illustrates that ROR1 depletion inhibits the growth of MDA-MB-231 tumor engraftments in immunodeficient mice.
Figure 26:
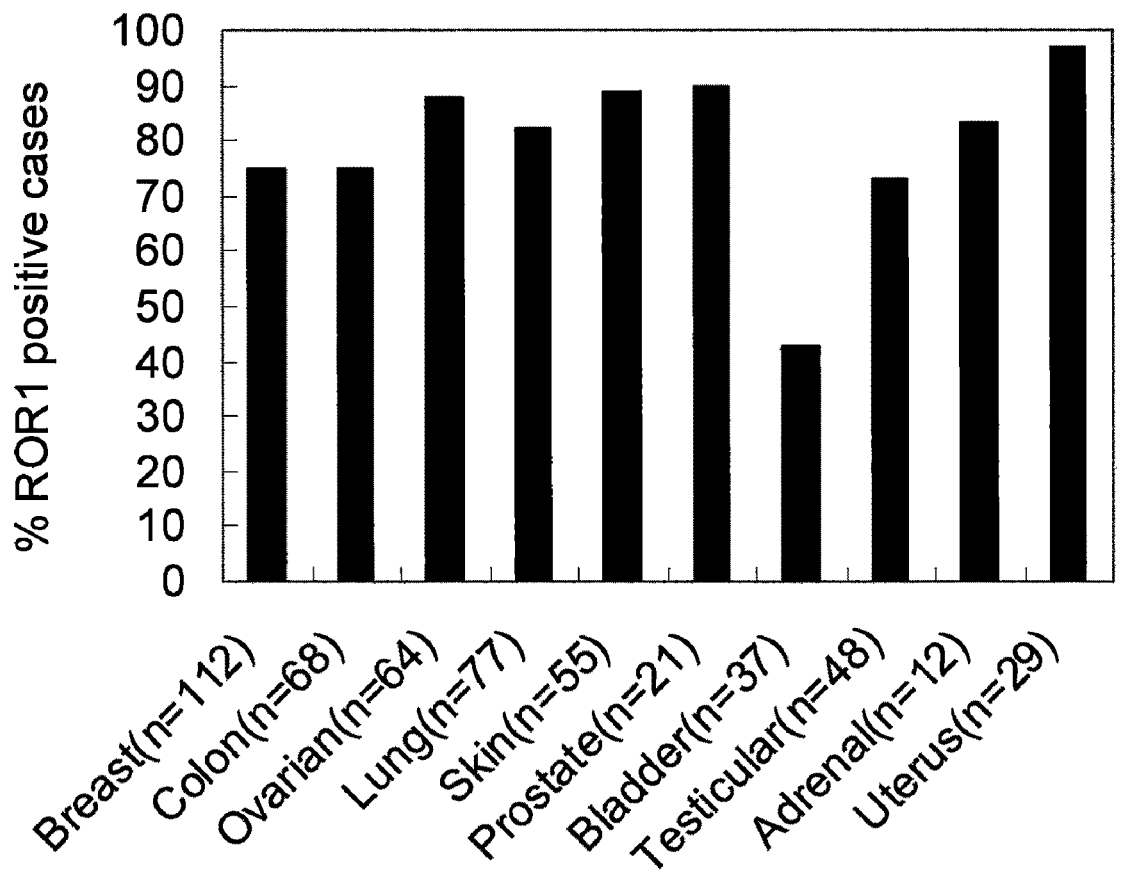
FIG. 26 shows a graph depicting the frequency of ROR1 overexpression in various tumor tissues.

After determining ROR1 function in vitro, the role of ROR1 on tumor growth in vivo was investigated. Female immunodeficient mice lacking Rag and the common gamma chain ($Rag^{-/-}\gamma^{-/-}$) were implanted with stable MDA-MB-231 cells that had been transfected with Ct-shRNA or ROR1-shRNA, respectively. Tumor growth was monitored from day 12 to day 48 after injection. A difference in tumor size was detected in animals given MDA-MB-231 lacking ROR1 versus mice given equal numbers of viable MDA-MB-231 cells that expressed ROR1 at day 35. Silencing ROR1 resulted in tumor sizes that were approximately 40% of that generated by MDA-MB-231 cells that expressed ROR1 (p=0.004). This difference in tumor cell growth became more apparent over time (FIG. 25A). Consistent with the repression of ROR1 knockdown to tumor size, tumor weight was significantly decreased in tumors obtained from mice given MDA-MB-231 cells transfected with ROR1-shRNA relative to that of mice given MDA-MB-231 transfected with control sh-RNA (p<0.04) (FIG. 25B).

The tumors excised from the mice were examined via immune histochemistry to determine whether they expressed ROR1. It was found that the tumors transfected with ROR1-shRNA had low-to-negligible expression of ROR1 (FIG. 5C).

Luciferase was used to monitor tumor growth in vivo in real time. Control and ROR1-shRNA transfected MDA-MB-231 cells were labeled with luciferase and injected into $Rag^{-/-}\gamma^{-/-}$ mice. After measurement of tumor size from the $2^{nd}$ to $6^{th}$ week, the mice given cells lacking expression of ROR1 had significantly smaller tumors relative to that of animals that received luciferase-tagged control MDA-MB-231 cells (FIGS. 5D and 5A). Luciferase signaling was measured at three weeks and six weeks after the injection. In agreement with prior studies the luciferase signal in mice that received cells lacking ROR1 was significantly smaller than that noted in animals that received MDA-MB-231 cells transfected with Ct-shRNA (FIG. 5E, upper panel). The signaling intensity of ROR1 knockdown group was about 60% of that in the control group (FIG. 5E, lower panel, p<0.03).

Although the present methods and compositions have been described with reference to specific details of certain embodiments thereof in the above examples, it will be understood that modifications and variations are encompassed within the spirit and scope of the invention. Accordingly, the invention is limited only by the following claims.

What is claimed is:

1. An isolated antibody that specifically binds ROR1 protein, wherein the antibody comprises the VH chain sequence of SEQ ID NO:3 and the VL chain sequence of SEQ ID NO:6.

2. The antibody of claim 1, wherein the antibody specifically binds ROR1 protein with a dissociation constant of below a Kd value selected from the group consisting of $10^{-6}$ mol/l, $10^{-7}$ mol/l, and $10^{-8}$ mol/l.

3. The antibody of claim 1, wherein the ROR1 protein is encoded by the nucleotide sequence of SEQ ID NO: 1.

4. The antibody of claim 1, wherein the ROR1 protein comprises the amino acid sequence as set forth in SEQ ID NO: 2.

5. The antibody of claim 1, wherein the antibody is humanized.

6. The antibody of claim 1, wherein the antibody is a functional antibody fragment.

7. The antibody of claim 1, wherein the antibody is chimeric.

8. The antibody of claim 1, wherein the antibody is selected from the group consisting of whole antibody, Fab fragment, Fab' fragment, F(ab')$_2$ fragment, single chain Fv fragment and diabody.

9. The antibody of claim 1, wherein the antibody is detectably labeled.

* * * * *